(12) United States Patent
Shima et al.

(10) Patent No.: US 7,129,243 B2
(45) Date of Patent: Oct. 31, 2006

(54) PEPTIDE COMPOUNDS

(75) Inventors: Ichiro Shima, Osaka (JP); Takehiko Ohkawa, Osaka (JP); Kentaro Sato, Osaka (JP); Naoki Ishibashi, Osaka (JP); Kenichiro Imamura, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 12 days.

(21) Appl. No.: 10/250,444

(22) PCT Filed: Dec. 18, 2001

(86) PCT No.: PCT/JP01/11067

§ 371 (c)(1),
(2), (4) Date: Dec. 23, 2003

(87) PCT Pub. No.: WO02/055541

PCT Pub. Date: Jul. 18, 2002

(65) Prior Publication Data

US 2004/0097425 A1    May 20, 2004

(30) Foreign Application Priority Data

Jan. 2, 2001 (AU) .................................. PR2371
Sep. 5, 2001 (AU) .................................. PR7506

(51) Int. Cl.
*A61K 31/50* (2006.01)

(52) U.S. Cl. ............ 514/252.03; 514/255.05; 514/269; 514/318; 514/333; 514/369; 544/238; 544/319; 544/405; 546/194; 546/256; 548/189

(58) Field of Classification Search ........... 544/238, 544/319, 405; 546/194, 256; 548/189; 514/252.03, 514/255.05, 269, 318, 333, 369
See application file for complete search history.

(56) References Cited

U.S. PATENT DOCUMENTS 5,932,737 A    8/1999    Hamashima et al.
6,069,162 A    5/2000    Itoh et al.

FOREIGN PATENT DOCUMENTS

WO    01 32690    5/2001

OTHER PUBLICATIONS

Zanzinger, PubMed Abstract (Auton Neurosci. 98(1-2):24-7) Jun. 2002.*
Singh et al., Immune therapy in inflammatory bowel disease and models of colitis, British Journal of Surgery, 88, pp. 1558-1569, 2001.*
Robinson, Medical Therapy of Inflammatory Bowel Disease for the 21st Century, Eur J Surg, Suppl 582: 90-98, 1998.*
Bremner et al., Therapy of Crohn's Disease in childhood, Expert Opinion Pharmacother. 3(&):809-825, 2002.*
Layzer, Degenerative Diseases of the Nervous System, Cecil Textbook of Medicine, 20th Edition, vol. 2, pp. 2050-2057, 1996.*
Damasio, Alzheimer's Disease and Related Dementias, Cecil Textbook of Medicine, 20th Edition, vol. 2, pp. 1992-1996, 1996.*
Simone, Oncology: Introduction, Cecil Textbook of Medicine, 20th Edition, vol. 1, pp. 1004-1010, 1996.*

* cited by examiner

*Primary Examiner*—Deepak Rao
(74) *Attorney, Agent, or Firm*—Oblon, Spivak, McClelland, Maier & Neustadt, P.C.

(57) ABSTRACT

The present invention relates to a compound of the formula (I) wherein R1 is benzofuranyl substituted by halogen, or styryl substituted by halogen; R2 is substituted hydroxy, substituted mercapto or substituted sulfonyl; and X is or pharmaceutically acceptable salts thereof. The compound (1) of the present invention and pharmaceutically acceptable salts thereof possess a strong inhibitory activity on the production of nitric oxide (NO), and are useful for prevention and/or treatment of NO-mediated diseases in human being and animals (I)

19 Claims, No Drawings

US 7,129,243 B2

PEPTIDE COMPOUNDS

This application is a 371 of PCT/JP01/11067 filed Dec. 18, 2001.

TECHNICAL FIELD

This invention relates to new peptide compounds and pharmaceutically acceptable salts thereof which are useful as a medicament.

BACKGROUND ART

Some peptide compounds have been known as described in, for example, EP 0 394 989 A2, WO96/16981 and JP-A-10-81671.

DISCLOSURE OF INVENTION

This invention relates to new peptide compounds.

One object of this invention is to provide the new and useful peptide compounds and pharmaceutically acceptable salts thereof that possess a strong inhibitory activity on the production of nitric oxide (NO).

Another object of this invention is to provide a process for the preparation of the peptide compounds and salts thereof.

A further object of this invention is to provide a pharmaceutical composition comprising said peptide compound or a pharmaceutically acceptable salt thereof.

Still further object of this invention is to provide a use of said peptide compounds or pharmaceutically acceptable salts thereof as a medicament for prophylactic and therapeutic treatment of NO-mediated diseases including respiratory diseases such as adult respiratory distress syndrome (ARDS) and asthma; cardiovascular diseases such as cardiovascular ischemia, myocarditis, heart failure, hypotension and atherosclerosis; endocrine diseases such as diabetes (e.g., insulin-dependent diabetes mellitus, etc.), complications of diabetes mellitus (e.g., diabetic nephropathy, diabetic retinopathy, diabetic neuropathy, etc.) and gout; renal diseases such as glomerulonephritis and renal failure; gastrointestinal diseases such as peptic ulcer and inflammatory bowel disease (e.g., ulcerative colitis, chronic colitis, etc.); pancreatic diseases such as pancreatitis; hepatic diseases such as hepatitis and liver cirrhosis; diseases of bone or joint such as synovitis, arthritis, osteoarthritis, osteoporosis; autoimmune diseases such as rheumatoid arthritis, systemic lupus erythematosus and multiple sclerosis; dermal diseases such as dermatitis and eczema; cancer such as solid tumors and metastasis; rejection by organ transplantation; shock (e.g., septic shock, etc.); sepsis-induced systemic inflammatory response syndrome; and sexual dysfunction such as male sexual dysfunction (e.g., erectile dysfunction) and female sexual dysfunction (e.g., orgasmic dysfunction related to clitoral disturbances) in human being and animals.

The object peptide compounds of the present invention are novel and can be represented by the following general formula (I):

$$R^1-CONH-CH(CH_2-pyridyl)-CONH-CH_2-CO-N(X)(R^2) \quad (I)$$

wherein
R$^1$ is benzofuranyl substituted by halogen, or styryl substituted by halogen;
R$^2$ is substituted hydroxy, substituted mercapto or substituted sulfonyl; and
X is (hexagon), (pentagon) or (square).

Suitable pharmaceutically acceptable salts of the object compound (I) are conventional non-toxic salts and include, for example, a salt with a base or an acid addition salt such as a salt with an inorganic base, for example, an alkali metal salt (e.g., sodium salt, potassium salt, etc.)., an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, citrate, fumarate, methanesulfonate, benzenesulfonate, toluenesulfonate, etc.); and a salt with a basic or acidic amino acid (e.g., arginine, aspartic acid, gultamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

Suitable "halogen" includes, for example, fluorine, bromine, chlorine and iodine.

"Styryl substituted by halogen" means styryl which has halogen atom as a substituent on the benzene ring. Suitable examples of "styryl substituted by halogen" include 2-(2-chlorophenyl)ethenyl, 2-(3-chlorophenyl)ethenyl, 2-(4-chlorophenyl)ethenyl, 2-(2-bromophenyl)ethenyl, 2-(3-bromophenyl)ethenyl, 2-(4-bromophenyl)ethenyl, 2-(2-fluorophenyl)ethenyl, 2-(3-fluorophenyl)ethenyl, 2-(4-fluorophenyl)ethenyl, and the like.

"Substituted hydroxy" means a group of the formula: —Y—R$^3$ wherein Y is —O— and R$^3$ is a suitable organic group.

"Substituted mercapto" means a group of the formula: —Y—R$^3$ wherein Y is —S— and R$^3$ is a suitable organic group.

"Substituted sulfonyl" means a group of the formula: —Y—R$^3$ wherein Y is —SO$_2$— and R$^3$ is a suitable organic group.

Examples of the above-mentioned "suitable organic group" include lower alkyl, halo(lower)alkyl, optionally substituted heterocyclic group and optionally substituted aryl. Each of said heterocyclic group and aryl is optionally substituted by one or more, preferably one to three substitutent(s) such as lower alkyl, lower alkoxy, halogen, halo (lower)alkyl, and the like.

In the formula: —Y—R$^3$, Y is preferably —O—.

"Heterocyclic group" includes saturated or unsaturated, heteromonocyclic or fused heterocyclic group containing heteroatom(s) selected from the group consisting of nitrogen atom, sulfur atom and oxygen atom.

Suitable examples of "heterocyclic group" include unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidinyl, pyrazinyl, pyridazinyl, tirazolyl, (e.g., 4H-1,2,4-triazolyl, 1H-1,2,3-triazolyl, 2H-1,2,3-triazolyl), tetrazolyl (e.g., 1H-tetrazolyl, 2H-tetrazolyl), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated fused heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5-or 6-membered) heteromonocyclic group containing 1 or 2 oxygen atom(s) and 1 to 3 nitrogen atom(s), for example, oxazolyl, isoxazolyl, oxadiazolyl (e.g.; 1,2,4-oxadiazolyl, 1,3,4-oxadiazolyl, 1,2,5-oxadiazolyl) etc.;

saturated 3 to 8-membered (more preferably 5 or 6-membered) heteromonocyclic group containing 1 or 2 oxygen atom(s) and 1 to 3 nitrogen atom(s), for example, morpholinyl, sydnonyl, etc.;

unsaturated fused heterocyclic group containing 1 or 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 or 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl), dihydrothiazinyl, etc.;

saturated 3 to 8-membered (more preferably 5 or 6-membered) heteromonocyclic group containing 1 or 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 or 2 sulfur atom(s), for example, thienyl, dihydrodithiinyl, etc.;

unsaturated fused heterocyclic group containing 1 or 2 sulfur atom(s) and 1 to 3 nitrogen atom(s), for example, benzothiazolyl, benzothiadiazolyl, imidazothiadiazolyl, etc.;

unsaturated 3 to 8-membered (more preferably 5 or 6-membered) heteromonocyclic group containing an oxygen atom, for example, furyl, etc.;

saturated 3 to 8-membered (more preferably 5 or 6-membered) heteromonocyclic group containing an oxygen atom, for example, tetrahydrofuranyl, tetrahydropyranyl, etc.;

saturated 3 to 8-membered (more preferably 5 or 6-membered) heteromonocyclic group containing an oxygen atom and 1 or 2 sulfur atom(s), for example, dihydrooxathiinyl, etc.;

unsaturated fused heterocyclic group containing 1 or 2 sulfur atom(s), for example, benzothienyl, benzodithiinyl, etc.;

unsaturated fused heterocyclic group containing an oxygen atom and 1 or 2 sulfur atom(s), for example, benzoxathiinyl, etc.; and the like.

Preferable examples of heterocyclic group include unsaturated 5 or 6-membered heteromonocyclic group containing 1 to 4 nitrogen atom(s); and unsaturated 5 or 6-membered heteromonocyclic group containing 1 or 2 sulfur atom(s) and 1 to 3 nitrogen atom(s).

More preferable examples of heterocyclic group include pyridyl, pyrazinyl, thiazolyl, pyridazinyl and pyrimidinyl, and particularly preferable examples of heterocyclic group are pyridyl, pyrazinyl and thiazolyl.

Suitable "aryl" includes $C_6$–$C_{12}$ aryl such as phenyl and naphthyl, in which more preferred one is phenyl.

Suitable "lower alkyl" and "lower alkyl" moiety in the term "halo(lower)alkyl" include straight or branched alkyl having 1 to 6 carbon atom(s), such as methyl, ethyl, propyl, isopropyl, butyl, isobutyl, sec-butyl, tert-butyl, pentyl, tert-pentyl and hexyl, in which more preferred one is $C_1$–$C_4$ alkyl.

Suitable "lower alkoxy" includes straight or branched alkoxy having 1 to 6 carbon atom(s), such as methoxy, ethoxy, propoxy, isopropoxy, butoxy, isobutoxy, sec-butoxy, tert-butoxy, pentyloxy, tert-pentyloxy and hexyloxy, in which more preferred one is $C_1$–$C_4$ alkoxy.

Suitable "halo(lower)alkyl" includes lower alkyl substituted by one or more, preferably one to three halogen atom(s) such as trifluoromethyl, trichloromethyl, tribromomethyl, 2,2,2-trifluoroethyl and 3,3,3-trifluoropropyl, in which more preferred one is trihalo(lower)alkyl.

Suitable examples of optionally substituted heterocyclic group include 2-pyridyl, 3-pyridyl, 4-pyridyl, 6-methoxy-2-pyridyl, 6-methyl-2-pyridyl, 5-chloro-2-pyridyl, 6-chloro-2-pyridyl, 3-chloro-2-pyridyl, 3,5-dichloro-2-pyridyl, 3-(trifluoromethyl)-2-pyridyl, 5-(trifluoromethyl)-2-pyridyl, 2-pyrazinyl, 5-chloro-2-pyrazinyl, 6-chloro-2-pyrazinyl, 1,3-thiazol-2-yl, 1,3-thiazol-4-yl, 1,3-thiazol-5-yl, 5-methyl-1,3-thiazol-2-yl, 5-chloro-1,3-thiazol-2-yl, 3-pyridazinyl, 4-pyridazinyl, 6-chloro-3-pyridazinyl, 6-methoxy-3-pyridazinyl, 2-pyrimidinyl, 4-pyrimidinyl, 5-pyrimidinyl, 6-chloro-4-pyrimidinyl, 6-(trifluoromethyl)-4-pyrimidinyl, 2-(trifluoromethyl)-4-pyrimidinyl, and the like.

Suitable examples of optionally substituted aryl include phenyl, 2-chlorophenyl, 3-chlorophenyl, 4-chlorophenyl, 2-fluorophenyl, 3-fluorophenyl, 4-fluorophenyl, 2-(trifluoromethyl)phenyl, 3-(trifluoromethyl)phenyl, 4-(trifluoromethyl)phenyl, and the like.

In the formula (I), a group of the formula:

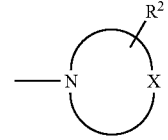

is preferably

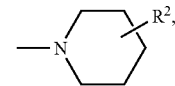

more preferably

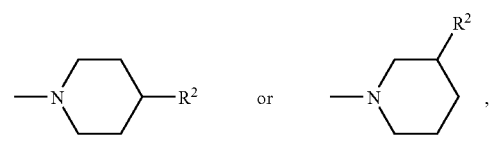

and particularly preferably

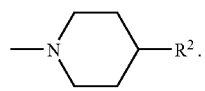

Suitable "amino-protecting group" includes, for example, acyl and conventional protecting group such as mono (or di or tri)aryl(lower)alkyl, for example, mono(or di or tri)phenyl (lower)alkyl (e.g., benzyl, trityl, etc.). Suitable examples of said acyl include aliphatic acyl such as lower alkanoyl which may be substituted by one to three halogen atoms (e.g., formyl, acetyl, propanoyl, butanoyl, 2-methylpropanoyl, pentanoyl, 2,2-dimethylpropanoyl, hexanoyl, trichloroacetyl, trifluoroacetyl, etc.), lower alkoxycarbonyl (e.g., methoxycarbonyl, ethoxycarbonyl, tert-butoxycarbonyl, tert-pentyloxycarbonyl, etc.), aryl(lower)alkoxycarbonyl [e.g., phenyl(lower)-alkoxycarbonyl (e.g., benzyloxycarbonyl, etc.), etc.] and the like.

Suitable "carboxy-protecting group" includes, for example, lower alkyl (e.g., methyl, ethyl, propyl, isopropyl, butyl, sec-butyl, isobutyl, tert-butyl, pentyl, neopentyl, hexyl, etc.), optionally substituted phenyl(lower)alkyl, for example, mono(or di or tri)phenyl(lower)alkyl which may be substituted by nitro (e.g., benzyl, 4-nitrobenzyl, benzhydryl, trityl, etc.) and the like.

The object compound (I) of the present invention can be prepared by the following processes.

Process (1)

$R^1$—COOH +

(II)
or its reactive derivative
at the carboxy group,
or a salt thereof

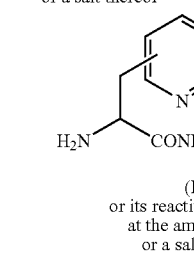

(III)
or its reactive derivative
at the amino group,
or a salt thereof

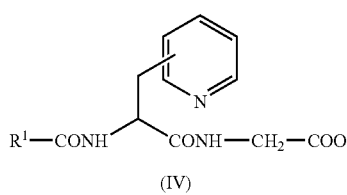

(I)
or a salt thereof

Process (2)

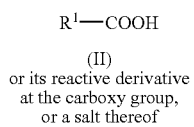

(IV)
or its reactive derivative
at the carboxy group,
or a salt thereof

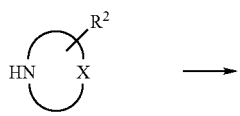

(V)
or a salt thereof

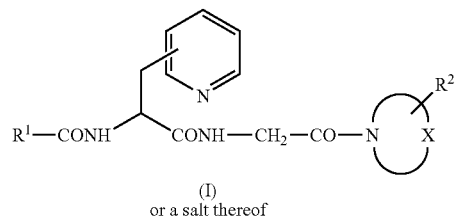

(I)
or a salt thereof wherein $R^1$, $R^2$ and X are each as defined above.

The starting compounds can be prepared by the following processes.

Process (A)

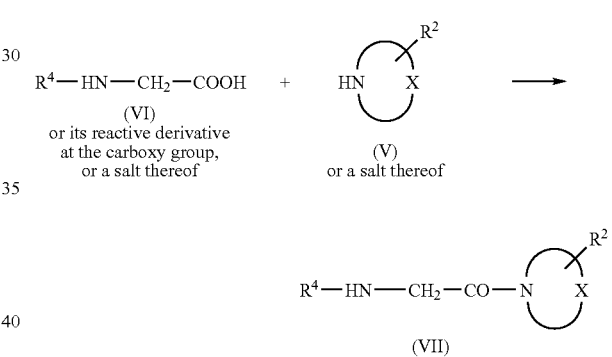

Process (B)

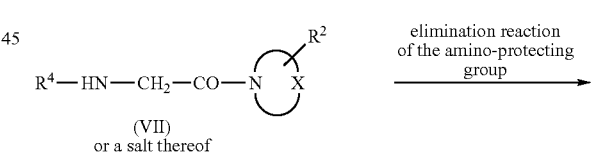

Process (C)

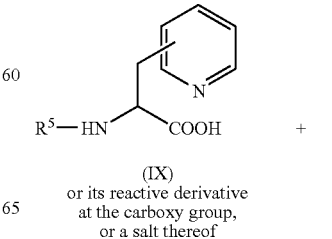

(IX)
or its reactive derivative
at the carboxy group,
or a salt thereof

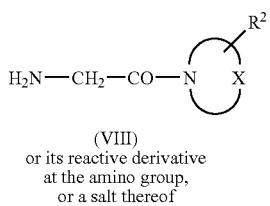
(VIII)
or its reactive derivative
at the amino group,
or a salt thereof

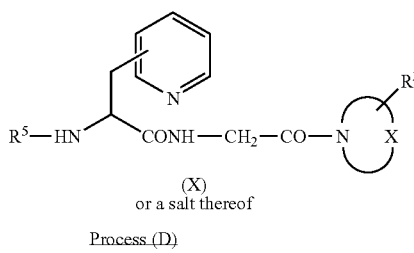
(X)
or a salt thereof

Process (D)

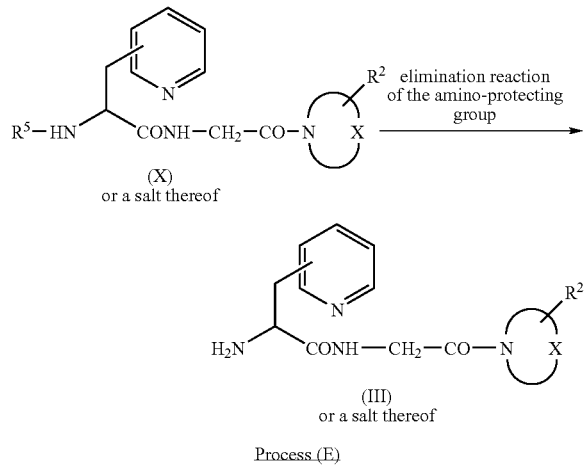
(X)
or a salt thereof (III)
or a salt thereof

Process (E)

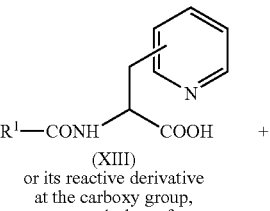
(II)
or its reactive derivative
at the carboxy group,
or a salt thereof (XI)
or its reactive derivative
at the amino group,
or a salt thereof

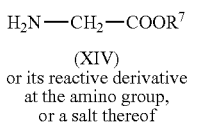
(XII)
or salt thereof

Process (F)

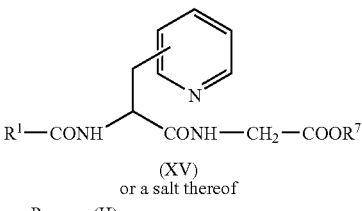
(XII)
or a salt thereof

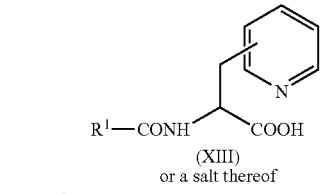
(XIII)
or a salt thereof

Process (G)

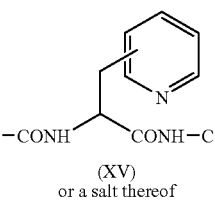
(XIII)
or its reactive derivative
at the carboxy group,
or a salt thereof $H_2N-CH_2-COOR^7$
(XIV)
or its reactive derivative
at the amino group,
or a salt thereof

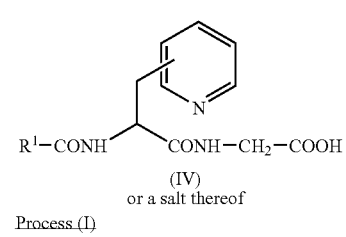
(XV)
or a salt thereof

Process (H)

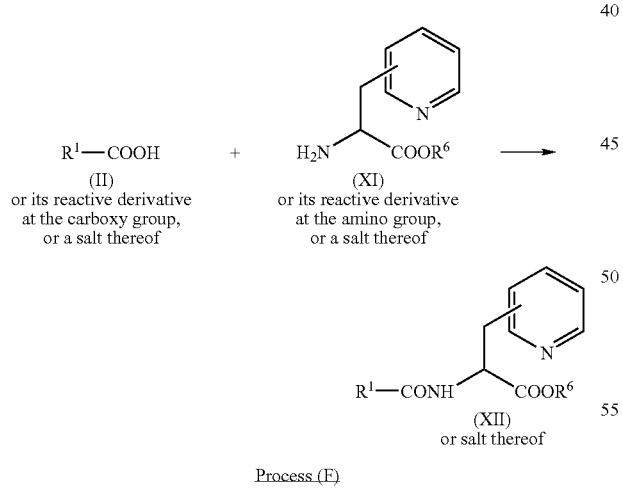
(XV)
or a salt thereof

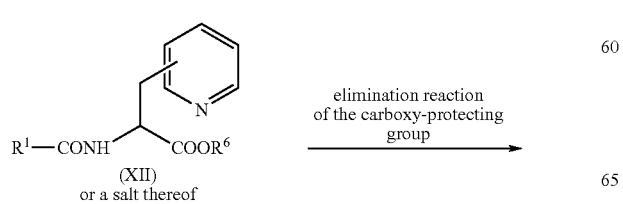
(IV)
or a salt thereof

Process (I)

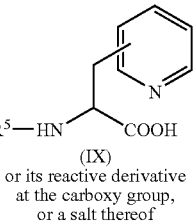
(IX)
or its reactive derivative
at the carboxy group,
or a salt thereof $H_2N-CH_2-COOR^7$
(XIV)
or its reactive derivative
at the amino group,
or a salt thereof

(XVI)
or a salt thereof

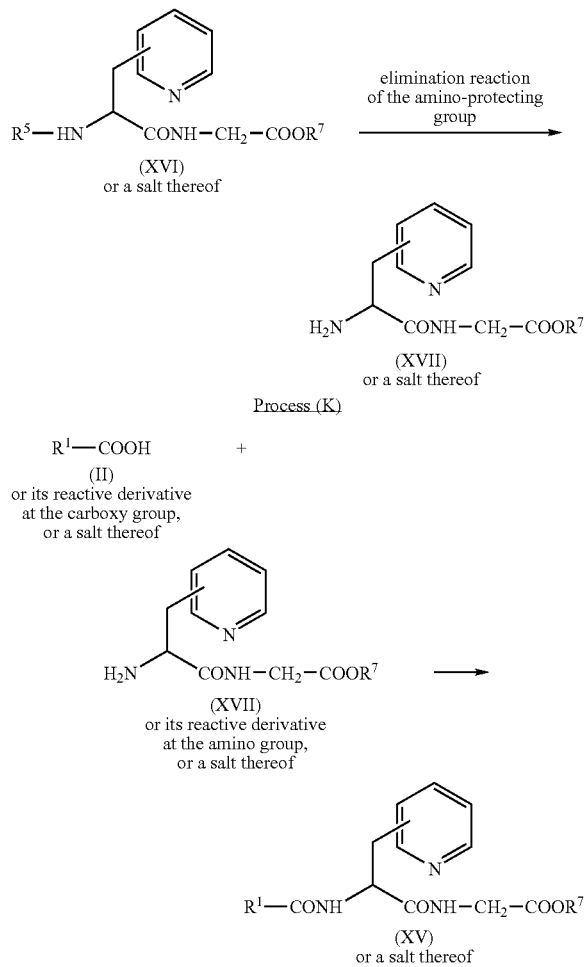

wherein $R^1$, $R^2$, and X are each as defined above, $R^4$ and $R^5$ are each amino-protecting group, and $R^6$ and $R^7$ are each carboxy-protecting group.

The processes for preparing the object compound are explained in detail in the following.

Process (1)

The compound (I) or a salt thereof can be prepared by reacting the compound (II) or its reactive derivative at the carboxy group, or a salt thereof with the compound (III) or its reactive derivative at the amino group, or a salt thereof.

Suitable reactive derivative of the compound (III) includes Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as N,O-bis(trimethylsilyl)acetamide, N-trimethylsilylacetamide or the like; a derivative formed by the reaction of the compound (III) with phosphorus trichloride or phosgene.

Suitable reactive derivative of the compound (II) includes an acid halide, an acid anhydride and an activated ester. The suitable example may be an acid chloride; an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl $[(CH_3)_2N^+=CH—]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.); or an ester with an N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.). These reactive derivatives can optionally be selected from them according to the kind of the compound (II) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely affect the reaction, or the mixture thereof.

When the compound (II) is used in free acid form or its salt form in the reaction, the reaction is preferably carried out in the presence of a conventional condensing agent such as N,N'-dicyclohexylcarbodiimide; N-cyclohexyl-N'-morpholinoethyl-carbodibmide; N-cyclohexyl-N'-(4-diethylaminocyclohexyl)-carbodiimide; N,N'-diisopropylcarbodiimide; N-ethyl-N'-(3-dimethylaminopropyl)carbodiimide; N,N-carbonyl-bis-(2-methylimidazole); pentamethyleneketene-N-cyclohexylimine; diphenylketene-N-cyclohexylimine; ethoxyacetylene; 1-alkoxy-1-chloroethylene; trialkyl phosphite; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an organic or inorganic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to heating.

Process (2)

The compound (I) or a salt thereof can be prepared by reacting the compound (IV) or its reactive derivative at the carboxy group, or a salt thereof with the compound (V) or a salt thereof.

This reaction can be carried out in a similar manner to the reaction in the aforementioned Process (1), and therefore the reagents to be used and reaction conditions (e.g., solvent, reaction temperature, etc.) can be referred to those of Process (1).

Process (A)

The compound (VII) or a salt thereof can be prepared by reacting the compound (VI) or its reactive derivative at the carboxy group, or a salt thereof with the compound (V) or a salt thereof.

This reaction can be carried out in a similar manner to the reaction in the aforementioned Process (1), and therefore the reagents to be used and reaction conditions (e.g., solvent, reaction temperature, etc.) can be referred to those of Process (1).

Process (B)

The compound (VIII) or a salt thereof can be prepared by subjecting the compound (VII) or a salt thereof to elimination reaction of the amino-protecting group.

Suitable method of this elimination reaction includes conventional one such as hydrolysis, reduction and the like.

(i) For Hydrolysis:

The hydrolysis is preferably carried out in the presence of a base or an acid including Lewis acid.

Suitable base includes an inorganic base and an organic base such as an alkali metal (e.g., sodium, potassium, etc.), an alkaline earth metal (e.g., magnesium, calcium, etc.), the hydroxide or carbonate or hydrogencarbonate thereof, trialkylamine (e.g., trimethylamine, triethylamine, etc.), picoline, 1,5-diazabicyclo[4.3.0]non-5-ene, or the like.

Suitable acid includes an organic acid (e.g., formic acid, acetic acid, propionic acid, trichloroacetic acid, trifluoroacetic acid, etc.), and an inorganic acid (e.g., hydrochloric acid, hydrobromic acid, sulfuric acid, hydrogen chloride, hydrogen bromide, etc.).

The elimination using Lewis acid such as trihaloacetic acid (e.g., trichloroacetic acid, trifluoroacetic acid, etc.), or the like is preferably carried out in the presence of a cation trapping agent (e.g., anisole, phenol, etc.). This reaction is usually carried out without solvent.

The reaction may be carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or a mixture thereof.

The reaction temperature is not critical and the reaction is usually carried out under cooling to warming.

(ii) For Reduction:

Reduction is carried out in a conventional manner, including chemical reduction and catalytic reduction.

Suitable reducing reagent to be used in chemical reduction are hydrides (e.g., hydrogen iodide, hydrogen sulfide, lithium aluminum hydride, sodium borohydride, sodium cyanoborohydride, etc.), or a combination of a metal (e.g., tin, zinc, iron, etc.) or metallic compound (e.g., chromium chloride, chromium acetate, etc.) and an organic acid or inorganic acid (e.g., formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, palladium hydroxide on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, Raney iron, Ullman iron, etc.), and the like.

The reduction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or a mixture thereof.

Additionally, in case that the above-mentioned acids to be used in chemical reduction are in a liquid state, they can also be used as a solvent.

The reaction temperature of this reduction is not critical and the reaction is usually carried out under cooling to warming.

Process (C)

The compound (X) or a salt thereof can be prepared by reacting the compound (IX) or its reactive derivative at the carboxy group, or a salt thereof with the compound (VIII) or its reactive derivative at the amino group, or a salt thereof.

This reaction can be carried out in a similar manner to the reaction in the aforementioned Process (1), and therefore the reagents to be used and reaction conditions (e.g., solvent, reaction temperature, etc.) can be referred to those of Process (1).

Process (D)

The compound (III) or a salt thereof can be prepared by subjecting the compound (X) or a salt thereof to elimination reaction of the amino-protecting group.

This reaction can be carried out in a similar manner to the reaction in the aforementioned Process (B), and therefore the reagents to be used and reaction conditions (e.g., solvent, reaction temperature, etc.) can be referred to those of Process (B).

Process (E)

The compound (XII) or a salt thereof can be prepared by reacting the compound (II) or its reactive derivative at the carboxy group, or salt thereof with the compound (XI) or its reactive derivative at the amino group, or a salt thereof.

This reaction can be carried out in a similar manner to the reaction in the aforementioned Process (1), and therefore the reagents to be used and reaction conditions (e.g.; solvent, reaction temperature, etc.) can be referred to those of Process (1).

Process (F)

The compound (XIII) or a salt thereof can be-prepared by subjecting the compound (XII) or a salt thereof to elimination reaction of the carboxy-protecting group.

This reaction can be carried out in a similar manner to the reaction in the aforementioned Process (B), and therefore the reagents to be used and reaction conditions (e.g., solvent, reaction temperature, etc.) can be referred to those of Process (B).

Process (G)

The compound (XV) or a salt thereof can be prepared by reacting the compound (XIII) or its reactive derivative at the carboxy group, or a salt thereof with the compound (XIV) or its reactive derivative at the amino group, or a salt thereof.

This reaction can be carried out in a similar manner to the reaction in the aforementioned Process (1), and therefore the reagents to be used and reaction conditions (e.g., solvent, reaction temperature, etc.) can be referred to those of Process (1).

Process (H)

The compound (IV) or a salt thereof can be prepared by subjecting the compound (XV) or a salt thereof to elimination reaction of the carboxy-protecting group.

This reaction can be carried out in a similar manner to the reaction in the aforementioned Process (B), and therefore the reagents to be used and reaction conditions (e.g., solvent, reaction temperature, etc.) can be referred to those of Process (B).

Process (I)

The compound (XVI) or a salt thereof can be prepared by reacting the compound (IX): or its reactive derivative at the carboxy group, or a salt thereof with the compound (XIV) or its reactive derivative at the amino group, or a salt thereof.

This reaction can be carried out in a similar manner to the reaction in the aforementioned Process (1), and therefore the reagents to be used and reaction conditions: (e.g., solvent, reaction temperature, etc.) can be referred to those of Process (1).

Process (J)

The compound (XVII) or a salt thereof can be prepared by subjecting the compound (XVI) or a salt thereof to elimination reaction of the amino-protecting group.

This reaction can be carried out in a similar manner to the reaction in the aforementioned Process (B), and therefore the reagents to be used and reaction conditions (e.g., solvent, reaction temperature, etc.) can be referred to those of Process (B).

Process (K)

The compound (XV) or a salt thereof can be prepared by reacting the compound (II) or its reactive derivative at the carboxy group, or a salt thereof with the compound (XVII) or its reactive derivative at the amino group, or a salt thereof.

This reaction can be carried out in a similar manner to the reaction in the aforementioned Process (1), and therefore the reagents to be used and reaction conditions (e.g., solvent, reaction temperature, etc.) can be referred to those of Process (1).

Suitable salts of the starting compounds and their reactive derivatives in Processes (1) and (2) and Processes (A) to (K) can be referred to the ones as exemplified for the compound (I).

The compounds obtained by the above process can be isolated and purified by a conventional method such as pulverization, recrystallization, column chromatography, reprecipitation, or the like.

It is to be noted that the compound (I) and the other compounds may include one or more stereoisomer(s) such as optical isomer(s) and geometrical isomer(s) due to asymmetric carbon atom(s) and double bond(s), and all of such isomers and mixtures thereof are included within the scope of this invention.

The object compounds (I) and pharmaceutically acceptable salts thereof include solvates [e.g., enclosure compounds (e.g., hydrate, etc.)].

The object compounds (I) and pharmaceutically acceptable salts thereof possess a strong inhibitory activity on the production of nitric oxide (NO).

Accordingly, the object compounds (I) and pharmaceutically acceptable salts thereof are expected to possess a nitric oxide synthase (NOS)-inhibitory activity or a NOS-production inhibitory activity.

Accordingly, the object compounds (I) and pharmaceutically acceptable salts thereof are useful for prevention and/or treatment of NO-mediated diseases in human being and animals, including respiratory diseases such as adult respiratory distress syndrome (ARDS) and asthma; cardiovascular diseases such as cardiovascular ischemia, myocarditis, heart failure, hypotension and atherosclerosis; endocrine diseases such as diabetes (e.g., insulin-dependent diabetes mellitus, etc.), complications of diabetes mellitus (e.g., diabetic nephropathy, diabetic retinopathy, diabetic neuropathy, etc.) and gout; renal diseases such as glomerulonephritis and renal failure; gastrointestinal diseases such as peptic ulcer and inflammatory bowel disease (e.g., ulcerative colitis, chronic colitis, etc.); pancreatic diseases such as pancreatitis; hepatic diseases such as hepatitis and liver cirrhosis; diseases of bone or joint such as synovitis, arthritis, osteoarthritis, osteoporosis; autoimmune diseases such as rheumatoid arthritis, systemic lupus erythematosus and multiple sclerosis; dermal diseases such as dermatitis and eczema; cancer such as solid tumors and metastasis; rejection by organ transplantation; shock (e.g., septic shock, etc.); and sepsis-induced systemic inflammatory response syndrome.

The object compounds (I) and pharmaceutically acceptable salts thereof are also useful for prevention and/or treatment of NO-mediated nervous diseases including central nervous system diseases such as CNS disorders, cerebrovascular diseases (e.g., cerebral infarction, cerebral ischemia, cerebral hemorrhage, etc.), migraine, Alzheimer's disease; peripheral nervous system diseases such as neuritis, pain (e.g., postherpetic neuralgia, reflex sympathetic dystrophy (RSD), causalgia, deafferentation pain syndrome, neuropathic pain, etc.), allodynia, hyperalgesia, neurological disorders and neuroprotection; Parkinson's disease; and amyotrophic lateral sclerosis.

Additionally, the object compounds (I) and pharmaceutically acceptable salts thereof are useful for treatment of sexual dysfunction such as male sexual dysfunction including erectile dysfunction, and female sexual dysfunction including orgasmic dysfunction related to clitoral disturbances.

Further, the object compounds (I) and pharmaceutically acceptable salts thereof are useful for prevention and/or treatment of NO-mediated ophthalmic diseases, including conjunctive diseases such as conjunctivitis (e.g., allergic conjunctivitis, vernal conjunctivitis, keratoconjunctivitis sicca, viral conjunctivitis, bacterial conjunctivitis, etc.); uveal diseases such as uveitis (e.g., Behcet disease, Harada disease, sympathetic ophthalmia, sarcoidosis, diabetic iritis, etc.); scleral diseases such as scleritis; corneal diseases such as corneal neovascularization, keratitis, corneal edema, corneal opacity, corneal dystrophy, keratoconus and neuroparalytic keratitis; retinal, vitreous diseases such as diabetic retinopathy, retinal artery occlusion, retinal vein occlusion, central serous chorioretinopathy, central hemorrhagic chorioretinitis, macular degeneration (e.g., age-related macular degeneration, etc.), retinal detachment, retinal pigmentary degeneration, macular neovascularization, macular hole, proliferative vitreoretinopathy, vitreous hemorrhage and vitreous opacity; lens diseases such as cataract (e.g., senile cataract, traumatic cataract, diabetic cataract, atopic cataract, etc.); glaucoma such as primary open-angle glaucoma, primary angle-closure glaucoma, normal tension glaucoma and neovascular glaucoma; ocular-hypertension; vision disorders such as amblyopia, color vision defect and night blindness; refractive errors such as astigmatism, hyperopia, myopia and presbyopia; and lacrimal apparatus diseases such as dry eye syndromes, lacrimal duct obstruction and dacryocystitis.

In order to illustrate the usefulness of the object compound (I), the pharmacological test result of the compound (I) is shown in the following.

Test Compound:

Compound (a): 5-Chloro-N-[(1S)-2-oxo-2-({2-oxo-2-[4-(1,3-thiazol-2-yloxy)-1-piperidinyl]ethyl}amino)-1-(2-pyridylmethyl)ethyl]-1-benzofuran-2-carboxamide Compound (b): (2E)-3-(4-Chlorophenyl)-N-[(1S)-2-oxo-2-({2-oxo-2-[4-(2-pyrazinyloxy)-1-piperidinyl]ethyl}amino)-1-(2-pyridylmethyl)ethyl]acrylamide Compound (c): 5-Chloro-N-[(1S)-2-[(2-{4-[(6-methoxy-2-pyridyl)oxy]-1-piperidinyl}-2-oxoethyl)amino]-2-oxo-1-(2-pyridylmethyl)ethyl]-1-benzofuran-2-carboxamide Compound (d): 5-Chloro-N-[(1S)-2-oxo-2-({2-oxo-2-[4-(2-pyridyloxy)-1-piperidinyl]ethyl}amino)-1-(2-pyridylmethyl)ethyl]-1-benzofuran-2-carboxamide Compound (e): (2E)-3-(4-Chlorophenyl)-N-[(1S)-2-oxo-2-{[2-oxo-2-(4-phenoxy-1-piperidinyl)ethyl]amino}-1-(2-pyridylmethyl)ethyl]-acrylamide Compound (f): 5-Chloro-N-[(1S)-2-oxo-2-({2-oxo-2-[4-(2,2,2-trifluoroethoxy)-1-piperidinyl]ethyl}amino)-1-(2-pyridylmethyl)-ethyl]-1-benzofuran-2-carboxamide Compound (g): (2E)-3-(4-Chlorophenyl)-N-[(1S)-2-{[2-(4-isopropoxy-1-piperidinyl)-2-oxoethyl]amino}-2-oxo-1-(2-pyridylmethyl)ethyl]acrylamide Test 1: Assay for Inhibitory Activity on the Production of Nitric Oxide The murine macrophage cell line RAW264.7 (American Type Culture Collection, No. TIB71) was used in this study. RAW264.7 cells were grown on F75 plastic culture flasks at 37° C., 5% in Dulbecco's modified Eagle's medium (DMEM) supplemented with L-glutamine, penicillin, streptomycin and 10% heat-inactivated fetal bovine serum. They were removed from culture flasks by rubber cell scraper and were centrifuged and resuspended in DEM without phenol red. They were plated in 96-well microtiter plates ($10^5$ cells per well) and allowed to adhere over 2 hours. The test samples were added and the cells were preincubated for 1 hour. Thereafter the cells were activated with both of lipopolysaccharide (LPS) (1 µg/ml) and interferon γ (INF γ) (3 u/ml) for 18–24 hours. An equal volume of Griess reagent (1% sulfanilamide/0.1% N-naphthylethylenediamine dihydrochloride/2.5% $H_3PO_4$) was added and the cells were incubated at room temperature for 10 minutes. The absorbance was read at 570 nm using microplate reader and $NO_2^-$ was measured using $NaNO_2$ as a standard.

Test result:

TABLE 1

| Test compound ($10^{-6}$ M) | Inhibition (%) |
| --- | --- |
| (a) | 100 |
| (b) | 97.6 |
| (c) | 100 |
| (d) | 100 |
| (e) | 100 |
| (f) | 100 |
| (g) | 100 |

Test 2: Protective Effect of the Compound (I) Combined with FK506 On Rat Cardiac Allograft Method:

Experiments were performed on male Lewis and ACI rats weighing 175–200 g. Rats were anesthetized with sodium pentobarbital (50 mg/kg, i.p.), and underwent allogeneic (Lewis donor to ACI recipient) heterotopic cardiac transplantation. Experimental groups were divided into single-drug group and combined-drug group. Single-drug dose of FK506, which was prepared in a manner similar to that disclosed in EP-0184162, was 0.32 mg/kg. Combined-drug dose was FK506 (0.32 mg/kg)+ the compound (I) (10 mg/kg). The grafted hearts were monitored by daily palpation where complete rejection was defined as the cessation of palpable contractile activity. Each drug was suspended in a solution of 0.5% methylcellulose, and administered by daily gastric intubation in a volume of 5 ml/kg of body weight for 14 days.

The combination of the compound (I) and FK506 dramatically prolonged the graft survival.

The above experimental results indicate that the activity and/or efficacy of an immunosuppressant in rejection of transplantation can be remarkably and synergistically increased by administering compound (I) in combination, which has a strong inhibitory activity on the production of nitric oxide.

For therapeutic administration, the object compound (I) of the present invention and pharmaceutically acceptable salts thereof are used in the form of a conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee, suppository or ointment, or in a liquid form such as solution, suspension or emulsion for injection, intravenous drip, ingestion, eye drop, etc. If needed, there may be included in the above preparation auxiliary substance such as stabilizing agent, wetting or emulsifying agent, buffer or any other commonly used additives.

The effective ingredient may usually be administered in a unit dose of 0.001 mg/kg to 500 mg/kg, preferably 0.01 mg/kg to 10 mg/kg, 1 to 4 times a day. However, the above dosage may be increased or decreased according to age, body weight and conditions of the patient or administering method.

According to the present invention, a pharmaceutical composition comprising FK506 and the compound (I) or a pharmaceutically acceptable salt thereof is provided. A pharmaceutical composition comprising FK506 and the compound (I) or a pharmaceutically acceptable salt thereof is useful as an immunosuppressant. For example, the pharmaceutical composition of the present invention is useful as a medicament for the prevention or treatment of rejection by organ transplantation.

When the compound (I) is used in combination with FK506, a ratio by weight of the compound (I) or a pharmaceutically acceptable salt thereof to FK506 is in the range of 0.1/1–1000/1, preferably in the range of 1/1–100/1.

The preferred embodiments of the compound of the present invention represented by the general formula (I) are as follows.

(1) The compound of the formula (I), wherein $R^2$ is a group of the formula: —Y—$R^3$ wherein $R^3$ is lower alkyl, halo(lower)alkyl, optionally substituted heterocyclic group or optionally substituted aryl, and Y is —O—, —S— or —$SO_2$—, or a pharmaceutically acceptable salt thereof.

(2) The compound of (1) mentioned above, wherein $R^3$ is lower alkyl; halo(lower)alkyl; heterocyclic group optionally substituted by one or more substituent(s) selected from the group consisting of lower alkyl, lower alkoxy, halogen and halo(lower)alkyl; or aryl optionally substituted by one or more substituent(s) selected from the group consisting of lower alkyl, lower alkoxy, halogen and halo(lower)alkyl, or a pharmaceutically acceptable salt thereof.

(3) The compound of (2) mentioned above, wherein $R^3$ is lower alkyl; halo(lower)alkyl; heterocyclic group selected from the group consisting of pyridyl, pyrazinyl, thiazolyl, pyridazinyl and pyrimidinyl, said heterocyclic group is optionally substituted by one or more substituent(s) selected from the group consisting of lower alkyl, lower alkoxy, halogen and halo(lower)alkyl; or phenyl optionally substituted by one or more substituent(s) selected from the group consisting of lower alkyl, lower alkoxy, halogen and halo(lower)alkyl, or a pharmaceutically acceptable salt thereof.

(4) The compound of the formula (I), wherein X is

or a pharmaceutically acceptable salt thereof.

(5) The compound of (4) mentioned above, wherein $R^2$ is substituted hydroxy, or a pharmaceutically acceptable salt thereof.

(6) The compound of (5) mentioned above, wherein $R^2$ is a group of the formula: —O—$R^3$ wherein $R^3$ is lower alkyl, halo(lower)alkyl, optionally substituted-heterocyclic group or optionally substituted aryl, or a pharmaceutically acceptable salt thereof.

(7) The compound of (6) mentioned above, wherein $R^3$ is lower alkyl, halo(lower)alkyl, pyridyl, pyrazinyl, thiazolyl or phenyl, each of said pyridyl, pyrazinyl, thiazolyl and phenyl is optionally substituted by one or more substituents selected from the group consisting of lower alkyl, lower alkoxy, halogen and halo(lower)alkyl, or a pharmaceutically acceptable salt thereof.

(8) The compound of (7) mentioned above, wherein $R^3$ is lower alkyl, halo(lower)alkyl, pyridyl, pyrazinyl, thiazolyl or phenyl, said pyridyl is optionally substituted by a substituent selected from the group consisting of lower alkyl, lower alkoxy, halogen and halo(lower)alkyl, or a pharmaceutically acceptable salt thereof.

(9) The compound of the formula (I), wherein $R^1$ is benzofuranyl substituted by chlorine, or styryl substituted by chlorine, or a pharmaceutically acceptable salt thereof.

(10) The compound of the formula (I), wherein $R^1$ is 5-chloro-1-benzofuran-2-yl or 2-(4-chlorophenyl)ethenyl, or a pharmaceutically acceptable salt thereof.

The following Preparations and Examples are given for the purpose of illustrating the present invention in detail.

Preparation 1
Benzyl({(2S)-2-[(tert-butoxycarbonyl)amino]-3-(2-pyridyl)propanoyl}amino)acetate To a solution of (2S)-2-[(tert-butoxycarbonyl)amino]-3-(2-pyridyl)propanoic acid (55.0 g), glycine benzyl ester tosylate (69.7 g), and diphenylphosphoryl azide (46.7 ml) in N,N-dimethylformamide (550 ml) was added dropwise N,N-diisopropylethylamine (75.6 ml) at 4° C. The mixture was warmed to room temperature and stirred for 3 hours. The resulting mixture was poured into ice-cold saturated aqueous sodium hydrogencarbonate solution (700 ml). The mixture was extracted twice with ethyl acetate (total 1.3 L) and washed successively with water (400 ml×2), saturated aqueous ammonium chloride solution (200 ml), aqueous sodium hydrogencarbonate solution (300 ml×2), and brine (40 ml). The organic layer was dried over anhydrous magnesium sulfate and concentrated to give the title compound (77.4 g) as pale brown crystals.

ESI-MS: 414.3(M+H) $^1$H-NMR (300 MHz, CDCl$_3$) δ 8.48(dd, J=5,2 Hz, 1H), 7.82(br, 1H), 7.60(td, J=8,2 Hz, 1H), 7.40–7.29(m, 5H), 7.21(d, J=8 Hz, 1H), 7.14(dd, J=8,5 Hz, 1H), 6.33(br, 1H), 5.15(s, 2H), 4.62(br, 1H), 4.04(d, J=6 Hz, 2H), 3.36–3.18(m, 2H), 1.43(s, 9H).

Preparation 2
Benzyl {[(2S)-2-amino-3-(2-pyridyl)propanoyl]amino}acetate dihydrochloride To a solution of benzyl({(2S)-2-[(tert-butoxycarbonyl)amino]-3-(2-pyridyl)propanoyl}amino)acetate (73.8 g) in ethyl acetate (150 ml) was added dropwise 4N hydrogen chloride in ethyl acetate (669 ml) at 10° C. over 30 minutes. The mixture was warmed to room temperature and stirred for 3 hours. The mixture was diluted with ethyl acetate (300 ml). The resulting precipitate was collected by filtration, washed with ethyl acetate (700 ml), and dried in vacuo to give the title compound.

$^1$H-NMR (300 MHz, DMSO-d$_6$) δ 9.31(t, J=6 Hz, 1H), 8.83(d, J=5 Hz, 1H), 8.70(br, 3H), 8.40(t, J=8 Hz, 1H), 7.96(d, J=8 Hz, 1H), 7.87(t, J=5 Hz, 1H), 7.41–7.30(m, 5H), 5.14(s, 2H), 4.53(br, 1H), 4.05(dd, J=18,6 Hz, 1H), 3.99(dd, J=18,6 Hz, 1H), 3.64(dd, J=15,5 Hz, 1H), 3.54(dd, J=15,8 Hz, 1H).

Preparation 3
Benzyl {[(2S)-2-{[(2E)-3-(4-chlorophenyl)-2-propenoyl]-amino}-3-(2-pyridyl)propanoyl]amino}acetate To a solution of 4-chlorocinnamic acid (49.2 g) in dichloromethane (400 ml) were added oxalyl chloride (30.5 ml) and 1 drop of N,N-dimethylformamide, and the mixture was stirred at room temperature for 6 hours. The reaction mixture was evaporated to dryness, and the residual acid chloride was dissolved in dichloromethane (900 ml). To this solution was added benzyl {[(2S)-2-amino-3-(2-pyridyl)propanoyl]amino}acetate dihydrochloride (104 g) at 10° C. followed by addition of triethylamine (116 ml) over 40 minutes. The mixture was allowed to warm to room temperature and stirred for 2 hours. The reaction mixture was evaporated to dryness, and the residue was washed successively with water (500 ml×5) and tetrahydrofuran-n-hexane (1:2, 500 ml×10), and dried in vacuo to give the title compound (115 g) as a white solid.

ESI-MS: 478.3(M+H) $^1$H-NMR (300 MHz, CDCl$_3$) δ 8.51(dd, J=5,2 Hz, 1H), 8.27(t, J=5 Hz, 1H), 7.83(d, J=6 Hz, 1H), 7.64(td, J=8,2 Hz, 1H), 7.57(d, J=16 Hz, 1H), 7.44(d, J=9 Hz, 2H), 7.39–7.28(m, 8H), 7.19(dd, J=8,5 Hz, 1H), 6.47(d, J=16 Hz, 1H), 5.14(s, 2H), 4.98(app q, J=6 Hz, 1H), 4.07(d, J=5 Hz, 2H), 3.36(dd, J=15,5 Hz, 1H), 3.26(dd, J=15,6 Hz, 1H).

Preparation 4
{[(2S)-2-{[(2E)-3-(4-Chlorophenyl)-2-propenoyl]amino}-3-(2-pyridyl)propanoyl]amino}acetic acid To a suspension of benzyl {[(2S)-2-{[(2E)-3-(4-chlorophenyl)-2-propenoyl]amino}-3-(2-pyridyl)propanoyl]amino}-acetate (10.8 g) in methanol (200 ml) was added 1N aqueous sodium hydroxide solution (22.6 ml), and the mixture was stirred at room temperature for 5 hours. The reaction mixture was concentrated in vacuo, and the residue was treated with aqueous citric acid solution (10%, 100 ml). The resulting white precipitate was collected by filtration, washed with tetrahydrofuran-hexane (1:1, 150 ml), and dried in vacuo to give the title compound (8.25 g) as a white solid.

ESI-MS: 388.2(M+H) $^1$H-NMR (300 MHz, DMSO-$d_6$) δ 12.6(br, 1H), 8.50–8.36(m, 3H), 7.68(td, J=8,2 Hz, 1H), 7.56(d, J=9 Hz, 2H), 7.47(d, J=9 Hz, 2H), 7.34(d, J=16 Hz, 1H), 7.30(d, J=8 Hz, 1H), 7.20(dd, J=8,5 Hz, 1H), 6.68(d, J=16 Hz, 1H), 4.96–4.86(m, 1H), 3.78(dd, J=18,6 Hz, 1H), 3.74(dd, J=18,6 Hz, 1H), 3.24(dd, J=14,5 Hz, 1H), 2.99(dd, J=14,10 Hz, 1H).

Preparation 5

Benzyl {[(2S)-2-{[(5-chloro-1-benzofuran-2-yl)carbonyl]-amino }-3-(2-pyridyl)propanoyl]amino}acetate The title compound was obtained from benzyl {[(2S)-2-amino-3-(2-pyridyl)propanoyl]amino}acetate dihydrochloride and 5-chloro-1-benzofuran-2-carboxylic acid in the same manner as in Preparation 3.

ESI-MS: 492.3(M+H) $^1$H-NMR (300 MHz, CDCl$_3$) δ 8.70–8.49(m, 3H), 7.71–7.62(m, 2H), 7.52–7.18(m, 10H), 5.16(s, 2H), 5.11–5.02(m, 1H), 4.19–4.03(m, 2H), 3.44(dd, J=15,4 Hz, 1H), 3.35(dd, J=15,7 Hz, 1H).

Preparation 6

{[(2S)-2-{[(5-Chloro-1-benzofuran-2-yl)carbonyl]amino}-3-(2-pyridyl)propanoyl]amino}acetic acid The title compound was obtained from benzyl {[(2S)-2-{[(5-chloro-1-benzofuran-2-yl)carbonyl]amino}-3-(2-pyridyl)propanoyl]-amino}acetate in the same manner as in Preparation 4.

ESI-MS: 402.2(M+H) $^1$H-NMR (300 MHz, DMSO-$d_6$) δ 12.6(br, 1H), 9.00(d, J=8 Hz, 1H), 8.49(dd, J=5,2 Hz, 1H), 8.46(t, J=6 Hz, 1H), 7.88(d, J=2 Hz, 1H), 7.72(d, J=9 Hz, 1H), 7.67(td, J=8,2 Hz, 1H), 7.53(d, J=1 Hz, 1H), 7.48(dd, J=9,2 Hz, 1H), 7.33(d, J=8 Hz, 1H), 7.20(dd, J=8,5 Hz, 1H), 5.04–4.94(m, 1H), 3.80(dd, J=18,6 Hz, 1H), 3.74(dd, J=18,6 Hz, 1H), 3.32(dd, J=14,4 Hz, 1H), 3.22(dd, J=14,10 Hz, 1H).

Preparation 7 tert-Butyl 4-(1,3-thiazol-2-yloxy)-1-piperidinecarboxylate

To a slurry of sodium hydride (about 60% oil suspension, 5.67 g) in dimethoxyethane (40 ml) was added a solution of tert-butyl 4-hydroxy-1-piperidinecarboxylate (23.9 g) in dimethoxyethane (60 ml) over 30 minutes, and the mixture was stirred for an additional 1 hour. To the mixture was added 2-bromothiazole (15.0 g), and the mixture was refluxed for 4 hours. After cooling, the resulting pale brown suspension was diluted with ether (300 ml) and the mixture was filtered through a pad of Celite. The filtrate was washed with brine, dried over anhydrous magnesium sulfate, and concentrated in vacuo. The residual oil was purified by silica gel column chromatography (eluent; 15% ethyl acetate in n-hexane) to give the title compound (22.1 g) as a yellow oil.

ESI-MS: 285.2(M+H) $^1$H-NMR (300 MHz, CDCl$_3$) δ 7.11(d, J=4 Hz, 1H), 6.67(d, J=4 Hz, 1H), 5.13(septet, J=4 Hz, 1H), 3.73(ddd, J=14,7,4 Hz, 2H), 3.32(ddd, J=14,8,4 Hz, 2H), 2.08–1.96(m, 2H), 1.88–1.74(m, 2H), 1.47(s, 9H).

EXAMPLE 1

(2E)-3-(4-Chlorophenyl)-N-[(1S)-2-oxo-2-({2-oxo-2-[4-(1,3-thiazol-2-yloxy)-1-piperidinyl]ethyl}amino)-1-(2-pyridylmethyl)-ethyl]acrylamide To a solution of tert-butyl 4-(1,3-thiazol-2-yloxy)-1-piperidinecarboxylate (2.93 g) in ethyl acetate (12 ml) was added dropwise 4N hydrogen chloride in ethyl acetate (15 ml) at 10° C. The mixture was warmed to room temperature and stirred for 1 hour. The mixture was concentrated and dried in vacuo. The residual yellow solid was added to an ice-cold mixture of {[(2S)-2-{[(2E)-3-(4-chlorophenyl)-2-propenoyl]amino}-3-(2-pyridyl)propanoyl]-amino}acetic acid (4.0 g), 1-hydroxybenzotriazole (1.53 g), and 1-(3-dimethylaminopropyl)-3-ethylcarbodiimide hydrochloride (2.17 g) in N,N-dimethylformamide (40 ml). To the mixture was added dropwise N,N-diisopropylethylamine (3.9 ml). The mixture was warmed to room temperature and stirred for 2 hours. The resulting mixture was poured into ice-cold saturated aqueous sodium hydrogencarbonate solution (200 ml). The mixture was extracted three times with ethyl acetate (total 400 ml) and washed successively with saturated aqueous ammonium chloride solution (100 ml), water (70 ml×3), and brine (20 ml). The organic layer was dried over anhydrous magnesium sulfate and concentrated. The residue was purified by silica gel column chromatography (eluent; 1% methanol in chloroform) to give the title compound (4.57 g) as a pale yellow solid, which was recrystallized from ethyl acetate.

ESI-MS: 554.2(M+H) $^1$H-NMR (300 MHz, CDCl$_3$) δ 8.55(dd, J=5,2 Hz, 1H), 8.04–7.97(m, 1H), 7.96–7.88(m, 1H), 7.63(td, J=8,2 Hz, 1H), 7.60(d, J=16 Hz, 1H), 7.45(d, J=9 Hz, 2H), 7.34(d, J=9 Hz, 2H), 7.25(d, J=8 Hz, 1H), 7.18(dd, J=8,5 Hz, 1H), 7.10(d, J=4 Hz, 1H), 6.68(d, J=4 Hz, 1H), 6.50(d, J=16 Hz, 1H), 5.25–5.15(br m, 1H), 5.06–4.99 (m, 1H), 4.03(d, J=4 Hz, 2H), 3.83–3.52(m, 3H), 3.43(dd, J=15,5 Hz, 1H), 3.37–3.31(m, 1H), 3.26(dd, J=15,6 Hz, 1H), 2.08–1.81(m, 4H).

EXAMPLE 2

5-Chloro-N-[(1S)-2-oxo-2-({2-oxo-2-[4-(1,3-thiazol-2-yloxy)-1-piperidinyl]ethyl}amino)-1-(2-pyridylmethyl)ethyl]-1-benzofuran-2-carboxamide The title compound was obtained from tert-butyl 4-(1,3-thiazol-2-yloxy)-1-piperidinecarboxylate and {[(2S)-2-{[(5-chloro-1-benzofuran-2-yl)carbonyl]amino}-3-(2-pyridyl)propanoyl]-amino}acetic acid in the same manner as in Example 1.

ESI-MS: 568.3(M+H) $^1$H-NMR (300 MHz, CDCl$_3$) δ 8.80–8.72(m, 1H), 8.62(d, J=5,2 Hz, 1H), 8.19–8.11(m, 1H), 7.65(td, J=8,2 Hz, 1H), 7.65(d, J=2 Hz, 1H), 7.49(d, J=9 Hz, 1H), 7.42(s, 1H), 7.39(dd, J=9,2 Hz, 1H), 7.27(d, J=8 Hz, 1H), 7.20(dd, J=8,5 Hz, 1H), 7.10(d, J=4 Hz, 1H), 6.68(d, J=4 Hz, 1H), 5.25–5.16(m, 1H), 5.15–5.07(m, 1H), 4.07(d, J=4 Hz, 2H), 3.83–3.53(m, 3H), 3.48(dd, J=15,5 Hz, 1H), 3.40–3.29(m, 2H), 2.08–1.81(m, 4H).

Preparation 8 tert-Butyl 4-(2-pyrazinyloxy)-1-piperidinecarboxylate

To a slurry of sodium hydride (about 60% oil suspension, 114 mg) in dimethyl sulfoxide (5 ml) was added dropwise tert-butyl 4-hydroxy-1-piperidinecarboxylate (576 mg). Considerable foaming occurred and the solution turned pale orange. To this solution was added chloropyrazine (377 mg) and the mixture was stirred at room temperature for 12 hours. The resulting mixture was partitioned between saturated aqueous sodium hydrogencarbonate solution and ethyl acetate. The organic layer was washed with water and brine, dried over anhydrous magnesium sulfate, and concentrated in vacuo. The residual solid was triturated with a mixture of ethyl acetate and n-hexane to give the title compound (472 mg) as white crystals.

ESI-MS: 280.2(M+H) $^1$H-NMR (300 MHz, CDCl$_3$) δ 8.20(d, J=1 Hz, 1H), 8.10(d, J=3 Hz, 1H), 8.05(dd, J=3,1 Hz,

1H), 5.20(septet, J=4 Hz, 1H), 3.84–3.72(m, 2H), 3.30(ddd, J=14,8,4 Hz, 2H), 2.05–1.93(m, 2H), 1.81–1.68(m, 2H), 1.48(s, 9H).

EXAMPLE 3

(2E)-3-(4-Chlorophenyl)-N-[(1S)-2-oxo-2-({2-oxo-2-[4-(2-pyrazinyloxy)-1-piperidinyl]ethyl}amino)-1-(2-pyridylmethyl)-ethyl]acrylamide The title compound was obtained from tert-butyl 4-(2-pyrazinyloxy)-1-piperidinecarboxylate and {[(2S)-2-{[(2E)-3-(4-chlorophenyl)-2-propenoyl]amino}-3-(2-pyridyl)propanoyl]amino}-acetic acid in the same manner as in Example 1.

ESI-MS: 549.4(M+H) $^1$H-NMR (300 MHz, CDCl$_3$) δ 8.56(dd, J=5,2 Hz, 1H), 8.22–8.20(m, 1H), 8.13(d, J=3 Hz, 1H), 8.05(dd, J=3,1 Hz, 1H), 8.03–7.88(m, 2H), 7.64(td, J=8,2 Hz, 1H), 7.61(d, J=16 Hz, 1H), 7.46(d, J=8 Hz, 2H), 7.35(d, J=8 Hz, 2H), 7.27(d, J=8 Hz, 1H), 7.19(dd, J=8,5 Hz, 1H), 6.50(d, J=16 Hz, 1H), 5.33–5.22(m, 1H), 5.07–4.99(m, 1H), 4.05(app d, J=4 Hz, 2H), 3.92–3.78(m, 1H), 3.68–3.52(m, 2H), 3.48–3.22(m, 3H), 2.07–1.92(m, 2H), 1.88–1.78(m, 2H).

EXAMPLE 4

5-Chloro-N-[(1S)-2-oxo-2-({2-oxo-2-[4-(2-pyrazinyloxy)-1-piperidinyl]ethyl}amino)-1-(2-pyridylmethyl)ethyl]-1-benzofuran-2-carboxamide The title compound was obtained from tert-butyl 4-(2-pyrazinyloxy)-1-piperidinecarboxylate and {[(2S)-2-{[(5-chloro-1-benzofuran-2-yl)carbonyl]amino}-3-(2-pyridyl)propanoyl]amino}-acetic acid in the same manner as in Example 1.

ESI-MS: 563.2(M+H) $^1$H-NMR (300 MHz, CDCl$_3$) δ 8.81–8.71(m, 1H), 8.62(dd, J=5,2 Hz, 1H), 8.22–8.14(m, 2H), 8.13(d, J=3 Hz, 1H), 8.05(dd, J=3,1 Hz, 1H), 7.65(td, J=8,2 Hz, 1H), 7.65(d, J=2 Hz, 1H), 7.49(dd, J=9,1 Hz, 1H), 7.43(d, J=1 Hz, 1H), 7.39(dd, J=9,2 Hz, 1H), 7.27(d, J=8 Hz, 1H), 7.20(dd, J=8,5 Hz, 1H), 5.32–5.21(m, 1H), 5.16–5.06(m, 1H), 4.15–4.00(m, 2H), 3.92–3.76(m, 1H), 3.69–3.54(m, 2H), 3.49(dd, J=15,5 Hz, 1H), 3.40–3.28(m, 2H), 2.07–1.90(m, 2H), 1.89–1.74(m, 2H).

Preparation 9 tert-Butyl 4-(4-pyridyloxy)-1-piperidinecarboxylate

The title compound was obtained from tert-butyl 4-hydroxy-1-piperidinecarboxylate and 4-chloropyridine hydrochloride in the same manner as in Preparation 8.

ESI-MS: 279.2(M+H) $^1$H-NMR (300 MHz, CDCl$_3$) δ 8.42(d, J=6 Hz, 2H), 6.80(d, J=6 Hz, 2H), 4.58(septet, J=4 Hz, 1H), 3.69(ddd, J=14,8,4 Hz, 2H), 3.37(ddd, J=14,8,4 Hz, 2H), 2.01–1.88(m, 2H), 1.84–1.69(m, 2H), 1.47(s, 9H).

EXAMPLE 5

(2E)-3-(4-Chlorophenyl)-N-[(1S)-2-oxo-2-({2-oxo-2-[4-(4-pyridyloxy)-1-piperidinyl]ethyl}amino)-1-(2-pyridylmethyl)ethyl]-acrylamide The title compound was obtained from tert-butyl 4-(4-pyridyloxy)-1-piperidinecarboxylate and {[(2S)-2-{[(2E)-3-(4-chlorophenyl)-2-propenoyl]amino}-3-(2-pyridyl)propanoyl]amino}-acetic acid in the same manner as in Example 1.

ESI-MS: 548.3(M+H) $^1$H-NMR (300 MHz, CDCl$_3$) δ 8.55(dd, J=5,2 Hz, 1H), 8.43(dd, J=5,2 Hz, 1H), 8.04–7.86 (m, 2H), 7.64(td, J=8,2 Hz, 1H), 7.60(d, J=16 Hz, 1H), 7.45(d, J=8 Hz, 2H), 7.35(d, J=8 Hz, 2H), 7.26(d, J=8 Hz, 1H), 7.18(dd, J=8,5 Hz, 1H), 6.79(dd, J=5,2 Hz, 2H), 6.50(d, J=16 Hz, 1H), 5.06–4.98(m, 1H), 4.70–4.62(m, 1H), 4.12–3.96(m, 2H), 3.84–3.22(m, 6H), 1.98–1.79(m, 4H).

EXAMPLE 6

5-Chloro-N-[(1S)-2-oxo-2-({2-oxo-2-[4-(4-pyridyloxy)-1-piperidinyl]ethyl}amino)-1-(2-pyridylmethyl)ethyl]-1-benzofuran-2-carboxamide The title compound was obtained from tert-butyl 4-(4-pyridyloxy)-1-piperidinecarboxylate and {[(2S)-2-{[(5-chloro-1-benzofuran-2-yl)carbonyl]amino}-3-(2-pyridyl)propanoyl]amino}-acetic acid in the same manner as in Example 1.

ESI-MS: 562.3(M+H) $^1$H-NMR (300 MHz, CDCl$_3$) δ 8.83–8.71(m, 1H), 8.62(dd, J=5,2 Hz, 1H), 8.43(d, J=6 Hz, 2H), 8.22–8.12(m, 1H), 7.65(td, J=8,2 Hz, 1H), 7.65(d, J=2 Hz, 1H), 7.49(d, J=9 Hz, 1H), 7.42(s, 1H), 7.39(dd, J=9,2 Hz, 1H), 7.28(d, J=8 Hz, 1H), 7.20(dd, J=8,5 Hz, 1H), 6.79(d, J=6 Hz, 2H), 5.15–5.07(m, 1H), 4.71–4.62(m, 1H), 4.16–3.99(m, 2H), 3.83–3.29(m, 6H), 2.00–1.77(m, 4H).

Preparation 10 tert-Butyl 4-(3-pyridyloxy)-1-piperidinecarboxylate

The title compound was obtained from tert-butyl 4-hydroxy-1-piperidinecarboxylate and 3-fluoropyridine in the same manner as in Preparation 8.

ESI-MS: 279.2(M+H) $^1$H-NMR (300 MHz, CDCl$_3$) δ 8.33–8.30(m, 1H), 8.22(dd, J=4,3 Hz, 1H), 7.23–7.20(m, 2H), 4.51(septet, J=4 Hz, 1H), 3.71(ddd, J=14,7,4 Hz, 2H), 3.35(ddd, J=14,8,4 Hz, 2H), 2.00–1.88(m, 2H), 1.83–1.70(m, 2H), 1.47(s, 9H).

EXAMPLE 7

(2E)-3-(4-Chlorophenyl)-N-[(1S)-2-oxo-2-({2-oxo-2-[4-(3-pyridyloxy)-1-piperidinyl]ethyl}amino)-1-(2-pyridylmethyl)ethyl]-acrylamide The title compound was obtained from tert-butyl 4-(3-pyridyloxy)-1-piperidinecarboxylate and {[(2S)-2-{[(2E)-3-(4-chlorophenyl)-2-propenoyl]amino}-3-(2-pyridyl)propanoyl]amino}-acetic acid in the same manner as in Example 1.

ESI-MS: 548.3(M+H) $^1$H-NMR (300 MHz, CDCl$_3$) δ 8.56(dd, J=5,2 Hz, 1H), 8.33–8.30(m, 1H), 8.24(dd, J=4,1 Hz, 1H), 8.06–7.87(m, 2H), 7.64(td, J=8,2 Hz, 1H), 7.61(d, J=16 Hz, 1H), 7.46(d, J=8 Hz, 2H), 7.35(d, J=8 Hz, 2H), 7.29–7.16(m, 5H), 6.50(d, J=16 Hz, 1H), 5.06–4.99(m, 1H), 4.63–4.57(m, 1H), 4.13–3.97(m, 2H), 3.81–3.23(m, 6H), 1.99–1.81(m, 4H).

EXAMPLE 8

5-Chloro-N-[(1S)-2-oxo-2-({2-oxo-2-[4-(3-pyridyloxy)-1-piperidinyl]ethyl}amino)-1-(2-pyridylmethyl)ethyl]-1-benzofuran-2-carboxamide The title compound was obtained from tert-butyl 4-(3-pyridyloxy)-1-piperidinecarboxylate and {[(2S)-2-{[(5-chloro-1-benzofuran-2-yl)carbonyl]amino}-3-(2-pyridyl)propanoyl]amino}-acetic acid in the same manner as in Example 1.

ESI-MS: 562.3(M+H) $^1$H-NMR (300 MHz, CDCl$_3$) δ 8.83–8.70(m, 1H), 8.62(dd, J=5,2 Hz, 1H), 8.33–8.29(m, 1H), 8.25–8.22(m, 1H), 8.21–8.10(m, 1H), 7.65(td, J=8,2 Hz, 1H), 7.65(d, J=2 Hz, 1H), 7.49(d, J=9 Hz, 1H), 7.42(s, 1H), 7.39(dd, J=9,2 Hz, 1H), 7.30–7.16(m, 4H), 5.16–5.07(m, 1H), 4.64–4.55(m, 1H), 4.15–3.98(m, 2H), 3.80–3.28(m, 6H), 1.98–1.80(m, 4H).

Preparation 11 tert-Butyl 4-[(6-methoxy-2-pyridyl)oxy]-1-piperidinecarboxylate

The title compound was obtained from tert-butyl 4-hydroxy-1-piperidinecarboxylate and 2-chloro-6-methoxypyridine in the same manner as in Preparation 8.

ESI-MS: 309.2(M+H) $^1$H-NMR (300 MHz, CDCl$_3$) δ 7.49(t, J=8 Hz, 1H), 6.29(d, J=8 Hz, 2H), 5.17(septet, J=4 Hz, 1H), 3.88(s, 3H), 3.81–3.70(m, 2H), 3.31(ddd, J=14,8,4 Hz, 2H), 2.04–1.92(m, 2H), 1.82–1.67(m, 2H), 1.47(s, 9H).

EXAMPLE 9

(2E)-3-(4-Chlorophenyl)-N-[(1S)-2-[(2-{4-[(6-methoxy-2-pyridyl)oxy]-1-piperidinyl}-2-oxoethyl)amino]-2-oxo-1-(2-pyridylmethyl)ethyl]acrylamide The title compound was obtained from tert-butyl 4-[(6-methoxy-2-pyridyl)oxy]-1-piperidinecarboxylate and {[(2S)-2-{[(2E)-3-(4-chlorophenyl)-2-propenoyl]amino}-3-(2-pyridyl)-propanoyl]amino}acetic acid in the same manner as in Example 1.

ESI-MS: 578.3(M+H) $^1$H-NMR (300 MHz, CDCl$_3$) δ 8.56(dd, J=5,2 Hz, 1H), 8.04–7.86(m, 2H), 7.63(td, J=8,2 Hz, 1H), 7.61(d, J=16 Hz, 1H), 7.53–7.42(m, 3H), 7.35(d, J=8 Hz, 2H), 7.26(d, J=8 Hz, 1H), 7.18(dd, J=8,5 Hz, 1H), 6.50(d, J=16 Hz, 1H), 6.29(d, J=8 Hz, 2H), 5.32–5.20(m, 1H), 5.06–4.98(m, 1H), 4.03(app d, J=4 Hz, 2H), 3.86(s, 3H), 3.82–3.21(m, 6H), 2.02–1.74(m, 4H).

EXAMPLE 10

5-Chloro-N-[(1S)-2-[(2-{4-[(6-methoxy-2-pyridyl)oxy]-1-piperidinyl}-2-oxoethyl)amino]-2-oxo-1-(2-pyridylmethyl)ethyl]-1-benzofuran-2-carboxamide The title compound was obtained from tert-butyl 4-[(6-methoxy-2-pyridyl)oxy]-1-piperidinecarboxylate and {[(2S)-2-{[(5-chloro-1-benzofuran-2-yl)carbonyl]amino}-3-(2-pyridyl)propanoyl]-amino}acetic acid in the same manner as in Example 1.

ESI-MS: 592.4(M+H) $^1$H-NMR (300 MHz, CDCl$_3$) δ 8.82–8.71(m, 1H), 8.62(dd, J=5,2 Hz, 1H), 8.19–8.09(m, 1H), 7.65(td, J=8,2 Hz, 1H), 7.65(d, J=2 Hz, 1H), 7.52–7.45 (m, 2H), 7.42(s, 1H), 7.38(dd, J=9,2 Hz, 1H), 7.27(d, J=8 Hz, 1H), 7.20(dd, J=8,5 Hz, 1H), 6.29(d, J=8 Hz, 2H), 5.31–5.21(m, 1H), 5.16–5.08(m, 1H), 4.07(app d, J=4 Hz, 2H), 3.86(s, 3H), 3.82–3.44(m, 4H), 3.40–3.28(m, 2H), 2.03–1.70(m, 4H).

Preparation 12 tert-Butyl 3-[(5-chloro-2-pyridyl)oxy]-1-piperidinecarboxylate

The title compound was obtained from tert-butyl 3-hydroxy-1-piperidinecarboxylate and 2,5-dichloropyridine in the same manner as in Preparation 8.

ESI-MS: 313.2(M+H) $^1$H-NMR (300 MHz, CDCl$_3$) δ 8.07(d, J=3 Hz, 1H), 7.52(dd, J=9,3 Hz, 1H), 6.66(d, J=9 Hz, 1H), 4.99(br s, 1H), 3.90–3.10(br m, 4H), 2.10–1.70(br m, 3H), 1.60–1.50(m, 1H), 1.34(br s, 9H).

EXAMPLE 11

(2E)-3-(4-Chlorophenyl)-N-[(1S)-2-[(2-{3-[(5-chloro-2-pyridyl)oxy]-1-piperidinyl}-2-oxoethyl)amino]-2-oxo-1-(2-pyridylmethyl)ethyl]acrylamide The title compound was obtained from tert-butyl 3-[(5-chloro-2-pyridyl)oxy]-1-piperidinecarboxylate and {[(2S)-2-{[(2E)-3-(4-chlorophenyl)-2-propenoyl]amino}-3-(2-pyridyl)-propanoyl]amino}acetic acid in the same manner as in Example 1.

ESI-MS: 582.3(M+H) $^1$H-NMR (300 MHz, CDCl$_3$) δ 8.58–8.51(m, 1H), 8.10–7.81(m, 3H), 7.66–7.41(m, 5H), 7.34(d, J=8 Hz, 2H), 7.25(d, J=8 Hz, 1H), 7.20–7.14(m, 1H), 6.69–6.60(m, 1H), 6.53–6.44(m, 1H), 5.10–4.96(m, 2H), 4.16–3.80(m, 2H), 3.77–3.20(m, 6H), 2.10–1.50(m, 4H).

EXAMPLE 12

5-Chloro-N-[(1S)-2-[(2-{3-[(5-chloro-2-pyridyl)oxy]-1-piperidinyl}-2-oxoethyl)amino]-2-oxo-1-(2-pyridylmethyl)ethyl]-1-benzofuran-2-carboxamide The title compound was obtained from tert-butyl 3-[(5-chloro-2-pyridyl)oxy]-1-piperidinecarboxylate and {[(2S)-2-{[(5-chloro-1-benzofuran-2-yl)carbonyl]amino}-3-(2-pyridyl)propanoyl]-amino}acetic acid in the same manner as in Example 1.

ESI-MS: 596.3(M+H) $^1$H-NMR (300 MHz, CDCl$_3$) δ 8.84–8.69(m, 1H), 8.65–8.58(m, 1H), 8.17–7.97(m, 2H), 7.68–7.60(m, 2H), 7.56–7.46(m, 2H), 7.43–7.36(m, 2H), 7.29–7.24(m, 1H), 7.23–7.16(m, 1H), 6.70–6.60(m, 1H), 5.15–4.98(m, 2H), 4.20–3.85(m, 2H), 3.76–3.27(m, 6H), 2.09–1.50(m, 4H).

Preparation 13 tert-Butyl 4-(2-pyridyloxy)-1-piperidinecarboxylate

To a solution of 2-hydroxypyridine (2.0 g), tert-butyl 4-hydroxy-1-piperidinecarboxylate (5.3 g) and triphenylphosphine (8.3 g) in tetrahydrofuran (63 ml) was slowly added diethyl azodicarboxylate (5.5 g) at 8° C., and the mixture was stirred at room temperature for 4 hours. The reaction mixture was concentrated in vacuo to give the crude product of the title compound and the crude product was purified by chromatography on silica gel.

$^1$H-NMR (300 MHz, CDCl$_3$) δ 8.16–8.10(m, 1H), 7.60–7.52(m, 1H), 6.88–6.81(m, 1H), 6.71(d, J=8 Hz, 1H), 5.27–5.17(m, 1H), 3.85–3.70(m, 2H), 3.35–3.23(m, 2H), 2.05–1.90(m, 2H), 1.80–1.65(m, 2H), 1.47(s, 9H).

EXAMPLE 13

(2E)-3-(4-Chlorophenyl)-N-[(1S)-2-oxo-2-({2-oxo-2-[4-(2-pyridyloxy)-1-piperidinyl]ethyl}amino)-1-(2-pyridylmethyl)ethyl]-acrylamide The title compound was obtained from tert-butyl 4-(2-pyridyloxy)-1-piperidinecarboxylate and {[(2S)-2-{[(2E)-3-(4-chlorophenyl)-2-propenoyl]amino}-3-(2-pyridyl)propanoyl]amino}-acetic acid in the same manner as in Example 1.

ESI-MS: m/z 548(M+1) $^1$H-NMR (300 MHz, CDCl$_3$) δ 8.55(d, J=5 Hz, 1H), 8.01(d, J=5 Hz, 1H), 8.04–7.85(m, 2H), 7.67–7.53(m, 3H), 7.45(d, J=8 Hz, 2H), 7.35(d, J=8 Hz, 2H), 7.28–7.15(m, 2H), 6.85(dd, J=8,8 Hz, 1H), 6.70(d, J=8 Hz, 1H), 6.50(d, J=16 Hz, 1H), 5.34–5.25(m, 1H), 5.06–4.98(m, 1H), 4.06–4.01(m, 2H), 3.91–3.77(m, 1H), 3.66–3.50(m, 2H), 3.48–3.20(m, 3H), 2.05–1.90(m, 2H), 1.86–1.71(m, 2H).

EXAMPLE 14

5-Chloro-N-[(1S)-2-oxo-2-({2-oxo-2-[4-(2-pyridyloxy)-1-piperidinyl]ethyl}amino)-1-(2-pyridylmethyl)ethyl]-1-benzofuran-2-carboxamide The title compound was obtained from tert-butyl 4-(2-pyridyloxy)-1-piperidinecarboxylate and {[(2S)-2-{[(5- chloro-1-benzofuran-2-yl)carbonyl]amino}-3-(2-pyridyl)propanoyl]amino}-acetic acid in the same manner as in Example 1.

ESI-MS: m/z 562(M+1) $^1$H-NMR (300 MHz, CDCl$_3$) δ 8.80–8.71(m, 1H), 8.62(d, J=5 Hz, 1H), 8.16–8.07(m, 2H), 7.68–7.52(m, 3H), 7.48(d, J=8 Hz, 1H), 7.40(d, J=8 Hz, 1H), 7.37(dd, J=2,8 Hz, 1H), 7.30–7.15(m, 2H), 6.85(dd, J=8,8 Hz, 1H), 6.70(d, J=8 Hz, 1H), 5.35–5.24(m, 1H), 5.15–5.07(m, 1H), 4.09–4.02(m, 2H), 3.90–3.71(m, 1H), 3.67–3.44(m, 3H), 3.39–3.26(m, 2H), 2.05–1.70(m, 4H).

Preparation 14 tert-Butyl 4-[(6-methyl-2-pyridyl)oxy]-1-piperidinecarboxylate

The title compound was obtained from tert-butyl 4-hydroxy-1-piperidinecarboxylate and 2-hydroxy-6-methylpyridine in the same manner as in Preparation 13.

$^1$H-NMR (300 MHz, CDCl$_3$) δ 7.44(dd, J=8,8 Hz, 1H), 6.68(d, J=8 Hz, 1H), 6.49(d, J=8 Hz, 1H), 5.26–5.16(m, 1H), 3.82–3.68(m, 2H), 3.35–3.24(m, 2H), 2.42(s, 3H), 2.02–1.90(m, 2H), 1.79–1.64(m, 2H), 1.47(s, 9H).

EXAMPLE 15

(2E)-3-(4-Chlorophenyl)-N-[(1S)-2-[(2-{4-[(6-methyl-2-pyridyl)oxy]-1-piperidinyl}-2-oxoethyl)amino]-2-oxo-1-(2-pyridylmethyl)ethyl]acrylamide The title compound was obtained from tert-butyl 4-[(6-methyl-2-pyridyl)oxy]-1-piperidinecarboxylate and {[(2S)-2-{[(2E)-3-(4-chlorophenyl)-2-propenoyl]amino}-3-(2-pyridyl)-propanoyl]amino}acetic acid in the same manner as in Example 1.

ESI-MS: m/z 562(M+1) $^1$H-NMR (300 MHz, CDCl$_3$) δ 8.55(d, J=5 Hz, 1H), 8.04–7.85(m, 0.2H), 7.63(dd, J=2,16 Hz, 1H), 7.61(d, J=16 Hz, 1H), 7.50–7.40(m, 3H), 7.35(d, J=8 Hz, 2H), 7.30–7.15(m, 2H), 6.70(d, J=8 Hz, 1H), 6.55–6.45(m, 2H), 5.35–5.25(m, 1H), 5.07–4.98(m, 1H), 4.07–4.00(m, 2H), 3.86–3.72(m, 1H), 3.70–3.52(m, 2H), 3.48–3.20(m, 3H), 2.41(s, 3H), 2.01–1.71(m, 4H).

EXAMPLE 16

5-Chloro-N-[(1S)-2-[(2-{4-[(6-methyl-2-pyridyl)oxy]-1-piperidinyl}-2-oxoethyl)amino]-2-oxo-1-(2-pyridylmethyl)ethyl]-1-benzofuran-2-carboxamide The title compound was obtained from tert-butyl 4-[(6-methyl-2-pyridyl)oxy]-1-piperidinecarboxylate and {[(2S)-2-{[(5-chloro-1-benzofuran-2-yl)carbonyl]amino}-3-(2-pyridyl)propanoyl]-amino}acetic acid in the same manner as in Example 1.

ESI-MS: m/z 576(M+1) $^1$H-NMR (300 MHz, CDCl$_3$) δ 8.80–8.70(m, 1H), 8.62(d, J=5 Hz, 1H), 8.16–8.07(m, 1H), 7.69–7.60(m, 2H), 7.51–7.35(m, 4H), 7.30–7.16(m, 2H), 6.70(d, J=8 Hz, 1H), 6.49(d, J=8 Hz, 1H), 5.35–5.25(m, 1H), 5.16–5.06(m, 1H), 4.10–4.02(m, 2H), 3.85–3.27(m, 6H), 2.41(s, 3H), 2.02–1.70(m, 4H).

Preparation 15 tert-Butyl 4-[(6-chloro-2-pyridyl)oxy]-1-piperidinecarboxylate

The title compound was obtained from tert-butyl 4-hydroxy-1-piperidinecarboxylate and 6-chloro-2-hydroxypyridine in the same manner as in Preparation 13.

$^1$H-NMR (300 MHz, CDCl$_3$) δ 7.50(dd, J=8,8 Hz, 1H), 6.87(d, J=8 Hz, 1H), 6.61(d, J=8 Hz, 1H), 5.26–5.16(m, 1H), 3.80–3.68(m, 2H), 3.35–3.25(m, 2H), 2.03–1.90(m, 2H), 1.78–1.65(m, 2H), 1.47(s, 9H).

EXAMPLE 17

(2E)-3-(4-Chlorophenyl)-N-[(1S)-2-[(2-{4-[(6-chloro-2-pyridyl)oxy]-1-piperidinyl}-2-oxoethyl)amino]-2-oxo-1-(2-pyridylmethyl)ethyl]acrylamide The title compound was obtained from tert-butyl 4-[(6-chloro-2-pyridyl)oxy]-1-piperidinecarboxylate and {[(2S)-2-{[(2E)-3-(4-chlorophenyl)-2-propenoyl]amino}-3-(2-pyridyl)-propanoyl]amino}acetic acid in the same manner as in Example 1.

ESI-MS: m/z 582(M+1) $^1$H-NMR (300 MHz, CDCl$_3$) δ 8.56(d, J=5 Hz, 1H), 8.04–7.87(m, 2H), 7.69–7.49(m, 3H), 7.46(d, J=8 Hz, 2H), 7.36(d, J=8 Hz, 2H), 7.30–7.15(m, 2H), 6.90(d, J=8 Hz, 1H), 6.64(dd, J=2,8 Hz, 1H), 6.50(d, J=16 Hz, 1H), 5.35–5.25(m, 1H), 5.07–4.99(m, 1H), 4.08–4.00(m, 2H), 3.90–3.75(m, 1H), 3.67–3.50(m, 2H), 3.49–3.20(m, 3H), 2.06–1.90(m, 2H), 1.87–1.73(m, 2H).

EXAMPLE 18

5-Chloro-N-[(1S)-2-[(2-{4-[(6-chloro-2-pyridyl)oxy]-1-piperidinyl}-2-oxoethyl)amino]-2-oxo-1-(2-pyridylmethyl)ethyl]-1-benzofuran-2-carboxamide The title compound was obtained from tert-butyl 4-[(6-chloro-2-pyridyl)oxy]-1-piperidinecarboxylate and {[(2S)-2-{[(5-chloro-1-benzofuran-2-yl)carbonyl]amino}-3-(2-pyridyl)propanoyl]-amino}acetic acid in the same manner as in Example 1.

ESI-MS: m/z 596(M+1) $^1$H-NMR (300 MHz, CDCl$_3$) δ 8.80–8.71(m, 1H), 8.62(d, J=5 Hz, 1H), 8.14(d, J=2 Hz, 1H), 7.69–7.60(m, 2H), 7.56–7.45(m, 2H), 7.41(d, J=8 Hz, 1H), 7.34(dd, J=2,8 Hz, 1H), 7.30–7.16(m, 2H), 6.90(d, J=8 Hz, 1H), 6.67(dd, J=2,8 Hz, 1H), 5.35–5.24(m, 1H), 5.15–5.07(m, 1H), 4.10–4.03(m, 2H), 3.89–3.75(m, 1H), 3.66–3.44(m, 3H), 3.40–3.28(m, 2H), 2.05–1.89(m, 2H), 1.86–1.69(m, 2H).

Preparation 16 tert-Butyl 4-{[5-(trifluoromethyl)-2-pyridyl]oxy}-1-piperidinecarboxylate

The title compound was obtained from tert-butyl 4-hydroxy-1-piperidinecarboxylate and 5-trifluoromethyl-2-hydroxypyridine in the same manner as in Preparation 13.

$^1$H-NMR (300 MHz, CDCl$_3$) δ 8.40(br s, 1H), 7.76(dd, J=2,8 Hz, 1H), 6.69(d, J=8 Hz, 1H), 5.33–5.23(m, 1H), 3.84–3.70(m, 2H), 3.35–3.23(m, 2H), 2.05–1.92(m, 2H), 1.80–1.66(m, 2H), 1.48(s, 9H).

EXAMPLE 19

(2E)-3-(4-Chlorophenyl)-N-[(1S)-2-oxo-2-{[2-oxo-2-(4-{[5-(trifluoromethyl)-2-pyridyl]oxy}-1-piperidinyl)ethyl]amino}-1-(2-pyridylmethyl)ethyl]acrylamide The title compound was obtained from tert-butyl 4-{[5-(trifluoromethyl)-2-pyridyl]oxy}-1-piperidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: m/z 616(M+1) $^1$H-NMR (300 MHz, CDCl$_3$) δ 8.55(d, J=5 Hz, 1H), 8.40(br s, 1H), 8.04–7.95(m, 1H), 7.91(d, J=8 Hz, 1H), 7.77(dd, J=2,8 Hz, 1H), 7.63(dd, J=2,16 Hz, 1H), 7.60(d, J=16 Hz, 1H), 7.45(d, J=8 Hz, 0.2H), 7.35(d, J=8 Hz, 2H), 7.29–7.15(m, 2H), 6.80(dd, J=2,8 Hz, 1H), 6.50(d, J=16 Hz, 1H), 5.41–5.30(m, 1H), 5.06–4.97(m, 1H), 4.08–4.00(m, 2H), 3.92–3.20(m, 6H), 2.06–1.92(m, 2H), 1.86–1.71(m, 2H).

EXAMPLE 20

5-Chloro-N-[(1S)-2-oxo-2-{[2-oxo-2-(4-{[5-(trifluoromethyl)-2-pyridyl]oxy}-1-piperidinyl)ethyl]amino}-1-(2-pyridylmethyl)ethyl]-1-benzofuran-2-carboxamide The title compound was obtained from tert-butyl 4-{[5-(trifluoromethyl)-2-pyridyl]oxy}-1-piperidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: m/z 630(M+1) $^1$H-NMR (300 MHz, CDCl$_3$) δ 8.75(d, J=8 Hz, 1H), 8.62(d, J=5 Hz, 1H), 8.40(br s, 1H), 8.18–8.10(m, 1H), 7.77(dd, J=2,8 Hz, 1H), 7.69–7.60(m, 2H), 7.49(d, J=8 Hz, 1H), 7.41(d, J=8 Hz, 1H), 7.39(dd, J=2,8 Hz, 1H), 7.30–7.15(m, 2H), 6.80(dd, J=2,8 Hz, 1H), 5.41–5.30(m, 1H), 5.15–5.07(m, 1H), 4.10–4.03(m, 2H), 3.90–3.80(m, 1H), 3.70–3.27(m, 5H), 2.07–1.91(m, 2H), 1.87–1.72(m, 2H).

Preparation 17 tert-Butyl 4-[(5-chloro-2-pyridyl)oxy]-1-piperidinecarboxylate

The title compound was obtained from tert-butyl 4-hydroxy-1-piperidinecarboxylate and 5-chloro-2-hydroxypyridine in the same manner as in Preparation 13.

$^1$H-NMR (300 MHz, CDCl$_3$) δ 8.06(d, J=2 Hz, 1H), 7.51(dd, J=2,8 Hz, 1H), 6.67(d, J=8 Hz, 1H), 5.20–5.10(m, 1H), 3.83–3.70(m, 2H), 3.33–3.20(m, 2H), 2.02–1.90(m, 2H), 1.77–1.64(m, 2H), 1.47(s, 9H).

EXAMPLE 21

(2E)-3-(4-Chlorophenyl)-N-[(1S)-2-[(2-{4-[(5-chloro-2-pyridyl)oxy]-1-piperidinyl}-2-oxoethyl)amino]-2-oxo-1-(2-pyridylmethyl)ethyl]acrylamide The title compound was obtained from tert-butyl 4-[(5-chloro-2-pyridyl)oxy]-1-piperidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: m/z 582(M+1) $^1$H-NMR (300 MHz, CDCl$_3$) δ 8.55(d, J=5 Hz, 1H), 8.05(d, J=2 Hz, 1H), 7.98(br s, 1H), 7.90(d, J=8 Hz, 1H), 7.63(dd, J=2,16 Hz, 1H), 7.60(d, J=16 Hz, 1H), 7.52(dd, J=2,8 Hz, 1H), 7.45(d, J=8 Hz, 2H), 7.35(d, J=8 Hz, 2H), 7.28–7.14(m, 2H), 6.66(dd, J=2,8 Hz, 1H), 6.50(d, J=16 Hz, 1H), 5.27–5.17(m, 1H), 5.06–4.97(m, 1H), 4.06–3.98(m, 2H), 3.90–3.75(m, 1H), 3.70–3.20(m, 5H), 2.03–1.70(m, 4H).

EXAMPLE 22

5-Chloro-N-[(1S)-2-[(2-{4-[(5-chloro-2-pyridyl)oxy]-1-piperidinyl}-2-oxoethyl)amino]-2-oxo-1-(2-pyridylmethyl)ethyl]-1-benzofuran-2-carboxamide The title compound was obtained from tert-butyl 4-[(5-chloro-2-pyridyl)oxy]-1-piperidinecarboxylate and {[(2S)-2-{[(5-chloro-1-benzofuran-2-yl)carbonyl]amino}-3-(2-pyridyl)propanoyl]-amino}acetic acid in the same manner as in Example 1.

ESI-MS: m/z 596(M+1) $^1$H-NMR (300 MHz, CDCl$_3$) δ 8.75(d, J=8 Hz, 1H), 8.62(d, J=5 Hz, 1H), 8.17–8.09(m, 1H), 8.05(d, J=2 Hz, 1H), 7.69–7.60(m, 2H), 7.52(dd, J=2,8 Hz, 1H), 7.49(d, J=8 Hz, 1H), 7.41(d, J=8 Hz, 1H), 7.39(dd, J=2,8 Hz, 1H), 7.30–7.17(m, 2H), 6.67(d, J=2,8 Hz, 1H), 5.27–5.17(m, 1H), 5.16–5.07(m, 1H), 4.10–4.02(m, 2H), 3.90–3.76(m, 1H), 3.65–3.43(m, 3H), 3.39–3.26(m, 2H), 2.05–1.87(m, 2H), 1.85–1.70(m, 2H).

Preparation 18 tert-Butyl 4-phenoxy-1-piperidinecarboxylate

The title compound was obtained from tert-butyl 4-hydroxy-1-piperidinecarboxylate and phenol in the same manner as in Preparation 13.

$^1$H-NMR (300 MHz, CDCl$_3$) δ 7.32–7.20(m, 2H), 6.98–6.80(m, 3H), 4.50–4.41(m, 1H), 3.75–3.64(m, 2H), 3.39–3.27(m, 2H), 1.99–1.66(m, 4H), 1.47(s, 9H).

EXAMPLE 23

(2E)-3-(4-Chlorophenyl)-N-[(1S)-2-oxo-2-{[2-oxo-2-(4-phenoxy-1-piperidinyl)ethyl]amino}-1-(2-pyridylmethyl)ethyl]-acrylamide The title compound was obtained from tert-butyl 4-phenoxy-1-piperidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: m/z 547(M+1) $^1$H-NMR (300 MHz, CDCl$_3$) δ 8.55(d, J=5 Hz, 1H), 8.05–7.82(m, 2H), 7.62(dd, J=2,16 Hz, 1H), 7.60(d, J=16 Hz, 1H), 7.45(d, J=8 Hz, 2H), 7.12–7.38 (m, 6H), 6.96(dd, J=8,8 Hz, 1H), 6.90(d, J=8 Hz, 2H), 6.49(dd, J=2,16 Hz, 1H), 5.06–4.97(m, 1H), 4.60–4.50(m, 1H), 4.06–3.99(m, 2H), 3.81–3.52(m, 3H), 3.48–3.20(m, 3H), 1.90–1.79(m, 4H).

EXAMPLE 24

5-Chloro-N-[(1S)-2-oxo-2-{[2-oxo-2-(4-phenoxy-1-piperidinyl)ethyl]amino}-1-(2-pyridylmethyl)ethyl]-1-benzofuran-2-carboxamide The title compound was obtained from tert-butyl 4-phenoxy-1-piperidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESIMS: m/z 561(M+1) $^1$H-NMR (300 MHz, CDCl$_3$) δ 8.84–8.69(m, 1H), 8.61(d, J=5 Hz, 1H), 8.19–8.08(m, 1H), 7.67–7.60(m, 2H), 7.49(d, J=8 Hz, 1H), 7.41(d, J=8 Hz, 1H), 7.38(dd, J=2,8 Hz, 1H), 7.32–7.15(m, 4H), 6.96(dd, J=8,8 Hz, 1H), 6.90(d, J=8 Hz, 2H), 5.15–5.06(m, 1H), 4.61–4.51 (m, 1H), 4.09–4.02(m, 2H), 3.80–3.44(m, 4H), 3.40–3.28 (m, 2H), 1.92–1.80(m, 4H).

Preparation 19 tert-Butyl 4-(2,2,2-trifluoroethoxy)-1-piperidinecarboxylate

To a solution of tert-butyl 4-hydroxy-1-piperidinecarboxylate (30.0 g), 2,2,2-trifluoroethanol (149 g) and triphenylphosphine (58.6 g) in tetrahydrofuran (450 ml) was slowly added diethyl azodicarboxylate (38.9 g) at 8° C. The mixture was stirred at room temperature for 2 hours, and at 60° C. for 8 hours. The reaction mixture was concentrated in vacuo to give the crude product of the title compound. The crude product was purified by chromatography on silica gel.

$^1$H-NMR (300 MHz, CDCl$_3$) δ 3.90–3.58(m, 5H), 3.20–3.10(m, 2H), 1.90–1.78(m, 2H), 1.65–1.50(m, 2H), 1.46(s, 9H).

EXAMPLE 25

(2E)-3-(4-Chlorophenyl)-N-[(1S)-2-oxo-2-({2-oxo-2-[4-(2,2,2-trifluoroethoxy)-1-piperidinyl]ethyl}amino)-1-(2-pyridylmethyl)ethyl]acrylamide The title compound was obtained from tert-butyl 4-(2,2,2-trifluoroethoxy)-1-piperidinecarboxylate and {[(2S)-2-{

[(2E)-3-(4-chlorophenyl)-2-propenoyl]amino}-3-(2-pyridyl)propanoyl]-amino}acetic acid in the same manner as in Example 1.

ESI-MS: m/z 553(M+1) $^1$H-NMR (300 MHz, CDCl$_3$) δ 8.55(d, J=5 Hz, 1H), 8.05–7.82(m, 2H), 7.62(dd, J=2,16 Hz, 1H), 7.60(d, J=16 Hz, 1H), 7.45(d, J=8 Hz, 2H), 7.34(d, J=8 Hz, 2H), 7.28–7.13(m, 2H), 6.49(dd, J=2,16 Hz, 1H), 5.05–4.95(m, 1H), 4.10–3.92(m, 2H), 3.90–3.63(m, 4H), 3.60–3.35(m, 3H), 3.30–3.16(m, 2H), 1.88–1.56(m, 4H).

EXAMPLE 26

5-Chloro-N-[(1S)-2-oxo-2-({2-oxo-2-[4-(2,2,2-trifluoroethoxy)-1-piperidinyl]ethyl}amino)-1-(2-pyridylmethyl)ethyl]-1-benzofuran-2-carboxamide The title compound was obtained from tert-butyl 4-(2,2,2-trifluoroethoxy)-1-piperidinecarboxylate and {[(2S)-2-{[(5-chloro-1-benzofuran-2-yl)carbonyl]amino}-3-(2-pyridyl)propanoyl]-amino}acetic acid in the same manner as in Example 1.

ESI-MS: m/z 567(M+1) $^1$H-NMR (300 MHz, CDCl$_3$) δ 8.83–8.67(m, 1H), 8.61(d, J=5 Hz, 1H), 8.19–8.05(m, 1H), 7.69–7.59(m, 2H), 7.49(d, J=8 Hz, 1H), 7.40(d, J=8 Hz, 1H), 7.39(dd, J=2,8 Hz, 1H), 7.30–7.16(m, 2H), 5.15–5.05(m, 1H), 4.12–3.94(m, 2H), 3.90–3.64(m, 4H), 3.60–3.42(m, 3H), 3.39–3.17(m, 2H), 1.90–1.58(m, 4H).

Preparation 20 tert-Butyl 4-isopropoxy-1-piperidinecarboxylate

The title compound was obtained from tert-butyl 4-hydroxy-1-piperidinecarboxylate and 2-iodopropane in the same manner as in Preparation 7.

$^1$H-NMR (300 MHz, CDCl$_3$) δ 3.87–3.73(m, 2H), 3.75–3.65(m, 1H), 3.55–3.45(m, 1H), 3.10–2.47(m, 2H), 1.85–1.40(m, 4H), 1.26(s, 9H), 1.15(d, J=7 Hz, 6H).

EXAMPLE 27

(2E)-3-(4-Chlorophenyl)-N-[(1S)-2-{[2-(4-isopropoxy-1-piperidinyl)-2-oxoethyl]amino}-2-oxo-1-(2-pyridylmethyl)ethyl]-acrylamide The title compound was obtained from tert-butyl 4-isopropoxy-1-piperidinecarboxylate and {[(2S)-2-{[(2E)-3-(4-chlorophenyl)-2-propenoyl]amino}-3-(2-pyridyl)propanoyl]amino}-acetic acid in the same manner as in Example 1.

ESI-MS: m/z 513(M+1) $^1$H-NMR (300 MHz, CDCl$_3$) δ 8.55(d, J=5 Hz, 1H), 8.01–7.81(m, 2H), 7.66–7.55(m, 2H), 7.45(d, J=8 Hz, 2H), 7.35(d, J=8 Hz, 2H), 7.14–7.27(m, 2H), 6.49(dd, J=2,16 Hz, 1H), 5.05–4.97(m, 1H), 4.04–3.96(m, 2H), 3.90–3.31(m, 6H), 3.29–3.10(m, 2H), 1.82–1.45(m, 4H), 1.14(d, J=7 Hz, 6H).

EXAMPLE 28

5-Chloro-N-[(1S)-2-{[2-(4-isopropoxy-1-piperidinyl)-2-oxoethyl]amino}-2-oxo-1-(2-pyridylmethyl)ethyl]-1-benzofuran-2-carboxamide The title compound was obtained from tert-butyl 4-isopropoxy-1-piperidinecarboxylate and {[(2S)-2-{[(5-chloro-1-benzofuran-2-yl)carbonyl]amino}-3-(2-pyridyl)propanoyl]amino}-acetic acid in the same manner as in Example 1.

ESI-MS: m/z 527(M+1) $^1$H-NMR (300 MHz, CDCl$_3$) δ 8.83–8.68(m, 1H), 8.61(d, J=5 Hz, 1H), 8.15–8.05(m, 1H), 7.68–7.60(m, 2H), 7.48(d, J=8 Hz, 1H), 7.44–7.35(m, 2H), 7.30–7.15(m, 2H), 5.15–5.05(m, 1H), 4.06–4.00(m, 2H), 3.89–3.75(m, 1H), 3.78–3.28(m, 6H), 3.23–3.10(m, 1H), 1.82–1.45(m, 4H), 1.14(d, J=7 Hz, 6H).

Preparation 21 tert-Butyl 4-butoxy-1-piperidinecarboxylate

The title compound was obtained from tert-butyl 4-hydroxy-1-piperidinecarboxylate and 1-iodobutane in the same manner as in Preparation 7.

$^1$H-NMR (300 MHz, CDCl$_3$) δ 3.82–3.70(m, 2H), 3.48–3.36(m, 3H), 3.12–3.00(m, 2H), 1.87–1.76(m, 2H), 1.46(s, 9H), 1.60–1.30(m, 4H), 0.98–0.80(m, 5H).

EXAMPLE 29

(2E)-N-[(1S)-2-{[2-(4-Butoxy-1-piperidinyl)-2-oxoethyl]-amino}-2-oxo-1-(2-pyridylmethyl)ethyl]-3-(4-chlorophenyl)-acrylamide The title compound was obtained from tert-butyl 4-butoxy-1-piperidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: m/z 527(M+i) $^1$H-NMR (300 MHz, CDCl$_3$) δ 8.55(d, J=5 Hz, 1H), 8.01–7.82(m, 2H), 7.62(dd, J=2,16 Hz, 1H), 7.60(d, J=16 Hz, 1H), 7.45(d, J=8 Hz, 2H), 7.35(d, J=8 Hz, 2H), 7.32–7.14(m, 2H), 6.49(dd, J=2,16 Hz, 1H), 5.05–4.95(m, 1H), 4.05–3.95(m, 2H), 3.84–3.69(m, 1H), 3.59–3.11(m, 8H), 1.84–1.70(m, 2H), 1.44–1.29(m, 4H), 0.91(t, J=7 Hz, 3H).

EXAMPLE 30

N-[(1S)-2-{[2-(4-Butoxy-1-piperidinyl)-2-oxoethyl]amino}-2-oxo-1-(2-pyridylmethyl)ethyl]-5-chloro-1-benzofuran-2-carboxamide The title compound was obtained from tert-butyl 4-butoxy-1-piperidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: m/z 541(M+1) $^1$H-NMR (300 MHz, CDCl$_3$) δ 8.87–8.55(m, 2H), 8.17–8.04(m, 1H), 7.71–7.59(m, 2H), 7.51–7.15(m, 5H), 5.15–5.04(m, 1H), 4.07–3.99(m, 2H), 3.83–3.69(m, 1H), 3.60–3.27(m, 7H), 3.24–3.11(m, 1H), 1.85–1.47(m, 6H), 1.44–1.29(m, 2H), 0.91(t, J=7 Hz, 3H).

Preparation 22 tert-Butyl 4-[(6-chloro-2-pyrazinyl)oxy]-1-piperidinecarboxylate

The title compound was obtained from tert-butyl 4-hydroxy-1-piperidinecarboxylate and 2,6-dichloropyrazine in the same manner as in Preparation 8.

ESI-MS: 314.2 (M+H) $^1$H-NMR (300 MHz, CDCl$_3$) δ 8.13(s, 1H), 8.10(s, 1H), 5.21(septet, J=4 Hz, 1H), 3.82–3.70(m, 2H), 3.32(ddd, J=14,9,4 Hz, 2H), 2.05–1.93(m, 2H), 1.82–1.68(m, 2H), 1.48(s, 9H).

EXAMPLE 31

(2E)-3-(4-Chlorophenyl)-N-[(1S)-2-[(2-{4-[(6-chloro-2-pyrazinyl)oxy]-1-piperidinyl}-2-oxoethyl)amino]-2-oxo-1-(2-pyridylmethyl)ethyl]-2-propenamide The title compound was obtained from tert-butyl 4-[(6-chloro-2-pyrazinyl)oxy]-1-piperidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: 583.2(M+H) $^1$H-NMR (300 MHz, CDCl$_3$) δ 8.56(dd, J=5,2 Hz, 1H), 8.16(s, 1H), 8.11(d, J=1.5 Hz, 1H), 8.02(s, 1H), 7.96–7.89(m, 1H), 7.64(td, J=8,2 Hz, 1H), 7.61(d, J=16 Hz, 1H), 7.46(d, J=9 Hz, 2H), 7.35(d, J=9 Hz, 2H), 7.26(d, J=8 Hz, 1H), 7.19(dd, J=8,5 Hz, 1H), 6.50(d, J=16 Hz, 1H), 5.33–5.22(m, 1H), 5.07–4.99(m, 1H), 4.05 (app d, J=4 Hz, 2H), 3.92–3.76(m, 1H), 3.67–3.51(m, 2H), 3.48–3.21(m, 3H), 2.06–1.92(m, 2H), 1.88–1.73(m, 2H).

EXAMPLE 32

5-Chloro-N-[(1S)-2-[(2-{4-[(6-chloro-2-pyrazinyl)oxy]-1-piperidinyl}-2-oxoethyl)amino]-2-oxo-1-(2-pyridylmethyl)ethyl]-1-benzofuran-2-carboxamide The title compound was obtained from tert-butyl 4-[(6-chloro-2-pyrazinyl)oxy]-1-piperidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: 597.2(M+H) $^1$H-NMR (300 MHz, CDCl$_3$) δ 8.81–8.75(m, 1H), 8.62(dd, J=5,2 Hz, 1H), 8.20–8.09(m, 3H), 7.65(td, J=8,2 Hz, 1H), 7.65(d, J=2H, 1H), 7.49(d, J=9 Hz, 1H), 7.43(s, 1H), 7.39(dd, J=9,2 Hz, 1H), 7.28(d, J=8 Hz, 1H), 7.20(dd, J=8,5 Hz, 1H), 5.33–5.23(m, 1H), 5.16–5.07(m, 1H), 4.07(app d, J=4 Hz, 2H), 3.91–3.76(m, 1H), 3.67–3.28(m, 5H), 2.07–1.91(m, 2H), 1.89–1.72(m, 2H).

Preparation 23
tert-Butyl 4-[(6-chloro-3-pyridazinyl)oxy]-1-piperidinecarboxylate The title compound was obtained from tert-butyl 4-hydroxy-1-piperidinecarboxylate and 3,6-dichloropyridazine in the same manner as in Preparation 8.

ESI-MS: 314.2(M+H) $^1$H-NMR (300 MHz, CDCl$_3$) δ 7.38(d, J=9 Hz, 1H), 6.94(d, J=9 Hz, 1H), 5.44(septet, J=4 Hz, 1H), 3.87–3.73(br m, 2H), 3.26(ddd, J=14,9,4 Hz, 2H), 2.13–2.02(m, 2H), 1.83–1.67(m, 2H), 1.48(s, 9H).

EXAMPLE 33

(2E)-3-(4-Chlorophenyl)-N-[(1S)-2-[(2-{4-[(6-chloro-3-pyridazinyl)-oxy]-1-piperidinyl}-2-oxoethyl)amino]-2-oxo-1-(2-pyridylmethyl)ethyl]-2-propenamide The title compound was obtained from tert-butyl 4-[(6-chloro-3-pyridazinyl)oxy]-1-piperidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: 583.2(M+H) $^1$H-NMR (300 MHz, CDCl$_3$) δ 8.51–8.46(m, 2H), 8.15–8.08(m, 1H), 7.82–7.78(m, 1H), 7.69(td, J=8,2 Hz, 1H), 7.56(d, J=9 Hz, 2H), 7.47(d, J=9 Hz, 2H), 7.39–7.29(m, 3H), 7.20(dd, J=8,5 Hz, 1H), 6.68(d, J=16 Hz, 1H), 5.43–5.32(m, 1H), 5.00–4.90(m, 1H), 4.04–3.97(m, 2H), 3.95–3.84(m, 1H), 3.73–3.62(m, 1H), 3.41–3.22(m, 3H), 3.07–2.96(m, 1H), 2.14–1.95(m, 2H), 1.80–1.53(m, 2H).

EXAMPLE 34

5-Chloro-N-[(1S)-2-[(2-{4-[(6-chloro-3-pyridazinyl)oxy]-1-piperidinyl}-2-oxoethyl)amino]-2-oxo-1-(2-pyridylmethyl)ethyl]-1-benzofuran-2-carboxamide The title compound was obtained from tert-butyl 4-[(6-chloro-3-pyridazinyl)oxy]-1-piperidinecarboxylate and {[(2S)-2-{[(5-chloro-1-benzofuran-2-yl)carbonyl]amino}-3-(2pyridyl)propanoyl]amino}acetic acid in the same manner as in Example 1.

ESI-MS: 597.2(M+H) $^1$H-NMR (300 MHz, CDCl$_3$) δ 8.84–8.70(m, 1H), 8.65–8.60(m, 1H), 7.69–7.61(m, 2H), 7.52–7.46(m, 1H), 7.44–7.36(m, 3H), 7.30–7.25(m, 1H), 7.23–7.18(m, 1H), 6.97–6.91(m, 1H), 5.54–5.43(m, 1H), 5.16–5.07(m, 1H), 4.11–4.03(m, 2H), 4.02–3.89(m, 1H), 3.68–3.56(m, 1H), 3.53–3.26(m, 4H), 2.17–2.00(m, 2H), 1.89–1.73(m, 2H).

Preparation 24
tert-Butyl 4-[(6-methoxy-3-pyridazinyl)oxy]-1-piperidinecarboxylate The title compound was obtained from tert-butyl 4-hydroxy-1-piperidinecarboxylate and 3-chloro-6-methoxypyridazine in the same manner as in Preparation 7.

ESI-MS: 310.2(M+H) $^1$H-NMR (300 MHz, CDCl$_3$) δ 6.96–6.88(m, 2H), 5.31(tt, J=8,4 Hz, 1H), 4.04(s, 3H), 3.89–3.75(br m, 2H), 3.22(ddd, J=14,8,4 Hz 2H), 2.13–2.01 (m, 2H), 1.81–1.66(m, 2H), 1.47(s, 9H).

EXAMPLE 35

(2E)-3-(4-Chlorophenyl)-N-[(1S)-2-[(2-{4-[(6-methoxy-3-pyridazinyl)oxy]-1-piperidinyl}-2-oxoethyl)amino]-2-oxo-1-(2-pyridylmethyl)ethyl]-2-propenamide The title compound was obtained from tert-butyl 4-[(6-methoxy-3-pyridazinyl)oxy]-1-piperidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: 579.1(M+H) $^1$H-NMR (300 MHz, CDCl$_3$) δ 8.56(dd, J=5,2 Hz, 1H), 8.06–7.84(m, 2H), 7.64(td, J=8,2 Hz, 1H), 7.61(d, J=16 Hz, 1H), 7.46(d, J=8 Hz, 2H), 7.35(d, J=8 Hz, 2H), 7.26(d, J=8 Hz, 1H), 7.18(dd, J=8,5 Hz, 1H), 6.97–6.86(m, 2H), 6.50(d, J=16 Hz, 1H), 5.42–5.31(m, 1H), 5.06–4.98(m, 1H), 4.06–3.89(m, 3H), 4.04(s, 3H), 3.66–3.56(m, 1H), 3.51–3.36(m, 2H), 3.35–3.20(m, 2H), 2.16–2.00(m, 2H), 1.87–1.72(m, 2H).

EXAMPLE 36

5-Chloro-N-[(1S)-2-[(2-{4-[(6-methoxy-3-pyridazinyl)oxy]-1-piperidinyl}-2-oxoethyl)amino]-2-oxo-1-(2-pyridylmethyl)ethyl]-1- benzofuran-2-carboxamide The title compound was obtained from tert-butyl 4-[(6-methoxy-3-pyridazinyl)oxy]-1-piperidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: 593.2(M+H) $^1$H-NMR (300 MHz, CDCl$_3$) δ 8.81–8.71(m, 1H), 8.62(dd, J=5,2 Hz, 1H), 8.20–8.10(m, 2H), 7.65(td, J=8,2 Hz, 1H), 7.65(d, J=2 Hz, 1H), 7.49(d, J=9 Hz, 1H), 7.42(s, 1H), 7.39(dd, J=9,2 Hz, 1H), 7.27(d, J=8 Hz, 1H), 7.20(dd, J=8,5 Hz, 1H), 6.97–6.87(m, 2H), 5.42–5.32(m, 1H), 5.16–5.08(m, 1H), 4.07(app d, J=4 Hz, 2H), 4.04(s, 3H), 4.01–3.90(m, 1H), 3.67–3.57(m, 1H), 3.53–3.25(m, 4H), 2.17–2.00(m, 2H), 1.87–1.73(m, 2H).

Preparation 25
tert-Butyl 4-[(3-chloro-2-pyridyl)oxy]-1-piperidinecarboxylate

The title compound was obtained from tert-butyl 4-hydroxy-1-piperidinecarboxylate and 2,3-dichloropyridine in the same manner as in Preparation 7.

ESI-MS: 313.1(M+H) $^1$H-NMR (300 MHz, CDCl$_3$) δ 8.02(dd, J=5,2 Hz, 1H), 7.63(dd, J=8,2 Hz, 1H), 6.83(dd, J=8,5 Hz, 1H), 5.32(tt, J=8,4 Hz, 1H); 3.71(ddd, J=14,8,4 Hz, 2H), 3.41(ddd, J=14,8,4 Hz, 2H), 2.02–1.89(m, 2H), 1.87–1.74(m, 2H), 1.48(s, 9H).

EXAMPLE 37

(2E)-3-(4-Chlorophenyl)-N-[(1S)-2-[(2-{4-[(3-chloro-2-pyridyl)oxy]-1-piperidinyl}-2-oxoethyl)amino]-2-oxo-1-(2-pyridylmethyl)ethyl]-2-propenamide The title compound was obtained from tert-butyl 4-[(3-chloro-2-pyridyl)oxy]-1-piperidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: 582.2(M+H) $^1$H-NMR (300 MHz, CDCl$_3$) δ 8.56(dd, J=5,2 Hz, 1H), 8.06–7.86(m, 3H), 7.68–7.57(m, 3H), 7.46(d, J=8 Hz, 2H), 7.35(d, J=8 Hz, 2H), 7.29–7.23(m, 1H), 7.18(dd, J=8,5 Hz, 1H), 6.85(dd, J=8,5 Hz, 1H), 6.50(d, J=16 Hz, 1H), 5.44–5.34(m, 1H), 5.08–4.99(m, 1H), 4.14–3.95(m, 2H), 3.85–3.54(m, 3H), 3.49–3.20(m, 3H), 2.01–1.80(m, 4H).

EXAMPLE 38

5-Chloro-N-[(1S)-2-[(2-{4-[(3-chloro-2-pyridyl)oxy]-1-piperidinyl}-2-oxoethyl)amino]-2-oxo-1-(2-pyridylmethyl)ethyl]-1-benzofuran-2-carboxamide The title compound was obtained from tert-butyl 4-[(3-chloro-2-pyridyl)oxy]-1-piperidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: 596.2(M+H) $^1$H-NMR (300 MHz, CDCl$_3$) δ 8.86–8.71(m, 1H), 8.63(dd, J=5,2 Hz, 1H), 8.21–8.09(m, 1H), 8.02(dd, J=5,2 Hz, 1H), 7.70–7.60(m, 3H), 7.50(d, J=9 Hz, 1H), 7.43(s, 1H), 7.40(dd, J=9,2 Hz, 1H), 7.28(d, J=8 Hz, 1H), 7.21(dd, J=8,5 Hz, 1H), 6.86(dd, J=8,5 Hz, 1H), 5.44–5.36(m, 1H), 5.17–5.08(m, 1H), 4.15–4.00(m, 2H), 3.85–3.56(m, 3H), 3.55–3.28(m, 3H), 2.00–1.81(m, 2H), 1.65–1.56(m, 2H).

Preparation 26 tert-Butyl 4-[(6-chloro-4-pyrimidinyl)oxy]-1-piperidinecarboxylate

The title compound was obtained from tert-butyl 4-hydroxy-1-piperidinecarboxylate and 4,6-dichloropyrimidine in the same manner as in Preparation 7.

ESI-MS: 314.2(M+H) $^1$H-NMR (300 MHz, CDCl$_3$) δ 8.55(s, 1H), 6.76(s, 1H), 5.31(tt, J=8,4 Hz, 1H), 3.84–3.70 (m, 2H), 3.29(ddd, J=14,8,4 Hz, 2H), 2.05–1.93(m, 2H), 1.81–1.66(m, 2H), 1.47(s, 9H).

EXAMPLE 39

(2E)-3-(4-Chlorophenyl)-N-[(1S)-2-[(2-{4-[(6-chloro-4-pyrimidinyl)oxy]-1-piperidinyl}-2-oxoethyl)amino]-2-oxo-1-(2-pyridylmethyl)ethyl]-2-propenamide The title compound was obtained from tert-butyl 4-[(6-chloro-4-pyrimidinyl)oxy]-1-piperidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: 583.1(M+H) $^1$H-NMR (300 MHz, CDCl$_3$) δ 8.57–8.56(m, 1H), 8.55(s, 1H), 8.05–7.99(m, 1H), 7.96–7.89(m, 1H), 7.64(td, J=8,2 Hz, 1H), 7.61(d, J=16 Hz, 1H), 7.46(d, J=9 Hz, 2H), 7.96–7.89(m, 1H), 7.64(d, J=8,2 Hz, 1H), 7.61(d, J=16 Hz, 1H), 7.46(d, J=9 Hz, 2H), 7.35(d, J=9 Hz, 2H), 7.26(d, J=8 Hz, 1H), 7.19(dd, J=8,5 Hz, 1H), 6.76(app d, J=2 Hz, 1H), 6.50(d, J=16 Hz, 1H), 5.42–5.32 (m, 1H), 5.07–4.98(m, 1H), 4.05(d, J=4 Hz, 2H), 3.93–3.77 (m, 1H), 3.65–3.47(m, 2H), 3.47–3.21(m, 3H), 2.07–1.91 (m, 2H), 1.87–1.71(m, 2H).

EXAMPLE 40

5-Chloro-N-[(1S)-2-[(2-{4-[(6-chloro-4-pyrimidinyl)oxy]-1-piperidinyl}-2-oxoethyl)amino]-2-oxo-1-(2-pyridylmethyl)ethyl]-1-benzofuran-2-carboxamide The title compound was obtained from tert-butyl 4-[(6-chloro-4-pyrimidinyl)oxy]-1-piperidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: 597.1(M+H) $^1$H-NMR (300 MHz, CDCl$_3$) δ 8.81–8.74(m, 1H), 8.63(dd, J=5,2 Hz, 1H), 8.56(s, 1H), 8.17(br s, 1H), 7.66(td, J=8,2 Hz, 1H), 7.66(d, J=2 Hz, 1H), 7.50(d, J=9 Hz, 1H), 7.43(s, 1H), 7.40(dd, J=9,2 Hz, 1H), 7.29(d, J=8 Hz, 1H), 7.22(dd, J=8,5 Hz, 1H), 6.77(app d, J=2 Hz, 1H), 5.44–5.33(m, 1H), 5.16–5.08(m, 1H), 4.09(app d, 2H), 3.92–3.78(m, 1H), 3.67–3.44(m, 3H), 3.41–3.29(m, 2H), 2.08–1.92(m, 2H), 1.88–1.72(m, 2H).

Preparation 27 tert-Butyl 4-{[6-(trifluoromethyl)-4-pyrimidinyl]oxy}-1-piperidinecarboxylate

The title compound was obtained from tert-butyl 4-hydroxy-1-piperidinecarboxylate and 6-(trifluoromethyl)-4-pyrimidinol in the same manner as in Preparation 13.

ESI-MS: 348.3(M+H) $^1$H-NMR (300 MHz, CDCl$_3$) δ 8.86(s, 1H), 7.06(s, 1H), 5.39(tt, J=8,4 Hz, 1H), 3.85–3.72 (m, 2H), 3.30(ddd, J=14,8,4 Hz, 2H), 2.08–1.95(m, 2H), 1.84–1.68(m, 2H), 1.48(s, 9H).

EXAMPLE 41

(2E)-3-(4-Chlorophenyl)-N-[(1S)-2-oxo-2-{[2-oxo-2-(4-{[6-(trifluoromethyl)-4-pyrimidinyl]oxy}-1-piperidinyl)ethyl]amino}-1-(2-pyridylmethyl)ethyl]-2-propenamide The title compound was obtained from tert-butyl 4-{[6-(trifluoromethyl)-4-pyrimidinyl]oxy}-1-piperidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: 617.1(M+H) $^1$H-NMR (300 MHz, CDCl$_3$) δ 8.86(s, 1H), 8.57(dd, J=5,2 Hz, 1H), 8.08–8.01(m, 1H), 7.98–7.89(m, 1H), 7.64(td, J=8,2 Hz, 1H), 7.61(d, J=16 Hz, 1H), 7.46(d, J=9 Hz, 2H), 7.35(d, J=9 Hz, 2H), 7.27(d, J=8 Hz, 1H), 7.19(dd, J=8,5 Hz, 1H), 7.07(s, 1H), 6.50(d, J=16 Hz, 1H), 5.51–5.41(m, 1H), 5.06–4.98(m, 1H), 4.05(d, J=4 Hz, 2H), 3.96–3.80(m, 1H), 3.68–3.50(m, 2H), 3.50–3.21 (m, 3H), 2.10–1.95(m, 2H), 1.90–1.74(m, 2H).

EXAMPLE 42

5-Chloro-N-[(1S)-2-oxo-2-{[2-oxo-2-(4-{[6-(trifluoromethyl)-4-pyrimidinyl]oxy}-1-piperidinyl)ethyl]amino}-1-(2-pyridylmethyl)ethyl]-1-benzofuran-2-carboxamide The title compound was obtained from tert-butyl 4-{[6-(trifluoromethyl)-4-pyrimidinyl]oxy}-1-piperidinecarboxylate and {[(2S)-2-{[(5-chloro-1-benzofuran-2-yl)carbonyl]amino}-3-(2 pyridyl)propanoyl]amino}acetic acid in the same manner as in Example 1.

ESI-MS: 631.1(M+H) $^1$H-NMR (300 MHz, CDCl$_3$) δ 8.86(s, 1H), 8.84–8.75(m, 1H), 8.63(dd, J=5,2 Hz, 1H), 8.20(br s, 1H), 7.65(td, J=8,2 Hz, 1H), 7.65(d, J=2 Hz, 1H), 7.49(dd, J=9,1 Hz, 1H), 7.43(d, J=1 Hz, 1H), 7.39(dd, J=9,2

Hz, 1H), 7.28(d, J=8 Hz, 1H), 7.21(dd, J=8,5 Hz, 1H), 7.07(s, 1H), 5.52–5.41(m, 1H), 5.16–5.07(m, 1H), 4.09(app d, J=4 Hz, 2H), 3.95–3.80(m, 1H), 3.69–3.45(m, 3H), 3.42–3.30(m, 2H), 2.11–1.95(m, 2H), 1.90–1.75(m, 2H).

Preparation 28 tert-Butyl 4-{[2-(trifluoromethyl)-4-pyrimidinyl]oxy}-1-piperidinecarboxylate

The title compound was obtained from tert-butyl 4-hydroxy-1-piperidinecarboxylate and 4-hydroxy-2-(trifluoromethyl)-pyrimidine in the same manner as in Preparation 13.

ESI-MS: 348.3(M+H) $^1$H-NMR (300 MHz, CDCl$_3$) δ 8.56(d, J=6 Hz, 1H), 6.86(d, J=6 Hz, 1H), 5.39(tt, J=8,4 Hz, 1H), 3.83–3.71(m, 2H), 3.33(ddd, J=14,8,4 Hz, 2H), 2.08–1.96(m, 2H), 1.84–1.68(m, 2H), 1.48(s, 9H).

EXAMPLE 43

5-Chloro-N-[(1S)-2-oxo-2-{[2-oxo-2-(4-{[2-(trifluoromethyl)-4-pyrimidinyl]oxy}-1-piperidinyl)ethyl]amino}-1-(2-pyridylmethyl)ethyl]-1-benzofuran-2-carboxamide The title compound was obtained from tert-butyl 4-{[2-(trifluoromethyl)-4-pyrimidinyl]oxy}-1-piperidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: 631.1(M+H) $^1$H-NMR (300 MHz, CDCl$_3$) δ 8.84–8.74(m, 1H), 8.63(dd, J=5,2 Hz, 1H), 8.58(d, J=6 Hz, 1H), 8.24–8.14(m, 1H), 7.65(td, J=8,2 Hz, 1H), 7.65(d, J=2 Hz, 1H), 7.49(d, J=9 Hz, 1H), 7.43(s, 1H), 7.39(dd, J=9,2 Hz, 1H), 7.28(d, J=Hz, 1H), 7.21(dd, J=8,5 Hz, 1H), 6.87(d, J=6 Hz, 1H), 5.51–5.41(m, 1H), 5.16–5.08(m, 1H), 4.08(app d, 2H), 3.94–3.80(m, 1H), 3.68–3.44(m, 3H), 3.44–3.29(m, 2H), 2.11–1.95(m, 2H), 1.90–1.74(m, 2H).

Preparation 29 tert-Butyl 4-[(5-chloro-2-pyrazinyl)oxy]-1-piperidinecarboxylate

The title compound was obtained from tert-butyl-4-hydroxy-1-piperidinecarboxylate and 5-chloro-2-pyrazinol in the same manner as in Preparation 13. 5-Chloro-2-pyrazinol was prepared according to the method described in J. Org. Chem. 29, 2491–2492 (1964).

ESI-MS: 314.2(M+H) $^1$H-NMR (300 MHz, CDCl$_3$) δ 8.07(d, J=1 Hz, 1H), 7.99(d, J=1 Hz, 1H), 5.14(tt, J=8,4 Hz, 1H), 3.83–3.70(m, 2H), 3.29(ddd, J=14,8,4 Hz, 2H), 2.03–1.91(m, 2H), 1.66–1.80(m, 2H), 1.48(s, 9H).

EXAMPLE 44

5-Chloro-N-[(1S)-2-[(2-{4-[(5-chloro-2-pyrazinyl)oxy]-1-piperidinyl}-2-oxoethyl)amino]-2-oxo-1-(2-pyridylmethyl)ethyl]-1-benzofuran-2-carboxamide The title compound was obtained from tert-butyl 4-[(5-chloro-2-pyrazinyl)oxy]-1-piperidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: 597.1(M+H) $^1$H-NMR (300 MHz, CDCl$_3$) δ 8.82–8.72(m, 1H), 8.62(dd, J=5,2 Hz, 1H), 8.21–8.13(m, 1H), 8.06(s, 1H), 7.99(s, 1H), 7.65(td, J=8,2 Hz, 1H), 7.65(d, J=2 Hz, 1H), 7.49(d, J=9 Hz, 1H), 7.42(s, 1H), 7.39(dd, J=9,2 Hz, 1H), 7.27(d, J=8 Hz, 1H), 7.21(dd, J=8,5 Hz, 1H), 5.26–5.16(m, 1H), 5.15–5.07(m, 1H), 4.08(app d, 2H), 3.90–3.75(m, 1H), 3.67–3.43(m, 3H), 3.40–3.28(m, 2H), 2.06–1.90(m, 2H), 1.87–1.71(m, 2H).

Preparation 30

2-Bromo-5-methyl-1,3-thiazole

To a solution of 2-amino-5-methyl-1,3-thiazole (11.7 g) in acetonitrile (200 ml) was added dropwise tert-butyl nitrite (8.33 ml) at 0° C. followed by addition of copper(II) bromide (5 g) over 5 minutes. After stirring at 0° C. for 3 hours, the mixture was concentrated and partitioned between 1N hydrochloric acid and ethyl acetate. The organic layer was washed with water, saturated aqueous sodium hydrogencarbonate solution and brine, dried over anhydrous magnesium sulfate, filtered through a pad of Celite, and concentrated in vacuo to give the title compound (3.24 g) as an oil.

ESI-MS: 177.8(M+H) $^1$H-NMR (300 MHz, CDCl$_3$) δ 7.25(s, 1H), 2.44(s, 3H).

Preparation 31 tert-Butyl 4-[(5-methyl-1,3-thiazol-2-yl)oxy]-1-piperidinecarboxylate

The title compound was obtained from tert-butyl 4-hydroxy-1-piperidinecarboxylate and 2-bromo-5-methyl-1,3-thiazole in the same manner as in Preparation 7.

ESI-MS: 299.3(M+H) $^1$H-NMR (300 MHz, CDCl$_3$) δ 6.74(s, 1H), 5.06(tt, J=8,4 Hz, 1H), 3.78–3.66(m, 2H), 3.30(ddd, J=14,8,4 Hz, 2H), 2–0.31(s, 3H), 2.06–1.95(m, 2H), 1.85–1.72(m, 2H), 1.47(s, 9H).

EXAMPLE 45

(2E)-3-(4-Chlorophenyl)-N-[(1S)-2-[(2-{4-[(5-methyl-1,3-thiazol-2-yl)oxy]-1-piperidinyl}-2-oxoethyl)amino]-2-oxo-1-(2-pyridylmethyl)ethyl]-2-propenamide The title compound was obtained from tert-butyl 4-[(5-methyl-1,3-thiazol-2-yl)oxy]-1-piperidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: 568.2(M+H) $^1$H-NMR (300 MHz, CDCl$_3$) δ 8.55(dd, J=5,2 Hz, 1H), 8.04–7.97(m, 1H), 7.96–7.87(m, 1H), 7.63(td, J=8,2 Hz, 1H), 7.61(d, J=16 Hz, 1H), 7.45(d, J=8 Hz, 2H), 7.34(d, J=8 Hz, 2H), 7.25(d, J=8 Hz, 1H), 7.18(dd, J=8,5 Hz, 1H), 6.73(app s, 1H), 6.50(d, J=16 Hz, 1H), 5.13(br s, 1H), 5.06–4.98(m, 1H), 4.03(app d, J=4 Hz, 2H), 3.83–3.49(m, 3H), 3.43(dd, J=15,5 Hz, 1H), 3.37–3.20 (m, 2H), 2.31(d, J=1 Hz, 3H), 2.05–1.79(m, 4H).

EXAMPLE 46

5-Chloro-N-[(1S)-2-[(2-{4-[(5-methyl-1,3-thiazol-2-yl)oxy]-1-piperidinyl}-2-oxoethyl)amino]-2-oxo-1-(2-pyridylmethyl)ethyl]-1-benzofuran-2-carboxamide The title compound was obtained from tert-butyl 4-[(5-methyl-1,3-thiazol-2-yl)oxy]-1-piperidinecarboxylate and {[(2S)-2-{[(5-chloro-1–1-benzofuran-2-yl)carbonyl]amino}-3-(2-pyridyl)propanoyl]amino}acetic acid in the same manner as in Example 1.

ESI-MS: 582.2(M+H) $^1$H-NMR (300 MHz, CDCl$_3$) δ 8.81–8.73(m, 1H), 8.63(dd, J=5,2 Hz, 1H), 8.19–8.11(m, 1H), 7.66(td, J=8,2 Hz, 1H), 7.66(d, J=2 Hz, 1H), 7.50(d, J=9 Hz, 1H), 7.43(s, 1H), 7.39(dd, J=9,2 Hz, 1H), 7.28(d, J=8 Hz, 1H), 7.21(dd, J=8,5 Hz, 1H), 7.43(s, 1H), 7.39(dd, J=9,2 Hz, 1H), 7.28(d, J=8 Hz, 1H), 7.21(dd, J=8,5 Hz, 1H), 6.75–6.71(m, 1H), 5.19–5.07(m, 2H), 4.07(app d, J=4 Hz, 2H), 3.81–3.44(m, 4H), 3.39–3.27(m, 2H), 2.31(d, J=1 Hz, 3H), 2.07–1.78(m, 4H).

Preparation 32 tert-Butyl. 4-[(5-chloro-1,3-thiazol-2-yl)oxy]-1-piperidinecarboxylate

To a solution of tert-butyl 4-[(1,3-thiazol-2-yl)oxy]-1-piperidinecarboxylate (8.0 g) in acetic acid (80 ml) was added dropwise N-chlorosuccinimide (4.5 g). The mixture was warmed to 60–70° C. and stirred for 5 hours. The resulting mixture was poured into a mixture of ice (80 g) and water (80 ml), and extracted with ethyl acetate. The organic layer was concentrated in vacuo, and the residue was dissolved in ethyl acetate. The solution was basified with 1N sodium hydroxide solution. The organic layer was washed with brine, dried over anhydrous magnesium sulfate and concentrated in vacuo. The residue was purified by silica gel column chromatography (eluent; 9% ethyl acetate in n-hexane) to give the title compound (5.56 g) as white crystals.

ESI-MS: 319.2(M+H) $^1$H-NMR (300 MHz, CDCl$_3$) δ 6.93(s, 1H), 5.11(tt, J=8,4 Hz, 1H), 3.79–3.63(m, 2H), 3.31(ddd, J=14,8,4 Hz, 2H), 2.07–1.94(m, 2H), 1.87–1.72(, 2H), 1.47(s, 9H).

EXAMPLE 47

(2E)-3-(4-Chlorophenyl)-N-[(1S)-2-[(2-{4-[(5-chloro-1,3-thiazol-2-yl)oxy]-1-piperidinyl}-2-oxoethyl)amino]-2-oxo-1-(2-pyridylmethyl)ethyl]-2-propenamide The title compound was obtained from tert-butyl 4-[(5-chloro-1,3-thiazol-2-yl)oxy]-1-piperidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: 588.1(M+H) $^1$H-NMR (300 MHz, CDCl$_3$) δ 8.55(dd, J=5,2 Hz, 1H), 8.0–6–7.98(m, 1H), 7.95–7.88(m, 1H), 7.63(td, J=8,2 Hz, 1H), 7.61(d, J=16 Hz, 1H), 7.46(d, J=8 Hz, 2H), 7.35(d, J=8 Hz, 2H), 7.25(d, J=8 Hz, 1H), 7.18(dd, J=8,5 Hz, 1H), 6.92(s, 1H), 6.50(d, J=16 Hz, 1H), 5.23–5.13(m, 1H), 5.05–4.97(m, 1H), 4.03(app d, J=4 Hz, 2H), 3.83–3.49(m, 3H), 3.48–3.20(m, 3H), 2.06–1.78(m, 4H).

EXAMPLE 48

5-Chloro-N-[(1S)-2-[(2-{4-[(5-chloro-1,3-thiazol-2-yl)oxy]1-piperidinyl}-2-oxoethyl)amino]-2-oxo-1-(2-pyridylmethyl)ethyl]-1-benzofuran-2-carboxamide The title compound was obtained from tert-butyl 4-[(5-chloro-1,3-thiazol-2-yl)oxy]-1-piperidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: 602.1(M+H) $^1$H-NMR (300 MHz, CDCl$_3$) δ 8.81–8.73(m, 1H), 8.63(dd, J=5,2 Hz, 1H), 8.21–8.13(m, 1H), 7.65(td, J=8,2 Hz, 1H), 7.65(d, J=2 Hz, 1H), 7.49(d, J=9 Hz, 1H), 7.42(s, 1H), 7.39(dd, J=9,2 Hz, 1H), 7.27(d, J=8 Hz, 1H), 7.20(dd, J=8,5 Hz, 1H), 6.92(s, 1H), 5.23–5.06 (m, 2H), 4.06(app d, J=4 Hz, 2H), 3.81–3.43(m, 4H), 3.40–3.27(m, 2H), 2.06–1.78(m, 4H).

Preparation 33 tert-Butyl(3R)-3-[(5-chloro-2-pyridyl)oxy]-1-pyrrolidinecarboxylate

The title compound was obtained from tert-butyl(3R)-3-hydroxy-1-pyrrolidinecarboxylate and 2,5-dichloropyridine in the same manner as in Preparation 7.

ESI-MS: 299.1(M+H) $^1$H-NMR (300 MHz, CDCl$_3$) δ 8.08(s, 1H), 7.53(d, J=9 Hz, 1H), 6.69(d, J=9 Hz, 1H), 5.49(br s, 1H), 3.71–3.40(m, 4H), 2.14(br s, 2H), 1.47(s, 9H).

EXAMPLE 49

(2E)-3-(4-Chlorophenyl)-N-[(1S)-2-[(2-{(3R)-3-[(5-chloro-2-pyridyl)oxy]-1-pyrrolidinyl}-2-oxoethyl)amino]-2-oxo-1-(2-pyridylmethyl)ethyl]-2-propenamide The title compound was obtained from tert-butyl(3R)-3-[(5-chloro-2-pyridyl)oxy]-1-pyrrolidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: 568.1(M+H) $^1$H-NMR (300 MHz, CDCl$_3$) δ 8.58–8.53(m, 1H), 8.08–8.05(m, 1H), 8.03–7.98(m, 1H), 7.90–7.83(m, 1H), 7.66–7.50(m, 3H), 7.45(d, J=8 Hz, 2H), 7.34(d, J=8 Hz, 2H), 7.28–7.22(m, 1H), 7.21–7.14(m, 1H), 6.69–6.61(m, 1H), 6.49(d, J=16 Hz, 1H), 5.58–5.49(m, 1H), 5.06–4.97(m, 1H), 3.99(d, J=4 Hz, 1H), 3.91(d, J=4 Hz, 1H), 3.83–3.51(m, 4H), 3.46–3.37(m, 1H), 3.30–3.21(m, 1H), 2.34–2.06(m, 2H).

EXAMPLE 50

5-Chloro-N-[(1S)-2-[(2-{(3R)-3-[(5-chloro-2-pyridyl)oxy]-1-pyrrolidinyl}-2-oxoethyl)amino]-2-oxo-1-(2-pyridylmethyl)ethyl]-1-benzofuran-2-carboxamide The title compound was obtained from tert-butyl(3R)-3-[(5-chloro-2-pyridyl)oxy]-1-pyrrolidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: 582.2(M+H) $^1$H-NMR (300 MHz, CDCl$_3$) δ 8.75–8.69(m, 1H), 8.69–8.65(m, 1H), 8.21–8.14(m, 1H), 8.08–8.04(m, 1H), 7.68–7.60(m, 2H), 7.57–7.45(m, 2H), 7.43–7.35(m, 2H), 7.30–7.16(m, 2H), 6.69–6.62(m, 1H), 5.58–5.49(m, 1H), 5.15–5.06(m, 1H), 4.02(d, J=4 Hz, 1H), 3.94(d, J=4 Hz, 1H), 3.84–3.28(m, 6H), 2.35–2.07(m, 2H).

Preparation 34 tert-Butyl(3S)-3-[(5-chloro-2-pyridyl)oxy]-1-pyrrolidinecarboxylate

The title compound was obtained from tert-butyl(3S)-3-hydroxy-1-pyrrolidinecarboxylate and 5-chloro-2-pyridinol in the same manner as in Preparation 13.

ESI-MS: 299.1(M+H) $^1$H-NMR (300 MHz, CDCl$_3$) δ 8.08(s, 1H), 7.53(d, J=9 Hz, 1H), 6.68(d, J=9 Hz, 1H), 5.48(br s, 1H), 3.69–3.42(m, 4H)., 2.14(br s, 2H), 1.46(s, 9H).

EXAMPLE 51

(2E)-3-(4-Chlorophenyl)-N-[(1S)-2-[(2-{(3S)-3-[(5-chloro-2-pyridyl)oxy]-1-pyrrolidinyl}-2-oxoethyl)amino]-2-oxo-1-(2-pyridylmethyl)ethyl]-2-propenamide The title compound was obtained from tert-butyl(3S)-3-[(5-chloro-2-pyridyl)oxy]-1-pyrrolidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: 568.2(M+H) $^1$H-NMR (300 MHz, CDCl$_3$) δ 8.60–8.51(m, 1H), 8.11–7.95(m, 2H), 7.93–7.84(m, 1H), 7.68–7.40(m, 5H), 7.39–7.12(m, 4H), 6.70–6.61(m, 1H), 6.55–6.43(m, 1H), 5.59–5.47(m, 1H), 5.07–4.95(m, 1H), 4.04–3.88(m, 1H), 3.86–3.18(m, 6H), 2.38–2.02(m, 2H).

EXAMPLE 52

5-Chloro-N-[(1S)-2-[(2-{(3S)-3-[(5-chloro-2-pyridyl)oxy]-1-pyrrolidinyl}-2-oxoethyl)amino]-2-oxo-1-(2-pyridylmethyl)ethyl]-1-benzofuran-2-carboxamide The title compound was obtained from tert-butyl(3S)-3-[(5-chloro-2-pyridyl)oxy]-1-pyrrolidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: 582.2(M+H) $^1$H-NMR (300 MHz, CDCl$_3$) δ 8.77–8.71(m, 1H), 8.64–8.59(m, 1H), 8.21–8.12(m, 1H), 8.08–8.04(m, 1H), 7.68–7.60(m, 2H), 7.56–7.45(m, 2H), 7.41(s, 1H), 7.38(dd, J=9,2 Hz, 1H), 7.30–7.23(m, 1H), 7.22–7.16(m, 1H), 6.65(d, J=9 Hz, 1H), 5.58–5.49(m, 1H), 5.15–5.07(m, 1H), 4.02(d, J=4 Hz, 1H), 3.94(d, J=4 Hz, 1H), 3.84–3.42(m, 5H), 3.33(dd, J=15,6 Hz, 1H), 2.36–2.07(m, 2H).

Preparation 35 tert-Butyl(3R)-3-[(6-chloro-2-pyrazinyl)oxy]-1-pyrrolidinecarboxylate

The title compound was obtained from tert-butyl(3R)-3-hydroxy-1-pyrrolidinecarboxylate and 2,6-dichloropyrazine in the same manner as in Preparation 7.

$^1$H-NMR (300 MHz, CDCl$_3$) δ 8.17(s, 1H), 7.12(s, 1H), 5.54(br s, 1H), 3.73–3.43(m, 4H), 2.26–2.12(m, 2H), 1.48(s, 9H).

EXAMPLE 53

(2E)-3-(4-Chlorophenyl)-N-[(1S)-2-[(2-{(3R)-3-[(6-chloro-2-pyrazinyl)oxy]-1-pyrrolidinyl}-2-oxoethyl)amino]-2-oxo-1-(2-pyridylmethyl)ethyl]-2-propenamide The title compound was obtained from tert-butyl(3R)-3-[(6-chloro-2-pyrazinyl)oxy]-1-pyrrolidinecarboxylate and {[(2S)-2-{[(2E)-3-(4-chlorophenyl)-2-propenoyl]amino}-3-(2-pyridyl)propanoyl]amino}acetic acid in the same manner as in Example 1

ESI-MS: 569.1(M+H) $^1$H-NMR (300 MHz, CDCl$_3$) δ 8.59–8.53(m, 1H), 8.22–8.00 m, 3H), 7.91–7.84(m, 1H), 7.67–7.56(m, 2H), 7.46(d, J=8 Hz, 2H), 7.35(d, J=8 Hz, 2H), 7.29–7.24(m, 1H), 7.22–7.14(m, 1H), 6.49(d, J=16 Hz, 1H), 5.65–5.53(m, 1H), 5.07–4.97(m, 1H), 4.02(d, J=4 Hz, 1H), 3.94(d, J=4 Hz, 1H), 3.88–3.54(m, 4H), 3.47–3.36(m, 1H), 3.31–3.21(m, 1H), 2.39–2.12(m, 2H).

EXAMPLE 54

5-Chloro-N-[(1S)-2-[(2-{(3R)-3-[(6-chloro-2-pyrazinyl)oxy]-1-pyrrolidinyl}-2-oxoethyl)amino]-2-oxo-1-(2-pyridylmethyl)-ethyl]-1-benzofuran-2-carboxamide The title compound was obtained from tert-butyl(3R)-3-[(6-chloro-2-pyrazinyl)oxy]-1-pyrrolidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: 583.1 (M+H) $^1$H-NMR (300 MHz, CDCl$_3$) δ 8.68–8.60(m, 1H), 8.36–8.28(m, 1H), 8.21–8.10(m, 2H), 7.77–7.69(m, 1H), 7.65–7.63(m, 1H), 7.50–7.45(m, 1H), 7.42–7.24(m, 4H), 5.65–5.54(m, 1H), 5.20–5.11(m, H), 4.09–4.02(m, 1H), 4.01–3.95(m, 1H), 3.88–3.58(m, 4H), 3.51–3.44(m, 2H), 2.38–2.10(m, 2H).

Preparation 36 tert-Butyl(3R)-3-[(5-methyl-1,3-thiazol-2-yl)oxy]-1-pyrrolidinecarboxylate

The title compound was obtained from tert-butyl(3R)-3-hydroxy-1-pyrrolidinecarboxylate and 2-bromo-5-methyl-1,3-thiazole in the same manner as in Preparation 7.

ESI-MS: 285.1(M+H) $^1$H-NMR (300 MHz, CDCl$_3$) δ 6.75(s, 1H), 5.46–5.40(m, 1H), 3.77–3.38(m, 4H), 2.31(s, 3H), 2.40–2.00(m, 2H), 1.47(s, 9H).

EXAMPLE 55

(2E)-3-(4-Chlorophenyl)-N-[(1S)-2-[(2-{(3R)-3-[(5-methyl-1,3-thiazol-2-yl)oxy]-1-pyrrolidinyl}-2-oxoethyl)amino]-2-oxo-1-(2-pyridylmethyl)ethyl]-2-propenamide The title compound was obtained from tert-butyl(3R)-3-[(5-methyl-1,3-thiazol-2-yl)oxy]-1-pyrrolidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: 554.1(M+H) $^1$H-NMR (300 MHz, CDCl$_3$) δ 8.58–8.52(m, 1H), 8.06–7.95(m, 1H), 7.93–7.80(m, 1H), 7.67–7.55(m, 2H), 7.45(d, J=8 Hz, 2H), 7.34(d, J=8 Hz, 2H), 7.28–7.22(m, 1H), 7.21–7.14(m, 1H), 6.74(s, 1H), 6.49(d, J=16 Hz, 1H), 5.53–5.43(m, 1H), 5.06–4.97(m, 1H), 4.01–3.90(m, 2H), 3.79–3.19(m, 6H), 2.33–2.03(m, 5H).

EXAMPLE 56

5-Chloro-N-[(1S)-2-[(2-{(3R)-3-[(5-methyl-1,3-thiazol-2-yl)oxy]-1-pyrrolidinyl}-2-oxoethyl)amino]-2-oxo-1-(2-pyridylmethyl)ethyl]-1-benzofuran-2-carboxamide The title compound was obtained from tert-butyl(3R)-3-[(5-methyl-1,3-thiazol-2-yl)oxy]-1-pyrrolidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: 568.1(M+H) $^1$H-NMR (300 MHz, CDCl$_3$) δ 8.77–8.67(m, 1H), 8.64–8.59(m, 1H), 8.23–8.13(m, 1H), 7.64(td, J=8,2 Hz, 1H), 7.64(d, J=2 Hz, 1H), 7.48(d, J=9 Hz, 1H), 7.41(s, 1H), 7.38(dd, J=9,2 Hz, 1H), 7.30–7.24(m, 1H), 7.23–7.16(m, 1H), 6.76–6.71(m, 1H), 5.53–5.43(m, 1H), 5.15–5.07(m, 1H), 4.05–3.99(m, 1H), 3.98–3.93(m, 1H), 3.79–3.28(m, 6H), 2.33–2.05(m, 5H).

Preparation 37 tert-Butyl 3-{[6-(trifluoromethyl)-4-pyrimidinyl]oxy}-1-azetidinecarboxylate

The title compound was obtained from tert-butyl 3-hydroxy-1-azetidinecarboxylate and 6-(trifluoromethyl)-4-pyrimidinol in the same manner as in Preparation 13.

ESI-MS: 320.2(M+H) $^1$H-NMR (300 MHz, CDCl$_3$) δ 8.87(s, 1H), 7.14(s, 1H), 5.44(tt, J=7,4 Hz, 1H), 4.37(dd, J=10,7 Hz, 2H), 4.01(dd, J=10,4 Hz, 2H), 1.45(s, 9H).

EXAMPLE 57

(2E)-3-(4-Chlorophenyl)-N-[(1S)-2-oxo-2-{[2-oxo-2-(3-{[6-(trifluoromethyl)-4-pyrimidinyl]oxy}-1-azetidinyl)ethyl]amino}-1-(2-pyridylmethyl)ethyl]-2-propenamide The title compound was obtained from tert-butyl 3-{[6-(trifluoromethyl)-4-pyrimidinyl]oxy}-1-azetidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: 589.2(M+H) $^1$H-NMR (300 MHz, CDCl$_3$) δ 8.88(s, 1H), 8.55(dd, J=5,2 Hz, 1H), 8.06(br s, 1H), 7.91–7.84(m, 1H), 7.64(td, J=8,2 Hz, 1H), 7.59(d, J=16 Hz, 1H), 7.45(d, J=8 Hz, 2H), 7.35(d, J=8 Hz, 2H), 7.26(d, J=8 Hz, 1H), 7.19(dd, J=8,5 Hz, 1H), 7.15(s, 1H), 6.48(d, J=16 Hz, 1H), 5.57–5.47(m, 1H), 5.05–4.96(m, 1H), 4.64–4.42(m, 2H), 4.24–4.06(m, 2H), 3.89(app d, J=4 Hz, 2H), 3.41(dd, J=15,5 Hz, 1H), 3.26(dd, J=15,6 Hz, 1H).

EXAMPLE 58

5-Chloro-N-[(1S)-2-oxo-2-{[2-oxo-2-(4-{[6-(trifluoromethyl)-4-pyrimidinyl]oxy}-1-azetidinyl)ethyl]amino}-1-(2-pyridylmethyl)ethyl]-1-benzofuran-2-carboxamide The title compound was obtained from tert-butyl 3-{[6-(trifluoromethyl)-4-pyrimidinyl]oxy}-1-azetidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: 603.1(M+H) $^1$H-NMR (300 MHz, CDCl$_3$) δ 8.88(s, 1H), 8.74–8.67(m, 1H), 8.61(dd, J=5,2 Hz, 1H), 8.26(br s, 1H), 7.65(td, J=8,2 Hz, 1H), 7.65(d, J=2 Hz, 1H), 7.49(d, J=9 Hz, 1H), 7.41(s, 1H), 7.39(dd, J=9,2 Hz, 1H), 7.28(d, J=8 Hz, 1H), 7.21(dd, J=8,5 Hz, 1H), 7.15(s, 1H), 5.58–5.48(m, 1H), 5.14–5.05(m, 1H), 4.65–4.55(m, 1H), 4.52–4.43(m, 1H), 4.25–4.06(m, 2H), 3.89(app d, J=4 Hz, 2H), 3.47(dd, J=15,4 Hz, 1H), 3.33(dd, J=15,7 Hz, 1H).

Preparation 38

3,5-Dichloro-2-(4-piperidinyloxy)pyridine dihydrochloride

To a solution of tert-butyl 4-hydroxy-1-piperidinecarboxylate (0.5 g), 3,5-dichloro-2-pyridone (0.41 g) and triphenylphosphine (0.98 g) in tetrahydrofuran was slowly added diethyl azodicarboxylate (0.65 g) at 8° C., and the mixture was stirred at room temperature for 4 hours. The reaction mixture was concentrated in vacuo to give the crude product.

To a solution of the crude product in methanol (5 ml) was added 4N hydrogen chloride in ethyl acetate (6.2 ml) at 8° C. The mixture was stirred at room temperature for 1 hour and concentrated in vacuo. The residual solid was washed with ethyl acetate to give the title compound (585 mg).

$^1$H-NMR (300 MHz, CDCl$_3$) δ 7.99(d, J=2 Hz, 1H), 7.68(d, J=2 Hz, 1H), 5.45–5.37(m, 1H), 3.45–3.29(m, 4H), 2.44–2.13(m, 4H).

EXAMPLE 59

(2E)-3-(4-Chlorophenyl)-N-[(1S)-2-[(2-{4-[(3,5-dichloro-2-pyridyl)oxy]-1-piperidinyl}-2-oxoethyl)amino]-2-oxo-1-(2-pyridylmethyl)ethyl]-2-propenamide To a mixture of {[(2S)-2-{[(2E)-3-(4-chlorophenyl)-2-propenoyl]amino}-3-(2-pyridyl)propanoyl]amino}acetic acid (0.19 g), 3,5-dichloro-2-(4-piperidinyloxy)pyridine dihydrochloride (0.16 g), 1-hydroxybenzotriazole (0.084 g) and 1-(3-dimethylaminopropyl)-3-ethylcarbodiimide hydrochloride (0.11 g) in N,N-dimethylformamide (2.5 ml) was added dropwise N,N-diisopropylethylamine (0.27 ml) at 8° C. The mixture was warmed to room temperature and stirred for 6 hours. The reaction mixture was poured into ice-water and extracted with ethyl acetate. The organic layer was washed with saturated aqueous sodium hydrogencarbonate solution and brine, dried over anhydrous sodium sulfate and concentrated in vacuo. The residue was purified by silica gel column chromatography to give the title compound (231 mg).

$^1$H-NMR (300 MHz, CDCl$_3$) δ 8.61–8.53(m, 1H), 8.07–7.85(m, 3H), 7.70–7.57(m, 3H), 7.45(d, J=8 Hz, 2H), 7.35(d, J=8 Hz, 2H), 7.30–7.15(m, 2H), 6.51(dd, J=2,15 Hz, 1H), 5.38–5.28(m, 1H), 5.07–4.98(m, 1H), 4.13–3.95(m, 2H), 3.85–3.20(m, 6H), 2.00–1.79(m, 4H). ESI-MS: m/z 616(M+1)

EXAMPLE 60

5-Chloro-N-[(1S)-2-[(2-{4-[(3,5-dichloro-2-pyridyl)oxy]-1-piperidinyl}-2-oxoethyl)amino]-2-oxo-1-(2-pyridylmethyl)ethyl]-1-benzofuran-2-carboxamide The title compound was obtained from 3,5-dichloro-2-(4-piperidinyloxy)pyridine dihydrochloride and {[(2S)-2-{[(5-chloro-1-benzofuran-2-yl)carbonyl]amino}-3-(2-pyridyl)propanoyl]-amino}acetic acid in the same manner as in Example 59.

ESI-MS: m/z 630(M+1) $^1$H-NMR (300 MHz, CDCl$_3$) δ 8.85–8.70(m, 1H), 8.67–8.59(m, 1H), 8.22–8.10(m, 1H), 7.96(d, J=2 Hz, 1H), 7.70–7.60(m, 3H), 7.49(d, J=8 Hz, 1H), 7.42(s, 1H), 7.39(dd, J=8,2 Hz, 1H), 7.32–7.16(m, 2H), 5.39–5.28(m, 1H), 5.17–5.06(m, 1H), 4.15–3.98(m, 2H), 3.83–3.28(m, 6H), 2.01–1.79(m, 4H).

Preparation 39 tert-Butyl 4-{[3-(trifluoromethyl)-2-pyridyl]oxy}-1-piperidinecarboxylate

The title compound was obtained from tert-butyl 4-hydroxy-1-piperidinecarboxylate and 3-(trifluoromethyl)-2-hydroxypyridine in the same manner as in Preparation 13.

$^1$H-NMR (300 MHz, CDCl$_3$) δ 8.33–8.24(m, 1H), 7.90–7.81(m, 1H), 6.99–6.90(m, 1H), 5.48–5.33(m, 1H), 3.63–3.44(m, 4H), 1.99–1.77(m, 4H), 1.47(s, 9H).

EXAMPLE 61

(2E)-3-(4-Chlorophenyl)-N-[(1S)-2-oxo-2-{[2-oxo-2-(4-{[3-(trifluoromethyl)-2-pyridyl]oxy}-1-piperidinyl)ethyl]amino}-1-(2-pyridylmethyl)ethyl]-2-propenamide The title compound was obtained from tert-butyl 4-{[3-(trifluoromethyl)-2-pyridyl]oxy}-1-piperidinecarboxylate and {[(2S)-2-{[(2E)-3-(4-chlorophenyl)-2-propenoyl]amino}-3-(2-pyridyl)propanoyl]amino}acetic acid in the same manner as in Example 1.

ESI-MS: m/z 616(M+1) $^1$H-NMR (300 MHz, CDCl$_3$) δ 8.59–8.53(m, 1H)., 8.30–8.25(m, 1H), 8.06–7.83(m, 3H), 7.66–7.55(m, 2H), 7.45(d, J=8 Hz, 2H), 7.35(d, J=8 Hz, 2H), 7.29–7.14(m, 2H), 7.00–6.93(m, 1H), 6.50(dd, J=15,3 Hz, 1H), 5.55–5.45(m, 1H), 5.06–4.98(m, 1H), 4.14–3.90(m, 3H), 3.60–3.35(m, 4H), 3.30–3.20(m, 1H), 2.00–1.79(m, 4H).

EXAMPLE 62

5-Chloro-N-[(1S)-2-oxo-2-{[2-oxo-2-(4-{[3-(trifluoromethyl)-2-pyridyl]oxy}-1-piperidinyl)ethyl]amino}-1-(2-pyridylmethyl)ethyl]-1-benzofuran-2-carboxamide The title compound was obtained from tert-butyl 4-{[3-(trifluoromethyl)-2-pyridyl]oxy}-1-piperidinecarboxylate and {[(2S)-2-{[(5-chloro-1-benzofuran-2-yl)carbonyl]amino}-3-(2-pyridyl)propanoyl]amino}acetic acid in the same manner as in Example 1.

ESI-MS: m/z 630(M+1) $^1$H-NMR (300 MHz, CDCl$_3$) δ 8.85–8.67(m, 1H), 8.62(d, J=5 Hz, 1H), 8.28(d, J=5 Hz, 1H), 8.20–8.07(m, 1H), 7.86(d, J=8 Hz, 1H), 7.69–7.59(m, 2H), 7.49(d, J=8 Hz, 1H), 7.42(s, 1H), 7.38(dd, J=8,2 Hz, 1H), 7.30–7.15(m, 2H), 7.00–6.92(m, 1H), 5.50(br s, 1H), 5.16–5.05(m, 1H), 4.16–3.89(m, 3H), 3.61–3.27(m, 5H), 2.00–1.79(m, 4H).

Preparation 40

4-(4-Fluorophenoxy)piperidine

To a solution of tert-butyl 4-hydroxy-1-piperidinecarboxylate (2.0 g), 4-fluorophenol (1.1 g) and triphenylphosphine (3.9 g) in tetrahydrofuran was slowly added diethyl azodicarboxylate (2.6 g) at 8° C., and the mixture was stirred at room temperature for 4 hours. The reaction mixture was concentrated in vacuo to give the crude product.

To a solution of the crude product in ethyl acetate (5 ml) and methanol (5 ml) was added 4N hydrogen chloride in ethyl acetate (25 ml) at 8° C. The mixture was stirred at room temperature for 1 hour. The reaction mixture was poured into saturated aqueous sodium hydrogencarbonate solution and extracted with ethyl acetate. The organic layer was dried over anhydrous magnesium sulfate and concentrated in vacuo to give the title compound (1.08 g).

EXAMPLE 63

(2E)-3-(4-Chlorophenyl)-N-[(1S)-2-({2-[4-(4-fluorophenoxy)-1-piperidinyl]-2-oxoethyl}amino)-2-oxo-1-(2-pyridylmethyl)ethyl]-2-propenamide The title compound was obtained from 4-(4-fluorophenoxy)piperidine and {[(2S)-2-{[(2E)-3-(4-chlorophenyl)-2-propenoyl]amino}-3-(2-pyridyl)propanoyl]amino}-acetic acid in the same manner as in Example 59.

ESI-MS: m/z 565(M+1) $^1$H-NMR (300 MHz, CDCl$_3$) δ 8.60–8.53(m, 1H), 8.07–7.85(2H, m), 7.68–7.56(m, 2H), 7.45(d, J=8 Hz, 2H), 7.35(d, J=8 Hz, 2H), 7.31–7.15(m, 2H), 7.04–6.93(m, 2H), 6.90–6.80(m, 2H), 6.50(dd, J=15,2 Hz, 1H), 5.06–4.97(m, 1H), 4.50–4.40(m, 1H), 4.11–3.95(m, 2H), 3.79–3.20(m, 6H), 1.94–1.75(m, 4H).

EXAMPLE 64

5-Chloro-N-[(1S)-2-({2-[4-(4-fluorophenoxy)-1-piperidinyl]-2-oxoethyl}amino)-2-oxo-1-(2-pyridylmethyl)ethyl]-1-benzofuran-2-carboxamide The title compound was obtained from 4-(4-fluorophenoxy)piperidine and {[(2S)-2-{[(5-chloro-1-benzofuran-2-yl)carbonyl]amino}-3-(2-pyridyl)propanoyl]amino}acetic acid in the same manner as in Example 59.

ESI-MS: m/z 579(M+1) $^1$H-NMR (300 MHz, CDCl$_3$) δ 8.85–8.70(m, 1H), 8.67–8.60(m, 1H), 8.22–8.09(m, 1H), 7.70–7.60(m, 2H), 7.49(d, J=8 Hz, 1H), 7.42(s, 1H), 7.39 (dd, J=2,8 Hz, 1H), 7.32–7.16(m, 2H), 7.04–6.92(m, 2H), 6.90–6.80(m, 2H), 5.16–5.06(m, 1H), 4.51–4.40(m, 1H), 4.15–3.96(m, 2H), 3.75–3.44(m, 4H), 3.40–3.26(m, 2H), 1.95–1.73(m, 4H).

Preparation 41

4-[4-(Trifluoromethyl)phenoxy]piperidine hydrochloride

The title compound was obtained from tert-butyl 4-hydroxy-1-piperidinecarboxylate and 4-(trifluoromethyl)phenol in the same manner as in Preparation 38.

$^1$H-NMR (300 MHz, DMSO-d$_6$) δ 7.67(d, J=8 Hz, 2H), 7.19(d, J=8 Hz, 2H), 4.85–4.737(m, 1H), 3.29–3.00(m, 4H), 2.20–2.05(m, 2H), 1.98–1.78(m, 2H).

EXAMPLE 65

(2E)-3-(4-Chlorophenyl)-N-[(1S)-2-oxo-2-[(2-oxo-2-{4-[4-(trifluoromethyl)phenoxy]-1-piperidinyl}ethyl)amino]-1-(2-pyridylmethyl)ethyl]-2-propenamide The title compound was obtained from 4-[4-(trifluoromethyl)phenoxy]piperidine hydrochloride and {[(2S)-2-{[(2E)-3-(4-chlorophenyl)-2-propenoyl]amino}-3-(2-pyridyl)propanoyl]amino}acetic acid in the same manner as in Example 59.

ESI-MS: m/z 615(M+1) $^1$H-NMR (300 MHz, CDCl$_3$) δ 8.60–8.53(m, 1H), 8.10–7.85(m, 2H), 7.68–7.51(m, 4H), 7.45(d, J=8 Hz, 2H), 7.35(d, J=8 Hz, 2H), 7.30–7.15(m, 2H), 6.95(d, J=8 Hz, 2H), 6.50(dd, J=15,2 Hz, 1H), 5.07–4.97(m, 1H), 4.68–4.58(m, 1H), 4.09–3.97(m, 2H), 3.86–3.20(m, 6H), 1.99–1.78(m, 4H).

EXAMPLE 66

5-Chloro-N-[(1S)-2-oxo-2-[(2-oxo-2-{4-[4-(trifluoromethyl)phenoxy]-1-piperidinyl}ethyl)amino]-1-(2-pyridylmethyl)ethyl]-1-benzofuran-2-carboxamide The title compound was obtained from 4-[4-(trifluoromethyl)phenoxy]piperidine hydrochloride and {[(2S)-2-{[(5-chloro-1-benzofuran-2-yl)carbonyl]amino}-3-(2-pyridyl)propanoyl]amino}acetic acid in the same manner as in Example 59.

ESI-MS: m/z 629(M+1) $^1$H-NMR (300 MHz, CDCl$_3$) δ 8.85–8.71(m, 1H), 8.66–8.59(m, 1H), 8.24–8.10(m, 1H), 7.70–7.60(m, 2H), 7.55(d, J=8 Hz, 2H), 7.50(d, J=8 Hz, 1H), 7.43(s, 1H), 7.39(dd, J=8,2 Hz, 1H), 7.33–7.16(m, 2H), 6.95(d, J=8 Hz, 2H), 5.16–5.06(m, 1H), 4.69–4.59(m, 1H), 4.15–3.97(m, 2H), 3.87–3.29(m, 6H), 2.00–1.77(m, 4H).

Preparation 42 tert-Butyl 4-(4-chlorophenoxy)-1-piperidinecarboxylate

The title compound was obtained from tert-butyl 4-hydroxy-1-piperidinecarboxylate and 4-chlorophenol in the same manner as in Preparation 13.

$^1$H-NMR (300 MHz, CDCl$_3$) δ 7.31–7.14(m, 2H), 6.74–6.60(m, 2H), 4.47–4.36(m, 1H), 3.75–3.61(m, 2H), 3.40–3.26(m, 2H), 1.97–1.84(m, 2H), 1.80–1.66(m, 2H), 1.47(s, 9H).

EXAMPLE 67

(2E)-3-(4-Chlorophenyl)-N-[(1S)-2-({2-[4-(4-chlorophenoxy)-1-piperidinyl]-2-oxoethyl}amino)-2-oxo-1-(2-pyridylmethyl)ethyl]-2-propenamide The title compound was obtained from tert-butyl 4-(4-chlorophenoxy)-1-piperidinecarboxylate and {[(2S)-2-{[(2E)-3-(4-chlorophenyl)-2-propenoyl]amino}-3-(2-pyridyl)-propanoyl]-amino}acetic acid in the same manner as in Example 1.

ESI-MS: m/z 581(M+1) $^1$H-NMR (300 MHz, CDCl$_3$) δ 8.60–8.51(m, 1H), 8.09–7.84(m, 2H), 7.68–7.55(m, 2H), 7.45(d, J=8 Hz, 2H), 7.35(d, J=8 Hz, 2H), 7.30–7.14(m, 4H), 6.83(d, J=8 Hz, 2H), 6.50(d, J=15 Hz, 1H), 5.05–4.97(m, 1H), 4.55–4.45(m, 1H), 4.11–3.94(m, 2H), 3.80–3.20(m, 6H), 1.91–1.73(m, 4H).

EXAMPLE 68

5-Chloro-N-[(1S)-2-({2-[4-(4-chlorophenoxy)-1-piperidinyl]-2-oxoethyl}amino)-2-oxo-1-(2-pyridylmethyl)ethyl]-1-benzofuran-2-carboxamide The title compound was obtained from tert-butyl 4-(4-chlorophenoxy)-1-piperidinecarboxylate and {[(2S)-2-([(5-chloro-1-benzofuran-2-yl)carbonyl]amino}-3-(2-pyridyl)propanoyl]-amino}acetic acid in the same manner as in Example 1.

ESI-MS: m/z 595(M+1) $^1$H-NMR (300 MHz, CDCl$_3$) δ 8.85–8.70(m, 1H), 8.65–8.60(m, 1H), 8.23–8.10(m, 1H), 7.70–7.60(m, 2H), 7.50(d, J=8 Hz, 1H), 7.42(s, 1H), 7.39 (dd, J=8,2 Hz, 1H), 7.17–7.31(m, 4H), 6.88(d, J=8 Hz, 2H), 5.15–5.06(m, 1H), 4.55–4.46(m, 1H), 4.15–3.97(m, 2H), 3.29–3.28(m, 6H), 1.95–1.74(m, 4H).

Preparation 43 tert-Butyl 4-(2-pyridylthio)-1-piperidinecarboxylate

To a slurry of sodium hydride (about 60% oil suspension, 397 mg) in dimethoxyethane (4 ml) was added a solution of 2-pyridinethiol (1.05 g) in dimethoxyethane (6 ml) at 0° C., and the mixture was stirred at room temperature for 1 hour. To the mixture was added tert-butyl 4-bromo-1-piperidinecarboxylate (2.74 g), and the mixture was refluxed for 2 hours. After cooling, the resulting suspension was diluted with ether and filtered through a pad of Celite. The filtrate was washed with brine, dried over anhydrous magnesium sulfate and concentrated in vacuo. The residue was purified by silica gel column chromatography (eluent; 14% ethyl acetate in n-hexane) to give the title compound (2.2 g) as a white solid.

ESI-MS: 295.1(M+H) $^1$H-NMR (300 MHz, CDCl$_3$) δ 8.42(dd, J=5,2 Hz, 1H), 7.47(td, J=8,2 Hz, 1H), 7.16(d, J=8 Hz, 1H), 6.99(dd, J=8,5 Hz, 1H), 4.06–3.83(m, 3H), 3.16–3.02(m, 2H), 2.12–2.00(m, 2H), 1.71–1.56(m, 2H), 1.46(s, 9H).

EXAMPLE 69

(2E)-3-(4-Chlorophenyl)-N-[(1S)-2-oxo-2-({2-oxo-2-[4-(2-pyridylthio)-1-piperidinyl]ethyl}amino)-1-(2-pyridylmethyl)ethyl]-2-propenamide The title compound was obtained from tert-butyl 4-(2-pyridylthio)-1-piperidinecarboxylate and {[(2S)-2-{[(2E)-3-(4-chlorophenyl)-2-propenoyl]amino}-3-(2-pyridyl)propanoyl]amino}-acetic acid in the same manner as in Example 1.

ESI-MS: 564.2(M+H) $^1$H-NMR (300 MHz, CDCl$_3$) δ 8.55(dd, J=5,2 Hz, 1H), 8.41(dd, J=5,2 Hz, 1H), 8.02–7.96 (m, 1H), 7.95–7.88(m, 1H), 7.63(td, J=8,2 Hz, 1H), 7.61(d, J=16 Hz, 1H), 7.52–7.42(m, 3H), 7.35(d, J=8 Hz, 2H), 7.28–7.23(m, 1H), 7.18(dd, J=8,5 Hz, 1H), 7.15(d, J=8 Hz, 1H), 7.00(dd, J=8,5 Hz, 1H), 6.50(d, J=16 Hz, 1H), 5.06–4.97(m, 1H), 4.26–4.04(m, 2H), 4.02(app d, J=4 Hz, 2H), 3.70–3.59(m, 1H), 3.43(dd, J=15,5 Hz, 1H), 3.30–3.10 (m, 3H), 2.19–2.02(m, 2H), 1.73–1.54(m, 2H).

EXAMPLE 70

5-Chloro-N-[(1S)-2-oxo-2-({2-oxo-2-[4-(2-pyridylthio)-1-piperidinyl]ethyl}amino)-1-(2-pyridylmethyl)ethyl]-1-benzofuran-2-carboxamide The title compound was obtained from tert-butyl 4-(2-pyridylthio)-1-piperidinecarboxylate and {[(2S)-2-{[(5-chloro-1-benzofuran-2-yl)carbonyl]amino}-3-(2-pyridyl)propanoyl]amino}-acetic acid in the same manner as in Example 1.

ESI-MS: 578.1(M+H) $^1$H-NMR (300 MHz, CDCl$_3$) δ 8.80–8.73(m, 1H), 8.62(dd, J=5,2 Hz, 1H), 8.41(dd, J=5,2 Hz, 1H), 8.18–8.10(m, 1H), 7.65(td, J=8,2 Hz, 1H), 7.65(d, J=2 Hz, 1H), 7.51–7.44(m, 2H), 7.42(s, 1H), 7.38(dd, J=9,2 Hz, 1H), 7.27(d, J=8 Hz, 1H), 7.20(dd, J=8,5 Hz, 1H), 7.15(d, J=8 Hz, 1H), 6.99(dd, J=8,5 Hz, 1H), 5.15–5.06(m, 1H), 4.25–4.00(m, 4H), 3.71–3.59(m, 1H), 3.49(dd, J=15,5 Hz, 1H), 3.38–3.09(m, 3H), 2.19–2.01(m, 2H), 1.73–1.52 (m, 2H).

EXAMPLE 71

(2E)-3-(4-Chlorophenyl)-N-[(1S)-2-oxo-2-({2-oxo-2-[4-(2-pyridylsulfonyl)-1-piperidinyl]ethyl}amino)-1-(2-pyridylmethyl)ethyl]-2-propenamide The title compound was obtained from 2-(4-piperidinylsulfonyl)pyridine hydrochloride and {[(2S)-2-{[(2E)-3-(4-chlorophenyl)-2-propenoyl]amino}-3-(2-pyridyl)propanoyl]-amino}acetic acid in the same manner as in Example 59.

ESI-MS: 596.2(M+H). $^1$H-NMR (300 MHz, CDCl$_3$) δ 8.75–8.80(m, 1H), 8.58–8.52(m, 1H), 8.12–7.82(m, 4H), 7.68–7.55(m, 3H), 7.45(d, J=8 Hz, 2H), 7.35(d, J=8 Hz, 2H), 7.28–7.15(m, 2H), 6.54–6.44(m, 1H), 5.04–4.96(m, 1H), 4.68–4.56(m, 1H), 3.99(app d, J=4 Hz, 2H), 3.88–3.67(m, 2H), 3.47–3.35(m, 1H), 3.29–3.19(m, 1H), 3.11–2.97(m, 1H), 2.74–2.61(m, 1H), 2.12–1.90(m, 2H), 1.86–1.68(m, 2H).

EXAMPLE 72

5-Chloro-N-[(1S)-2-oxo-2-({2-oxo-2-[4-(2-pyridylsulfonyl)-1-piperidinyl]ethyl}amino)-1-(2-pyridylmethyl)ethyl]-1-benzofuran-2-carboxamide The title compound was obtained from 2-(4-piperidinylsulfonyl)pyridine hydrochloride and {[(2S)-2-{[(5-chloro-1-benzofuran-2-yl)carbonyl]amino}-3-(2-pyridyl)propanoyl]amino}acetic acid in the same manner as in Example 59.

ESI-MS: 578.1(M+H) $^1$H-NMR (300 MHz, CDCl$_3$) δ 8.85–8.57(m, 3H), 8.23–7.95(m, 3H), 7.69–7.55(m, 3H), 7.49(d, J=9 Hz, 1H), 7.42(s, 1H), 7.38(dd, J=9,2 Hz, 1H), 7.29–7.16(m, 2H), 3.52–3.42(m, 1H), 3.37–3.26(m, 1H), 3.12–2.99(m, 1H), 2.74–2.61(m, 1H), 2.13–1.91(m, 2H), 1.88–1.65(m, 2H).

Preparation 44 tert-Butyl 4-[(5-chloro-2-pyridyl)thio]-1-piperidinecarboxylate

The title compound was obtained from tert-butyl 4-mercapto-1-piperidinecarboxylate and 2,5-dichloropyridine in the same manner as in Preparation 7.

$^1$H-NMR (300 MHz, CDCl$_3$) δ 8.38(dd, J=2,1 Hz, 1H), 7.45(dd, J=8,2 Hz, 1H), 7.10(dd, J=8,1 Hz, 1H), 4.01–3.85 (m, 3H), 3.14–3.00(m, 2H), 2.10–1.98(m, 2H), 1.70–1.58 (m, 2H), 1.46(s, 9H).

EXAMPLE 73

(2E)-3-(4-Chlorophenyl)-N-[(1S)-2-[(2-{4-[(5-chloro-2-pyridyl)thio]-1-piperidinyl}-2-oxoethyl)amino]-2-oxo-1-(2-pyridylmethyl)ethyl]-2-propenamide The title compound was obtained from tert-butyl 4-[(5-chloro-2-pyridyl)thio]-1-piperidinecarboxylate and {[(2S)-2-{[(2E)-3-(4-chlorophenyl)-2-propenoyl]amino}-3-(2-pyridyl)-propanoyl}amino]acetic acid in the same-manner as in Example 1.

ESI-MS: 598.1(M+H) $^1$H-NMR (300 MHz, CDCl$_3$) δ 8.56(dd, J=5,2 Hz, 1H), 8.37(d, J=2 Hz, 1H), 8.03–7.97(m, 1H), 7.95–7.89(m, 1H), 7.63(td, J=8,2 Hz, 1H), 7.61(d, J=16 Hz, 1H), 7.49–7.42(m, 3H), 7.35(d, J=8 Hz, 2H), 7.28–7.23 (m, 1H), 7.18(dd, J=8,5 Hz, 1H), 7.09(d, J=8 Hz, 1H), 6.50(d, J=16 Hz, 1H), 5.06–4.97(m, 1H), 4.27–4.14(m, 1H), 4.10–3.97(m, 3H), 3.70–3.58(m, 1H), 3.43(dd, J=15,5 Hz, 1H), 3.30–3.07(m, 3H), 2.17–2.00(m, 2H), 1.72–1.54(m, 2H).

EXAMPLE 74

5-Chloro-N-[(1S)-2-[(2-{4-[(5-chloro-2-pyridyl)thio]-1-piperidinyl}-2-oxoethyl)amino]-2-oxo-1-(2-pyridylmethyl) ethyl]-1-benzofuran-2-carboxamide The title compound was obtained from tert-butyl 4-[(5-chloro-2-pyridyl)thio]-1-piperidinecarboxylate and {[(2S)-

2-([[(5-chloro-1-benzofuran-2-yl)carbonyl]amino}-3-(2-py-ridyl)propanoyl]amino}acetic acid in the same manner as in Example 1.

ESI-MS: 612.1(M+H) $^1$H-NMR (300 MHz, CDCl$_3$) δ 8.81–8.73(m, 1H), 8.62(dd, J=5,2 Hz, 1H), 8.37(d, J=2 Hz, 1H), 8.19–8.12(m, 1H), 7.65(td, J=8,2 Hz, 1H), 7.65(d, J=2 Hz, 1H), 7.52–7.35(m, 4H), 7.30–7.24(m, 1H), 7.20(dd, J=8,5 Hz, 1H), 7.09(d, J=8 Hz, 1H), 5.15–5.07(m, 1H), 4.26–4.14(m, 1H), 4.10–3.97(m, 3H), 3.71–3.60(m, 1H), 3.49(dd, J=15,4 Hz, 1H), 3.38–3.07(m, 3H), 2.18–2.01(m, 2H), 1.72–1.53(m, 2H).

EXAMPLE 75

(2E)-3-(4-Chlorophenyl)-N-[(1S)-2-oxo-2-({2-oxo-2-[4-(4-pyridylthio)-1-piperidinyl]ethyl}amino)-1-(2-pyridylmethyl)ethyl]-2-propenamide The title compound was obtained from 4-(4-piperidinylthio)pyridine dihydrochloride and {[(2S)-2-{[(2E)-3-(4-chlorophenyl)-2-propenoyl]amino}-3-(2-pyridyl)propanoyl]amino}acetic acid in the same manner as in Example 59.

ESI-MS: 564.2(M+H) $^1$H-NMR (300 MHz, CDCl$_3$) δ 8.56(dd, J=5,2 Hz, 1H), 8.45(d, J=6 Hz, 2H), 8.08–7.88(m, 1H), 7.65(td, J=8,2 Hz, 1H), 7.62(d, J=16 Hz, 1H), 7.47(d, J=8 Hz, 2H), 7.36(d, J=8 Hz, 2H), 7.29–7.24(m, 1H), 7.20(dd, J=8,5 Hz, 1H), 7.15(d, J=6 Hz, 1H), 6.50(d, J=16 Hz, 1H), 5.06–4.97(m, 1H), 4.27–4.13(m, 1H), 4.03(app d, J=4 Hz, 2H), 3.75–3.52(m, 2H), 3.49–3.39(m, 1H), 3.31–3.11(m; 3H), 2.14–2.01(m, 2H), 1.72–1.55(m, 2H).

EXAMPLE 76

5-Chloro-N-[(1S)-2-oxo-2-({2-oxo-2-[4-(4-pyridylthio)-1-piperidinyl]ethyl}amino)-1-(2-pyridylmethyl)ethyl]-1-benzofuran-2-carboxamide The title compound was obtained from 4-(4-piperidinylthio)pyridine dihydrochloride and {[(2S)-2-{[(5-chloro-1-benzofuran-2-yl)carbonyl]amino}-3-(2-pyridyl)propanoyl]amino}acetic acid in the same manner as in Example 59.

ESI-MS: 578.1(M+H) $^1$H-NMR (300 MHz, CDCl$_3$) δ 8.82–8.72(m, 1H), 8.62(dd, J=5,2 Hz, 1H), 8.44(d, J=6 Hz, 2H), 8.22–8.12(m, 1H), 7.65(td, J=8,2 Hz, 1H), 7.65(d, J=2 Hz, 1H), 7.49(d, J=9 Hz, 1H), 7.42(s, 1H), 7.39(dd, J=9,2 Hz, 1H), 7.27(d, J=8 Hz, 1H), 7.20(dd, J=8,5 Hz, 1H), 7.14(d, J=6 Hz, 1H), 5.14–5.06(m, 1H), 4.25–4.12(m, 1H), 4.05(app d, J=4 Hz, 2H), 3.75–3.43(m, 3H), 3.38–3.10(m, 3H), 2.14–2.01(m, 2H), 1.73–1.55(m, 2H).

Preparation 45 tert-Butyl 4-[(4-chlorophenyl)thio]-1-piperidinecarboxylate

The title compound was obtained from tert-butyl 4-bromo-1-piperidinecarboxylate and 4-chlorobenzenethiol in the same manner as in Preparation 7.

$^1$H-NMR (300 MHz, CDCl$_3$) δ 7.39–7.24(m, 4H), 4.07–3.84(m, 2H), 3.23–3.10(m, 1H), 3.00–2.80(m, 2H), 2.00–1.80(m, 2H), 1.61–1.30(m, 11H).

EXAMPLE 77

(2E)-3-(4-Chlorophenyl)-N-[(1S)-2-[(2-{4-[(4-chlorophenyl)thio]-1-piperidinyl}-2-oxoethyl)amino]-2-oxo-1-(2-pyridylmethyl)ethyl]-2-propenamide The title compound was obtained from tert-butyl 4-[(4-chlorophenyl)thio]-1-piperidinecarboxylate and {[(2S)-2-{[(2E)-3-(4-chlorophenyl)-2-propenoyl]amino}-3-(2-pyridyl)-propanoyl]amino}acetic acid in the same manner as in Example 1.

ESI-MS: 597.2(M+H) $^1$H-NMR (300 MHz, CDCl$_3$) δ 8.55(dd, J=5,2 Hz, 1H), 8.03–7.85(m, 2H), 7.63(td, J=8,2 Hz, 1H), 7.60(d, 16 Hz, 1H), 7.45(d, J=8 Hz, 2H), 7.37–7.22 (m, 7H), 7.18(dd, J=8,5 Hz, 1H), 6.49(d, J=16 Hz, 1H), 5.04–4.96(m, 1H), 4.30–4.16(m, 1H), 3.99(app d, d=4 Hz, 2H), 3.71–3.59(m, 1H), 3.47–3.37(m, 1H), 3.29–3.16(m, 2H), 3.15–2.91(m, 2H), 2.00–1.88(m, 2H), 1.59–1.42(m, 2H).

EXAMPLE 78

5-Chloro-N-[(1S)-2-[(2-{4-[(4-chlorophenyl)thio]-1-piperidinyl}-2-oxoethyl)amino]-2-oxo-1-(2-pyridylmethyl)ethyl]-1-benzofuran-2-carboxamide The title compound was obtained from tert-butyl 4-[(4-chlorophenyl)thio]-1-piperidinecarboxylate and {[(2S)-2-{[(5-chloro-1-benzofuran-2-yl)carbonyl]amino}-3-(2-pyridyl)propanoyl]-amino}acetic acid in the same manner as in Example 1.

ESI-MS: 611.1(M+H) $^1$H-NMR (300 MHz, CDCl$_3$) δ 8.80–8.71(m, 1H), 8.61(dd, J=5,2 Hz, 1H), 8.18–8.08(m, 1H), 7.65(td, J=8,2 Hz, 1H), 7.65(d, J=2 Hz, 1H), 7.48(d, J=9 Hz, 1H), 7.41(s, 1H), 7.40–7.15(m, 7H), 5.13–5.04(m, 1H), 4.29–4.17(m, 1H), 4.02(app d, J=4 Hz, 2H), 3.71–3.60 (m, 1H), 3.48(dd, J=15,4 Hz, 1H), 3.38–3.16(m, 2H), 3.16–2.92(m, 2H), 2.01–1.87(m, 2H), 1.63–1.41(m, 2H).

EXAMPLE 79

(2E)-3-(4-Chlorophenyl)-N-[(1S)-2-[(2-{4-[(4-chlorophenyl)sulfonyl]-1-piperidinyl}-2-oxoethyl)amino]-2-oxo-1-(2-pyridylmethyl)ethyl]-2-propenamide The title compound was obtained from 4-[(4-chlorophenyl)sulfonyl]piperidine hydrochloride and {[(2S)-2-{[(2E)-3-(4-chlorophenyl)-2-propenoyl]amino}-3-(2-pyridyl)-propanoyl]amino}acetic acid in the same manner as in Example 59.

ESI-MS: 629.1(M+H) $^1$H-NMR (300 MHz, CDCl$_3$) δ 8.57–8.51(m, 1H), 8.05–7.83(m, 2H), 7.82–7.74(m, 2H), 7.67–7.52(m, 4H), 7.45(d, J=8 Hz, 2H), 7.35(d, J=8 Hz, 2H), 7.28–7.13(m, 2H), 6.53–6.43(m, 1H), 5.03–4.93(m, 1H), 4.71–4.57(m, 1H), 3.98(app d, J=4 Hz, 2H), 3.86–3.75(m, 1H), 3.46–3.34(m, 1H), 3.29–3.19(m, 1H), 3.16–2.90(m, 2H), 2.65–2.50(m, 1H), 2.15–1.95(m, 2H), 1.69–1.49(m, 2H).

EXAMPLE 80

5-Chloro-N-[(1S)-2-[(2-{4-[(4-chlorophenyl)sulfonyl]-1-piperidinyl}-2-oxoethyl)amino]-2-oxo-1-(2-pyridylmethyl)ethyl]-1-benzofuran-2-carboxamide The title compound was obtained from 4-[(4-chlorophenyl)sulfonyl]piperidine hydrochloride and {[(2S)-2-{[(5-chloro-1-benzofuran-2-yl)carbonyl]amino}-3-(2-pyridyl)propanoyl]-amino}acetic acid in the same manner as in Example 59.

ESI-MS: 643.1(M+H) $^1$H-NMR (300 MHz, CDCl$_3$) δ 8.83–8.67(m, 1H), 8.63–8.56(m, 1H), 8.22–8.09(m, 1H), 7.82–7.74(m, 2H), 7.69–7.34(m, 7H), 7.29–7.15(m, 2H), 5.13–5.03(m, 1H), 4.70–4.58(m, 1H), 4.09–3.91(m, 2H), 3.88–3.75(m, 1H), 3.52–3.40(m, 1H), 3.37–3.25(m, 1H), 3.17–2.91(m, 2H), 2.65–2.50(m, 1H), 2.15–1.96(m, 2H), 1.68–1.47(m, 2H).

The invention claimed is:

1. A compound of the formula (I):

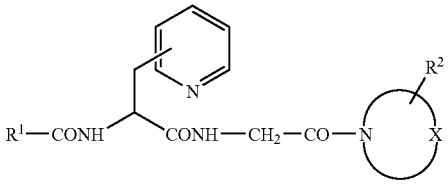

wherein

R¹ is benzofuranyl substituted by halogen, or styryl substituted by halogen;

R² is substituted hydroxy, substituted mercapto or substituted sulfonyl; and

X is

or pharmaceutically acceptable salts thereof.

2. The compound of claim 1, wherein R² is a group of the formula:
—Y—R³ wherein R³ is lower alkyl, halo(lower)alkyl, optionally substituted heterocyclic group or optionally substituted aryl, and Y is —O—, —S— or —SO₂—, or a pharmaceutically acceptable salt thereof.

3. The compound of claim 2, wherein R³ is lower alkyl; halo(lower)alkyl; heterocyclic group optionally substituted by one or more substituent(s) selected from the group consisting of lower alkyl, lower alkoxy, halogen and halo(lower)alkyl; or aryl optionally substituted by one or more substituent(s) selected from the group consisting of lower alkyl, lower alkoxy, halogen and halo(lower)alkyl, or a pharmaceutically acceptable salt thereof.

4. The compound of claim 3, wherein R³ is lower alkyl; halo(lower)alkyl; heterocyclic group selected from the group consisting of pyridyl, pyrazinyl, thiazolyl, pyridazinyl and pyrimidinyl, said heterocyclic group is optionally substituted by one or more substituent(s) selected from the group consisting of lower alkyl, lower alkoxy, halogen and halo(lower)alkyl; or phenyl optionally substituted by one or more substituent(s) selected from the group consisting of lower alkyl, lower alkoxy, halogen and halo(lower)alkyl, or a pharmaceutically acceptable salt thereof.

5. The compound of claim 1, wherein X is

or a pharmaceutically acceptable salt thereof.

6. The compound of claim 5, wherein R² is substituted hydroxy, or or a pharmaceutically acceptable salt thereof.

7. The compound of claim 6, wherein R² is a group of the formula:
—O—R³ wherein R³ is lower alkyl, halo(lower)alkyl, optionally substituted heterocyclic group or optionally substituted aryl, or a pharmaceutically acceptable salt thereof.

8. The compound of claim 7, wherein R³ is lower alkyl, halo(lower)alkyl, pyridyl, pyrazinyl, thiazolyl or phenyl, each of said pyridyl, pyrazinyl, thiazolyl and phenyl is optionally substituted by one or more substituents selected from the group consisting of lower alkyl, lower alkoxy, halogen and halo(lower)alkyl, or a pharmaceutically acceptable salt thereof.

9. The compound of claim 8, wherein R³ is lower alkyl, halo(lower)alkyl, pyridyl, pyrazinyl, thiazolyl or phenyl, said pyridyl is optionally substituted by a substituent selected from the group consisting of lower alkyl, lower alkoxy, halogen and halo(lower)alkyl, or a pharmaceutically acceptable salt thereof.

10. The compound of claim 1, wherein R¹ is benzofuranyl substituted by chlorine, or styryl substituted by chlorine, or a pharmaceutically acceptable salt thereof.

11. The compound of claim 1, wherein R¹ is 5-chloro-1-benzofuran-2-yl or 2-(4-chlorophenyl)ethenyl, or a pharmaceutically acceptable salt thereof.

12. The compound of claim 1, which is selected from the group consisting of:
(2E)-3-(4-Chlorophenyl)-N-[(1S)-2-oxo-2-({2-oxo-2-[4-(1,3-thiazol-2-yloxy)-1-piperidinyl]ethyl}amino)-1-(2-pyridylmethyl)ethyl]acrylamide;
5-Chloro-N-[(1S)-2-oxo-2-({2-oxo-2-[4-(1,3-thiazol-2-yloxy)-1-piperidinyl]ethyl}amino)-1-(2-pyridylmethyl)ethyl]-1-benzofuran-2-carboxamide;
(2E)-3-(4-Chlorophenyl)-N-[(1S)-2-oxo-2-({2-oxo-2-[4-(2-pyrazinyloxy)-1-piperidinyl]ethyl}amino)-1-(2-pyridylmethyl)ethyl]acrylamide;
5-Chloro-N-[(1S)-2-oxo-2-({2-oxo-2-[4-(2-pyrazinyloxy)-1-piperidinyl]ethyl}amino)-1-(2-pyridylmethyl)ethyl]-1-benzofuran-2-carboxamide;
(2E)-3-(4-Chlorophenyl)-N-[(1S)-2-oxo-2-({2-oxo-2-[4-(4-pyridyloxy)-1-piperidinyl]ethyl}amino)-1-(2-pyridylmethyl)ethyl]acrylamide;
5-Chloro-N-[(1S)-2-oxo-2-({2-oxo-2-[4-(4-pyridyloxy)-1-piperidinyl]ethyl}amino)-1-(2-pyridylmethyl)ethyl]-1-benzofuran-2-carboxamide;
(2E)-3-(4-Chlorophenyl)-N-[(1S)-2-oxo-2-({2-oxo-2-[4-(3-pyridyloxy)-1-piperidinyl]ethyl}amino)-1-(2-pyridylmethyl)ethyl]acrylamide;
5-Chloro-N-[(1S)-2-oxo-2-({2-oxo-2-[4-(3-pyridyloxy)-1-piperidinyl]ethyl})amino)-1-(2-pyridylmethyl)ethyl]-1-benzofuran-2-carboxamide;
(2E)-3-(4-Chlorophenyl)-N-[(1S)-2-[(2-{4-[(6-methoxy-2-pyridyl)oxy]-1-piperidinyl}-2-oxoethyl)amino]-2-oxo-1-(2-pyridylmethyl)ethyl]acrylamide;
5-Chloro-N-[(1 S)-2-[(2-{4-[(6-methoxy-2-pyridyl)oxy]-1-piperidinyl}-2-oxoethyl)amino]-2-oxo-1-(2-pyridylmethyl)ethyl]-1-benzofuran-2-carboxamide;
(2E)-3-(4-Chlorophenyl)-N-[(1S)-2-[(2-{3-[(5-chloro-2-pyridyl)oxy]-1-piperidinyl}-2-oxoethyl)amino]-2-oxo-1-(2-pyridylmethyl)ethyl]acrylamide;
5-Chloro-N-[(1S)-2-[(2-{3-[(5-chloro-2-pyridyl)oxy]-1-piperidinyl}-2-oxoethyl)amino]-2-oxo-1-(2-pyridylmethyl)ethyl]-1-benzofuran-2-carboxamide;
(2E)-3-(4-Chlorophenyl)-N-[(1S)-2-oxo-2-({2-oxo-2-[4-(2-pyridyloxy)-1-piperidinyl]ethyl}amino)-1-(2-pyridylmethyl)ethyl]acrylamide;
5-Chloro-N-[(1S)-2-oxo-2-({2-oxo-2-[4-(2-pyridyloxy)-1-piperidinyl]ethyl}amino)-1-(2-pyridylmethyl)ethyl]-1-benzofuran-2-carboxamide;

(2E)-3-(4-Chlorophenyl)-N-[(1S)-2-[(2-{4-[(6-methyl-2-pyridyl)oxy]-1-piperidinyl}-2-oxoethyl)amino]-2-oxo-1-(2-pyridylmethyl)ethyl]acrylamide;

5-Chloro-N-[(1S)-2-[(2-{4-[(6-methyl-2-pyridyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(6-chloro-2-pyridyl)oxy]-1-piperidinyl}-2-oxoethyl)amino]-2-oxo-1-(2-pyridylmethyl)ethyl]acrylamide;

5-Chloro-N-[(1S)-2-[(2-{4-[(6-chloro-2-pyridyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-oxo-2-{[2-oxo-2-(4-{[5-(trifluoromethyl)-2-pyridyl]oxy}-1-piperidinyl)ethyl]amino}-1-(2-pyridylmethyl)ethyl]acrylamide;

5-Chloro-N-[(1S)-2-oxo-2-{[2-oxo-2-(4-{[5-(trifluoromethyl)-2-pyridyl]oxy}-1-piperidinyl)ethyl]amino}-1-(2-pyridylmethyl)ethyl]-1-benzofuran-2-carboxamide;

(2E)-3-(4-Chlorophenyl)-N-[(1S)-2-[(2-{4-[(5-chloro-2-pyridyl)oxy]-1-piperidinyl}-2-oxoethyl)amino]-2-oxo-1-(2-pyridylmethyl)ethyl]acrylamide;

5-Chloro-N-[(1S)-2-[(2-{4-[(5-chloro-2-pyridyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-oxo-2-{[2-oxo-2-(4-phenoxy-1-piperidinyl)ethyl]amino}-1-(2-pyridylmethyl)ethyl]acrylamide;

5-Chloro-N-[(1S)-2-oxo-2-{[2-oxo-2-(4-phenoxy-1-piperidinyl)ethyl]amino}-1-(2-pyridylmethyl)ethyl]-1-benzofuran-2-carboxamide;

(2E)-3-(4-Chlorophenyl)-N-[(1S)-2-oxo-2-({2-oxo-2-[4-(2,2,2-trifluoroethoxy)-1-piperidinyl]ethyl}amino)-1-(2-pyridylmethyl)ethyl]acrylamide;

5-Chloro-N-[(1S)-2-oxo-2-({2-oxo-2-[4-(2,2,2-trifluoroethoxy)-1-piperidinyl]ethyl}amino)-1-(2-pyridytmethyl)ethyl]-1-benzofuran-2-carboxamide;

(2E)-3-(4-Chlorophenyl)-N-[(1S)-2-{[2-(4-isopropoxy-1-piperidinyl)-2-oxoethyl]amino}-2-oxo-1-(2-pyridylmethyl)ethyl]acrylamide;

5-Chloro-N-[(1S)-2-{[2-(4-isopropoxy-1-piperidinyl)-2-oxoethyl]amino}-2-oxo-1-(2-pyridylmethyl)ethyl]-1-benzofuran-2-carboxamide;

(2E)-N-[(1S)-2-{[2-(4-Butoxy-1-piperidinyl)-2-oxoethyl]amino}-2-oxo-1-(2-pyridylmethyl)ethyl]-3-(4-chlorophenyl)acrylamide;

N-[(1S)-2-{[2-(4-Butoxy-1-piperidinyl)-2-oxoethyl]amino}-2-oxo-1-(2-pyridylmethyl)ethyl]-5-chloro-1-benzofuran-2-carboxamide;

(2E)-3-(4-Chlorophenyl)-N-[(1S)-2-[(2-{4-[(6-chloro-2-pyrazinyl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(6-chloro-2-pyrazinyl)oxy]-1-piperidinyl}-2-oxoethyl)amino]-2-oxo-1-(2-pyridylmethyl)ethyl]-1-benzofaran-2-carboxamide;

(2E)-3-(4-Chlorophenyl)-N-[(1S)-2-[(2-{4-[(6-chloro-3-pyridazinyl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(6-chloro-3-pyridazinyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(6-methoxy-3-pyridazinyl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(6-methoxy-3-pyridazinyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(3-chloro-2-pyridyl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(3-chloro-2-pyridyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(6-chloro-4-pyrimidinyl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(6-chloro-4-pyrimidinyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-oxo-2-{[2-oxo-2-(4-{[6-(trifluoromethyl)-4-pyrimidinyl]oxy}-1-piperidinyl)ethyl]amino}-1-(2-pyridylmethyl)ethyl]-2-propenamide;

5-Chloro-N-[(1S)-2-oxo-2-{[2-oxo-2-(4-{[6-(trifluoromethyl)-4-pyrimidinyl]oxy}-1-piperidinyl)ethyl]amino}-1-(2-pyridylmethyl)ethyl]-1-benzofuran-2-carboxamide;

5-Chloro-N-[(1S)-2-oxo-2-{[2-oxo-2-(4-{[2-(trifluoromethyl)-4-pyrimidinyl]oxy}-1-piperidinyl)ethyl]amino}-1-(2-pyridylmethyl)ethyl]-1-benzofuran-2-carboxamide;

5-Chloro-N-[(1S)-2-[(2-{4-[(5-chloro-2-pyrazinyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(5-methyl-1,3-thiazol-2-yl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(5-methyl-1,3-thiazol-2-yl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(5-chloro-1,3-thiazol-2-yl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(5-chloro-1,3-thiazol-2-yl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{(3R)-3-[(5-chloro-2-pyridyl)oxy]-1-pyrrolidinyl}-2-oxoethyl)amino]-2-oxo-1-(2-pyridylmethyl)ethyl]-2-propenamide;

5-Chloro-N-[(1S)-2-[(2-{(3R)-3-[(5-chloro-2-pyridyl)oxy]-1-pyrrolidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{(3S)-3-[(5-chloro-2-pyridyl)oxy]-1-pyrrolidinyl}-2-oxoethyl)amino]-2-oxo-1-(2-pyridylmethyl)ethyl]-2-propenamide;

5-Chloro-N-[(1S)-2-[(2-{(3S)-3-[(5-chloro-2-pyridyl)oxy]-1-pyrrolidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{(3R)-3-[(6-chloro-2-pyrazinyl)oxy]-1-pyrrolidinyl}-2-oxoethyl)amino]-2-oxo-1-(2-pyridylmethyl)ethyl]-2-propenamide;

5-Chloro-N-[(1S)-2-[(2-{(3R)-3-[(6-chloro-2-pyrazinyl)oxy]-1-pyrrolidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{(3R)-3-[(5-methyl-1,3-thiazol-2-yl)oxy]-1-pyrrolidinyl}-2-oxoethyl)amino]-2-oxo-1-(2-pyridylmethyl)ethyl]-2-propenamide;

5-Chloro-N-[(1S)-2-[(2-{(3R)-3-[(5-methyl-1,3-thiazol-2-yl)oxy]-1-pyrrolidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-oxo-2-{[2-oxo-2-(3-{[6-(trifluoromethyl)-4-pyrimidinyl]oxy}-1-azetidinyl)ethyl]amino }-1-(2-pyridylmethyl)ethyl]-2-propenamide;

5-Chloro-N-[(1S)-2-oxo-2-{[2-oxo-2-(4-{[6-(tnfluoromethyl)-4-pyrimidinyl]oxy}-1-azetidinyl)ethyl] amino }-1-(2-pyridylmethyl)ethyl]-benzofuran-2-carboxamide;

(2E)-3-(4-Chlorophenyl)-N-[(1S)-2-[(2-{4-[(3,5-dichloro-2-pyridyl)oxy]-1-piperidinyl}-2-oxoethyl)amino]-2-oxo-1-(2-pyridylmethyl)ethyl]-2-propenamide;

5   -Chloro-N-[(1S)-2-[(2-{4-[(3,5-dichloro-2-pyridyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-oxo-2-{[2-oxo-2-(4-{[3-(trifluoromethyl)-2-pyridyl]oxy}-1-piperidinyl)ethyl]amino}-1-(2-pyridylmethyl)ethyl]-2-propenamide;

5-Chloro-N-[(1S)-2-oxo-2-{[2-oxo-2-(4-{[3-(trifluoromethyl)-2-pyridyl]oxy}-1-piperidinyl)ethyl]amino}-1-(2-pyridylmethyl)ethyl]-1-benzofiiran-2-carboxamide;

(2E)-3-(4-Chlorophenyl)-N-[(1S)-2-({2-[4-(4-fluorophenoxy)-1-piperidinyl]-2-oxoethyl}amino)-2-oxo-1-(2-pyridylmethyl)ethyl]-2-propenamide;

5   -Chloro-N-[(1S)-2-({2-[4-(4-fluorophenoxy)-1-piperidinyl]-2-oxoethyl}amino)-2-oxo-1-(2-pyridylmethyl)ethyl]-1-benzofuran-2-carboxamide;

(2E)-3-(4-Chlorophenyl)-N-[(1S)-2-oxo-2-[(2-oxo-2-{4-[4-(trifloromethyl)phenoxy]-1-piperidinyl}ethyl)amino]-1-(2-pyridylmethyl)ethyl]-2-propenamide;

5   -Chloro-N-[(1S)-2-oxo-2-[(2-oxo-2-{4-[4-(trifluoromethyl)phenoxy]-1-piperidinyl}ethyl)amino]-1-(2-pyridylmethyl)ethyl]-1-benzofuran-2-carboxamide;

(2E)-3-(4-Chlorophenyl)-N-[(1S)-2-({2-[4-(4-chlorophenoxy)-1-piperidinyl]-2-oxoethyl}amino)-2-oxo-1-(2-pyridylmethyl)ethyl]-2-propenamide;

5   -Chloro-N-[(1S)-2-({2-[4-(4-chlorophenoxy)-1-piperidinyl]-2-oxoethyl}amino)-2-oxo-1-(2-pyridylmethyl)ethyl]-1-benzofuran-2-carboxamide;

(2E)-3-(4-Chlorophenyl)-N-[(1S)-2-oxo-2-({2-oxo-2-[4-(2-pyridylthio)-1-piperidinyl]ethyl}amino)-1-(2-pyridylmethyl)ethyl]-2-propenamide;

5-Chloro-N-[(1S)-2-oxo-2-({2-oxo-2-[4-(2-pyridylthio)-1-piperidinyl]ethyl}amino)-1-(2-pyridylmethyl)ethyl]-1-benzofuran-2-carboxamide;

(2E)-3-(4-Chlorophenyl)-N-[(1S)-2-oxo-2-({2-oxo-2-[4-(2-pyridylsulfonyl)-1-piperidinyl]ethyl}amino)-1-(2-pyridylmethyl)ethyl]-2-propenamide;

5-Chloro-N-[(1S)-2-oxo-2-({2-oxo-2-[4-(2-pyridylsulfonyl)-1-piperidinyl]ethyl}amino)-1-(2-pyridylmethyl)ethyl]-1-benzofuran-2-carboxamide;

(2E)-3-(4-Chlorophenyl)-N-[(1S)-2-[(2-{4-[(5 -chloro-2-pyridyl)thio]-1-piperidinyl}-2-oxoethyl)amino]-2-oxo-1-(2-pyridylmethyl)ethyl]-2-propenamide;

5-Chloro-N-[(1S)-2-[(2-{4-[(5-chloro-2-pyridyl)thio]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-oxo-2-({2-oxo-2-[4-(4-pyridylthio)-1-piperidinyl]ethyl}amino)-1-(2-pyridylmethyl)ethyl]-2-propenamide;

5 -Chloro-N-[(1S)-2-oxo-2-({2-oxo-2-[4-(4-pyridylthio)-1-piperidinyl]ethyl}amino)-1-(2-pyridylmethyl)ethyl]-1-benzofuran-2-carboxamide;

(2E)-3-(4-Chlorophenyl)-N-[(1S)-2-[(2-{4-[(4-chlorophenyl)thio]-1-piperidinyl}-2-oxoethyl)amino]-2-oxo-1-(2-pyridylmethyl)ethyl]-2-propenamide;

5-Chloro-N-[(1S)-2-[(2-{4-[(4-chlorophenyl)thio]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(4-chlorophenyl)sulfonyl]-1-piperidinyl}-2-oxoethyl)amino]-2-oxo-1-(2-pyridylmethyl)ethyl]-2-propenamide;

5-Chloro-N-[(1S)-2-[(2-{4-[(4-chlorophenyl)sulfonyl]-1-piperidinyl}-2-oxoethyl)amino]-2-oxo-1-(2-pyridylmethyl)ethyl]-1-benzofuran-2-carboxamide; and pharmaceutically acceptable salts thereof.

13. The compound of claim 1, which is selected from the group consisting of:

5-Chloro-N-[(1S)-2-oxo-2-({2-oxo-2-[4-(1,3-thiazol-2-yloxy)-1-piperidinyl]ethyl}amino)-1-(2-pyridylmethyl)ethyl]-1-benzofuran-2-carboxamide;

(2E)-3-(4-Chlorophenyl)-N-[(1S)-2-oxo-2-({2-oxo-2-[4-(2-pyrazinyloxy)-1-piperidinyl]ethyl}amino)-1-(2-pyridylmethyl)ethyl]acrylamide;

5-Chloro-N-[(1S)-2-[(2-{4-[(6-methoxy-2-pyridyl)oxy]-1-piperidinyl}-2-oxoethyl)amino]-2-oxo-1-(2-pyridylmethyl)ethyl]-1-benzofuran-2-carboxamide;

5-Chloro-N-[(1S)-2-oxo-2-({2-oxo-2-[4-(2-pyridyloxy)-1-piperidinyl]ethyl}amino)-1-(2-pyridylmethyl)ethyl]-1-benzofuran-2-carboxamide;

(2E)-3-(4-Chlorophenyl)-N-[(1S)-2-oxo-2-{[2-oxo-2-(4-phenoxy-1-piperidinyl)ethyl]amino}-1-(2-pyridylmethyl)ethyl]acrylamide;

5-Chloro-N-[(1S)-2-oxo-2-({2-oxo-2-[4-(2,2,2-trifluoroethoxy)-1-piperidinyl]ethyl}amino)-1-(2-pyridylmethyl)ethyl]-1-benzofuran-2-carboxamide;

(2E)-3-(4-Chlorophenyl)-N-[(1S)-2-{[2-(4-isopropoxy-1-piperidinyl)-2-oxoethyl]amino }-2-oxo-1-(2-pyridylmethyl)ethyl]acrylamide; and pharmaceutically acceptable salts thereof.

14. A pharmaceutical composition comprising a compound of claim 1 or a pharmaceutically acceptable salt thereof in admixture with a pharmaceutically acceptable carrier.

15. A pharmaceutical composition comprising FK506 and a compound of claim 1 or a pharmaceutically acceptable salt thereof.

16. The pharmaceutical composition of claim 14, which comprises a compound selected from the group consisting of:

(2E)-3-(4-Chlorophenyl)-N-[(1S)-2-oxo-2-({2-oxo-2-[4-(1,3-thiazol-2-yloxy)-1-piperidinyl]ethyl }amino)-1-(2-pyridylmethyl)ethyl]acrylamide;

5-Chloro-N-[(1S)-2-oxo-2-({2-oxo-2-[4-(1,3-thiazol-2-yloxy)-1-piperidinyl]ethyl }amino)-1-(2-pyridylmethyl)ethyl]-1-benzofuran-2-carboxamide;

(2E)-3-(4-Chlorophenyl)-N-[(1S)-2-oxo-2-({2-oxo-2-[4-(2-pyrazinyloxy)-1-piperidinyl]ethyl}amino)-1-(2-pyridylmethyl)ethyl]acrylamide;

5-Chloro-N-[(1S)-2-oxo-2-({2-oxo-2-[4-(2-pyraziny-loxy)-1-piperidinyl]ethyl}amino)-1-(2-pyridylmethyl)ethyl]-1-benzofuran-2-carboxamide;

(2E)-3-(4-Chlorophenyl)-N-[(1S)-2-oxo-2-({2-oxo-2-[4-(4-pyridyloxy)-1-piperidinyl]ethyl}amino)-1-(2-pyridylmethyl)ethyl]acrylamide;

5-Chloro-N-[(1S)-2-oxo-2-({2-oxo-2-[4-(4-pyridyloxy)-1-piperidinyl]ethyl}amino)-1-(2-pyridylmethyl)ethyl]-1-benzofuran-2-carboxamide;

(2E)-3-(4-Chlorophenyl)-N-[(1S)-2-oxo-2-({2-oxo-2-[4-(3-pyridyloxy)-1-piperidinyl]ethyl}amino)-1-(2-pyridylmethyl)ethyl]acrylamide;

5-Chloro-N-[(1S)-2-oxo-2-({2-oxo-2-[4-(3-pyridyloxy)-1-pipendinyl]ethyl}amino)-1-(2-pyridylmethyl)ethyl]-1-benzofuran-2-carboxamide;

(2E)-3-(4-Chlorophenyl)-N-[(1S)-2-[(2-{4-[(6-methoxy-2-pyridyl)oxy]-1-piperidinyl}-2-oxoethyl)amino]-2-oxo-1-(2-pyridylmethyl)ethyl]acrylamide;

5-Chloro-N-[(1S)-2-[(2-{4-[(6-methoxy-2-pyridyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{3-[(5-chloro-2-pyridyl)oxy]-1-piperidinyl}-2-oxoethyl)amino]-2-oxo-1-(2-pyridylmethyl)ethyl]acrylamide;

5-Chloro-N-[(1S)-2-[(2-{3-[(5-chloro-2-pyridyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-oxo-2-({2-oxo-2-[4-(2-pyridyloxy)-1-piperidinyl]ethyl}amino)-1-(2-pyridtmethyl)ethyl]acrylamide;

5-Chloro-N-[(1S)-2-oxo-2-({2-oxo-2-[4-(2-pyridyloxy)-1-piperidinyl]ethyl}amino)-1-(2-pyridylmethyl)ethyl]-1-benzofuran-2-carboxamide;

(2E)-3-(4-Chlorophenyl)-N-[(1S)-2-[(2-{4-[(6-methyl-2-pyridyl)oxy]-1-piperidinyl}-2-oxoethyl)amino]-2-oxo-1-(2-pyridylmethyl)ethyl]acrylamide;

5-Chloro-N-[(1S)-2-[(2-{4-[(6-methyl-2-pyridyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(6-chloro-2-pyridyl)oxy]-1-piperidinyl}-2-oxoethyl)amino]-2-oxo-1-(2-pyridylmethyl)ethyl]acrylamide;

5-Chloro-N-[(1S)-2-[(2-{4-[(6-chloro-2-pyridyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-oxo-2-{[2-oxo-2-(4-{[5-(trifluoromethyl)-2-pyridyl]oxy}-1-piperidinyl)ethyl]amino}-1-(2-pyridylmethyl)ethyl]acrylamide;

5-Chloro-N-[(1S)-2-oxo-2-{[2-oxo-2-(4-{[5-(trifluoromethyl)-2-pyridyl]oxy}-1-piperidinyl)ethyl]amino}-1-(2-pyridylmethyl)ethyl]-1-benzofuran-2-carboxamide;

(2E)-3-(4-Chlorophenyl)-N-[(1S)-2-[(2-{4-[(5 -chloro-2-pyridyl)oxy]-1-piperidinyl}-2-oxoethyl)amino]-2-oxo-1-(2-pyridylmethyl)ethyl]acrylamide;

5-Chloro-N-[(1S)-2-[(2-{4-[(5-chloro-2-pyridyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-oxo-2-{[2-oxo-2-(4-phenoxy-1-piperidinyl)ethyl]amino}-1-(2-pyridylmethyl)ethyl]acrylamide;

5-Chloro-N-[(1S)-2-oxo-2-{[2-oxo-2-(4-phenoxy-1-piperidinyl)ethyl]amino}-1-(2-pyridylmethyl)ethyl]-1-benzofuran-2-carboxamide;

(2E)-3-(4-Chlorophenyl)-N-[(1S)-2-oxo-2-({2-oxo-2-[4-(2,2,2-trifluoroethoxy)-1-piperidinyl]ethyl}amino)-1-(2-pyridylmethyl)ethyl]acrylamide;

5-Chloro-N-[(1S)-2-oxo-2-({2-oxo-2-[4-(2,2,2-trifluoroethoxy)-1-piperidinyl]ethyl}amino)-1-(2-pyridylmethyl)ethyl]-1-benzofuran-2-carboxamide;

(2E)-3-(4-Chlorophenyl)-N-[(1S)-2-{[2-(4-isopropoxy-1-piperidinyl)-2-oxoethyl]amino }-2-oxo-1-(2-pyridylmethyl)ethyl]acrylamide;

5-Chloro-N-[(1S)-2-{[2-(4-isopropoxy-1-piperidinyl)-2-oxoethyl]amino}-2-oxo-1-(2-pyridylmethyl)ethyl]-1-benzofuran-2-carboxamide;

(2E)-N-[(1S)-2-{[2-(4-Butoxy-1-piperidinyl)-2-oxoethyl]amino }-2-oxo-1-(2-pyridylmethyl)ethyl]-3-(4-chlorophenyl)acrylamide;

N-[(1S)-2-{[2-(4-Butoxy-1-piperidinyl)-2-oxoethyl]amino}-2-oxo-1-(2-pyridylmethyl)ethyl]-5-chloro-1-benzofuran-2-carboxamide;

(2E)-3-(4-Chlorophenyl)-N-[(1S)-2-[(2-{4-[(6-chloro-2-pyrazinyl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(6-chloro-2-pyrazinyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(6-chloro-3-pyridazinyl)oxy]-1-piperidinyl}-2-oxoethyl)amino]-2-oxo-1-(2-pyridylmethyl)ethyl]-2-propenamide;

5 -Chloro-N-[(1S)-2-[(2-{4-[(6-chloro-3-pyridazinyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(6-methoxy-3-pyridazinyl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(6-methoxy-3-pyridazinyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(3-chloro-2-pyridyl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(3-chloro-2-pyridyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(6-chloro-4-pyrimidinyl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(6-chloro-4-pyrimidinyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-oxo-2-{[2-oxo-2-(4-{[6-(trifluoromethyl)-4-pyrimidinyl]oxy}-1-piperidinyl)ethyl]amino}-1-(2-pyridylmethyl)ethyl]-2-propenamide;

5 -Chloro-N-[(1S)-2-oxo-2-{[2-oxo-2-(4-{[6-(trifluoromethyl)-4-pyrimidinyl]oxy}-1-piperidinyl)ethyl]amino }-1-(2-pyridylmethyl)ethyl]-1-benzofuran-2-carboxamide;

5-Chloro-N-[(1S)-2-oxo-2-{[2-oxo-2-(4-{[2-(trifluoromethyl)-4-pyrimidinyl]oxy}-1-piperidinyl)ethyl]amino }-1-(2-pyridylmethyl)ethyl]-1-benzofuran-2-carboxamide;

5-Chloro-N-[(1S)-2-[(2-{4-[(5 -chloro-2-pyrazinyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(5-methyl-1,3-thiazol-2-yl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(5-methyl-1,3-thiazol-2-yl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(5-chloro-1,3-thiazol-2-yl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(5-chloro-1,3-thiazol-2-yl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{(3R)-3-[(5-chloro-2-pyridyl)oxy]-1-pyrrolidinyl}-2-oxoethyl)amino]-2-oxo-1-(2-pyridylmethyl)ethyl]-2-propenamide;

5-Chloro-N-[(1S)-2-[(2-{(3R)-3-[(5-chloro-2-pyridyl)oxy]-1-pyrrolidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{(3S)-3-[(5-chloro-2-pyridyl)oxy]-1-pyrrolidinyl}-2-oxoethyl)amino]-2-oxo-1-(2-pyridylmethyl)ethyl]-2-propenamide;

5-Chloro-N-[(1S)-2-[(2-{(3S)-3-[(5-chloro-2-pyridyl)oxy]-1-pyrrolidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{(3R)-3-[(6-chloro-2-pyrazinyl)oxy]-1-pyrrolidinyl}-2-oxoethyl)amino]-2-oxo-1-(2-pyridylmethyl)ethyl]-2-propenamide;

5-Chloro-N-[(1S)-2-[(2-{(3R)-3-[(6-chloro-2-pyrazinyl)oxy]-1-pyrrolidinyl }-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{(3R)-3-[(5-methyl-1,3-thiazol-2-yl)oxy]-1-pyrrolidinyl}-2-oxoethyl)amino]-2-oxo-1-(2-pyridylmethyl)ethyl]-2-propenamide;

5-Chloro-N-[(1S)-2-[(2-{(3R)-3-[(5-methyl-1,3-thiazol-2-yl)oxy]-1-pyrrolidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-oxo-2-{[2-oxo-2-(3-{[6-(trifluoromethyl)-4-pyrimidinyl]oxy}-1-azetidinyl)ethyl]amino }-1-(2-pyridylmethyl)ethyl]-2-propenamide;

5-Chloro-N-[(1S)-2-oxo-2-{[2-oxo-2-(4-{[6-(trifluoromethyl)-4-pyrimidinyl]oxy}-1-azetidinyl)ethyl]amino}-1-(2-pyridylmethyl)ethyl]-1-benzofuran-2-carboxamide;

(2E)-3-(4-Chlorophenyl)-N-[(1S)-2-[(2-{4-[(3,5-dichloro-2-pyridyl)oxy]-1-piperidinyl}-2-oxoethyl)amino]-2-oxo-1-(2-pyridylmethyl)ethyl]-2-propenamide;

5-Chloro-N-[(1S)-2-[(2-{4-[(3,5-dichloro-2-pyridyl)oxy]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-oxo-2-{[2-oxo-2-(4-{[3-(trifluoromethyl)-2-pyridyl]oxy}-1-piperidinyl)ethyl]amino }-1-(2-pyridylmethyl)ethyl]-2-propenamide;

5-Chloro-N-[(1S)-2-oxo-2-{[2-oxo-2-(4-{[3-(trifluoromethyl)-2-pyridyl]oxy}-1-piperidinyl)ethyl]amino}-1-(2-pyridylmethyl)ethyl]-1-benzofuran-2-carboxamide;

(2E)-3-(4-Chlorophenyl)-N-[(1S)-2-({2-[4-(4-fluorophenoxy)-1-piperidinyl]-2-oxoethyl}amino)-2-oxo-1-(2-pyridylmethyl)ethyl]-2-propenamide;

5-Chloro-N-[(1S)-2-({2-[4-(4-fluorophenoxy)-1-piperidinyl]-2-oxoethyl}amino)-2-oxo-1-(2-pyridylmethyl)ethyl]-1-benzofuran-2-carboxamide;

(2E)-3-(4-Chlorophenyl)-N-[(1S)-2-oxo-2-[(2-oxo-2-{4-[4-(trifluoromethyl)phenoxy]-1-piperidinyl}ethyl)amino]-1-(2-pyridylrnethyl)ethyl]-2-propenamide;

5-Chloro-N-[(1S)-2-oxo-2-[(2-oxo-2-{4-[4-(trifluoromethyl)phenoxy]-1-piperidinyl}ethyl)amino]-1-(2-pyridylmethyl)ethyl]-1-benzofuran-2-carboxamide;

(2E)-3-(4-Chlorophenyl)-N-[(1S)-2-({2-[4-(4-chlorophenoxy)-1-piperidinyl]-2-oxoethyl}amino)-2-oxo-1-(2-pyridylmethyl)ethyl]-2-propenamide;

5-Chloro-N-[(1S)-2-({2-[4-(4-chlorophenoxy)-1-piperidinyl]-2-oxoethyl}amino)-2-oxo-1-(2-pyridylmethyl)ethyl]-1-benzofuran-2-carboxamide;

(2E)-3-(4-Chlorophenyl)-N-[(1S)-2-oxo-2-({2-oxo-2-[4-(2-pyridylthio)-1-piperidinyl]ethyl}amino)-1-(2-pyridylmethyl)ethyl]-2-propenamide;

5-Chloro-N-[(1S)-2-oxo-2-({2-oxo-2-[4-(2-pyridylthio)-1-piperidinyl]ethyl}amino)-1-(2-pyridylmethyl)ethyl]-1-benzofuran-2-carboxamide;

(2E)-3-(4-Chlorophenyl)-N-[(1S)-2-oxo-2-({2-oxo-2-[4-(2-pyridylsulfonyl)-1-piperidinyl]ethyl}amino)-1-(2-pyridylmethyl)ethyl]-2-propenamide;

5-Chloro-N-[(1S)-2-oxo-2-({2-oxo-2-[4-(2-pyridylsulfonyl)-1-piperidinyl]ethyl}amino)-1-(2-pyridylmethyl)ethyl]-1-benzofuran-2-carboxamide;

(2E)-3-(4-Chlorophenyl)-N-[(1S)-2-[(2-{4-[(5-chloro-2-pyridyl)thio]-1-piperidinyl}-2-oxoethyl)amino]-2-oxo-1-(2-pyridylmethyl)ethyl]-2-propenamide;

5-Chloro-N-[(1S)-2-[(2-{4-[(5-chloro-2-pyridyl)thio]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-oxo-2-({2-oxo-2-[4-(4-pyridylthio)-1-piperidinyl]ethyl}amino)-1-(2-pyridylmethyl)ethyl]-2-propenamide;

5-Chloro-N-[(1S)-2-oxo-2-({2-oxo-2-[4-(4-pyridylthio)-1-piperidinyl]ethyl}amino)-1-(2-pyridylmethyl)ethyl]-1-benzofuran-2-carboxamide;

(2E)-3-(4-Chlorophenyl)-N-[(1S)-2-[(2-{4-[(4-chlorophenyl)thio]-1-piperidinyl}-2-oxoethyl)amino]-2-oxo-1-(2-pyridylmethyl)ethyl]-2-propenamide;

5-Chloro-N-[(1S)-2-[(2-{4-[(4-chlorophenyl)thio]-1-piperidinyl}-2-oxoethyl)amino]-2-oxo-1-(2-pyridylmethyl)ethyl]-1-benzofuran-2-carboxamide;

(2E)-3-(4-Chlorophenyl)-N-[(1S)-2-[(2-{4-[(4-chlorophenyl)sulfonyl]-1-piperidinyl}-2-oxoethyl)amino]-2-oxo-1-(2-pyridylmethyl)ethyl]-2-propenamide;

5-Chloro-N-[(1S)-2-[(2-{4-[(4-chlorophenyl)sulfonyl]-1-piperidinyl}-2-oxoethyl)amino]-2-oxo-1-(2-pyridylmethyl)ethyl]-1-benzofuran-2-carboxamide; and pharmaceutically acceptable salts thereof.

17. The pharmaceutical composition of claim 14, which comprises a compound selected from the group consisting of:

5-Chloro-N-[(1S)-2-oxo-2-({2-oxo-2-[4-(1,3-thiazol-2-yloxy)-1-piperidinyl]ethyl}amino)-1-(2-pyridylmethyl)ethyl]-1-benzofuran-2-carboxamide;

(2E)-3-(4-Chlorophenyl)-N-[(1S)-2-oxo-2-({2-oxo-2-[4-(2-pyrazinyloxy)-1-piperidinyl]ethyl}amino)-1-(2-pyridylmethyl)ethyl]acrylamide;

5-Chloro-N-[(1S)-2-[(2-{4-[(6-methoxy-2-pyridyl)oxy]-1-piperidinyl}-2-oxoethyl)amino]-2-oxo-1-(2-pyridylmethyl)ethyl]-1-benzofuran-2-carboxamide;

5-Chloro-N-[(1S)-2-oxo-2-({2-oxo-2-[4-(2-pyridyloxy)-1-piperidinyl]ethyl}amino)-1-(2-pyridylmethyl)ethyl]-1-benzofiiran-2-carboxamide;

(2E)-3-(4-Chlorophenyl)-N-[(1S)-2-oxo-2-{[2-oxo-2-(4-phenoxy-1-piperidinyl)ethyl]amino}-1-(2-pyridylmethyl)ethyl]acrylamide;

5-Chloro-N-[(1S)-2-oxo-2-({2-oxo-2-[4-(2,2,2-trifluoroethoxy)-1-piperidinyl]ethyl}amino)-1-(2-pyridylmethyl)ethyl]-1-benzofuran-2-carboxamide;

(2E)-3-(4-Chlorophenyl)-N-[(1S)-2-{[2-(4-isopropoxy-1-piperidinyl)-2-oxoethyl]amino }-2-oxo-1-(2-pyridylmethyl)ethyl]acrylamide; and pharmaceutically acceptable salts thereof.

18. A method of treating rejection due to organ transplantation by administering an effective amount of a compound of claim 1 or a pharmaceutically acceptable salt thereof, to a subject in need thereof.

19. A method of treating rejection due to organ transplantation by administering an effective amount of a pharmaceutical composition comprising FK506 and a compound of claim 1 or a pharmaceutically acceptable salt thereof, to a subject in need thereof.

* * * * *